US008800344B2

(12) United States Patent
Stone et al.

(10) Patent No.: US 8,800,344 B2
(45) Date of Patent: Aug. 12, 2014

(54) OXYGEN CONTROL IN BREATHING APPARATUS

(75) Inventors: William C. Stone, Del Valle, TX (US); Nigel Jones, New Market, MD (US); Kurt Sjöblom, Marstrand (SE)

(73) Assignee: Poseidon Diving Systems AB, Vastra Frolunda (SE)

( * ) Notice: Subject to any disclaimer, the term of this patent is extended or adjusted under 35 U.S.C. 154(b) by 1081 days.

(21) Appl. No.: 12/740,194

(22) PCT Filed: Oct. 29, 2008

(86) PCT No.: PCT/SE2008/051229
§ 371 (c)(1),
(2), (4) Date: Nov. 3, 2010

(87) PCT Pub. No.: WO2009/058081
PCT Pub. Date: May 7, 2009

(65) Prior Publication Data
US 2011/0041848 A1    Feb. 24, 2011

Related U.S. Application Data

(60) Provisional application No. 61/000,742, filed on Oct. 29, 2007, provisional application No. 61/000,741, filed on Oct. 29, 2007.

(51) Int. Cl.
*A61M 16/22* (2006.01)
(52) U.S. Cl.
USPC ........................................................ 73/1.06
(58) Field of Classification Search
USPC ...................................................... 73/31.02
See application file for complete search history.

(56) References Cited

U.S. PATENT DOCUMENTS 4,273,120 A    6/1981  Oswell
4,428,372 A *  1/1984  Beysel et al. ............ 128/202.26
(Continued)

FOREIGN PATENT DOCUMENTS

DE    297 10 307    8/1997
DE    29 710 307    9/1997
(Continued)

OTHER PUBLICATIONS

International Search Report for PCT/SE2008/051229, mailed Jan. 28, 2009.
(Continued)

*Primary Examiner* — Hezron E Williams
*Assistant Examiner* — Mark A Shabman
(74) *Attorney, Agent, or Firm* — Nixon & Vanderhye P.C.

(57) ABSTRACT

An oxygen sensor arrangement is arranged to sense the oxygen in a breathing loop of a breathing apparatus. The sensor arrangement comprises at least one primary oxygen sensor arranged to operatively measure the oxygen in the breathing loop, and a control arrangement for obtaining measures from the oxygen sensor. A test channel arrangement is adapted to operatively provide a first gas having a first fraction of oxygen from a first supply to the primary oxygen sensor at a position adjacent to or directly adjacent to the primary oxygen sensor. A first test valve arrangement is arranged to operatively open and close the flow of the first gas through the test channel arrangement. The control arrangement is arranged to operatively actuate the first test valve arrangement so as to provide an amount of the first gas to the primary oxygen sensor via the test channel arrangement.

13 Claims, 33 Drawing Sheets

(56) References Cited

U.S. PATENT DOCUMENTS

| | | | |
|---|---|---|---|
| 4,516,424 A * | 5/1985 | Rowland | 73/31.02 |
| 4,765,193 A * | 8/1988 | Holden et al. | 73/865.9 |
| 4,964,404 A | 10/1990 | Stone | |
| 5,049,317 A * | 9/1991 | Kiske et al. | 261/16 |
| 5,094,235 A | 3/1992 | Westenskow et al. | |
| 5,127,398 A | 7/1992 | Stone | |
| 5,503,145 A | 4/1996 | Clough | |
| 6,003,513 A | 12/1999 | Readey et al. | |
| 6,279,574 B1 | 8/2001 | Richardson et al. | |
| 6,470,885 B1 | 10/2002 | Blue et al. | |
| 6,520,180 B1 | 2/2003 | Sahmkow et al. | |
| 6,712,071 B1 | 3/2004 | Parker | |
| 6,817,359 B2 | 11/2004 | Deas et al. | |
| 7,353,824 B1 | 4/2008 | Forsyth et al. | |
| 8,302,603 B1 | 11/2012 | Weber | |
| 8,424,522 B2 | 4/2013 | Sieber | |
| 2003/0127133 A1 | 7/2003 | Kim | |
| 2003/0188745 A1 | 10/2003 | Deas et al. | |
| 2005/0247311 A1 | 11/2005 | Vacchiano et al. | |
| 2006/0201508 A1 | 9/2006 | Forsyth et al. | |
| 2007/0235030 A1 | 10/2007 | Teetzel et al. | |
| 2009/0250062 A1 | 10/2009 | Reynolds | |
| 2011/0041848 A1 * | 2/2011 | Stone et al. | 128/203.14 |

FOREIGN PATENT DOCUMENTS

| | | |
|---|---|---|
| DE | 100 14 959 | 5/2001 |
| GB | 2 208 203 | 3/1989 |
| GB | 2 404 593 | 2/2005 |
| WO | WO 99/04858 | 2/1999 |
| WO | WO 2005/107390 | 11/2005 |
| WO | WO 2007/126317 | 11/2007 |
| WO | WO 2008/080948 | 7/2008 |

OTHER PUBLICATIONS

Written Opinion of the International Searching Authority for PCT/SE2008/051229, mailed Jan. 28, 2009.
Office Action mailed Jul. 31, 2013 in U.S. Appl. No. 12/740,208.
Office Action mailed Jan. 7, 2013 in U.S. Appl. No. 12/740,208.
Office Action mailed Oct. 8, 2013 in U.S. Appl. No. 12/740,181.
Bally et al., "Performance of Diving Equipment", Health and Safety Laboratory, Copyright 2006.
International Search Report for PCT/SE2008/051226, mailed Jan. 23, 2009.
Written Opinion of the International Searching Authority for PCT/SE2008/051226, mailed Jan. 23, 2009.

* cited by examiner

OXYGEN CONTROL IN BREATHING APPARATUS

This application is the U.S. national phase of International Application No. PCT/SE2008/051229, filed 29 Oct. 2008, which designated the U.S. and claims the benefit of U.S. Provisional Appln. No. 61/000,742, filed 29 Oct. 2007, and U.S. Provisional Appln. No. 61/000,741, filed 29 Oct. 2007, the entire contents of each of which are hereby incorporated by reference.

TECHNICAL FIELD

The present invention relates to breathing apparatuses and the control of oxygen in breathing apparatuses.

BACKGROUND

It is well known to those skilled in the art that breathing apparatuses such as fully closed-cycle breathing apparatuses and similar—e.g. the specific sub-genre known as fully closed-cycle underwater breathing apparatus (CCUBA) or alternatively known as "closed-circuit rebreathers" or "CCR"—offer distinct advantages over the more common open-circuit breathing apparatuses such as e.g. Self-Contained Underwater Breathing Apparatuses (SCUBA) and the like. It should be emphasised that even if the text herein may focus on closed-cycled breathing apparatuses for diving purposes the same or similar advantages applies mutatis mutandis for closed-cycled breathing apparatuses in general and other breathing apparatuses wherein the amount of oxygen in the breathing gas has to be controlled.

Advantages provided by closed-cycle breathing apparatuses and similar are e.g. reduced bubble noise, extremely high gas usage efficiency, and optimized breathing gas composition etc. These and other advantages of closed-cycled breathing apparatuses such as CCRs derive from the fact that the exhaled breathing gas is recycled, filtered of carbon dioxide, replenished with oxygen, and returned to the diver for breathing again. The reduced bubble noise and the increased gas efficiency of a CCR both result from the fundamental function of recycling the breathing gas. The optimized breathing gas composition results from the fact that the oxygen control system of a CCR maintains a substantially constant partial-pressure of oxygen (rather than a constant fraction of oxygen, as in conventional open-circuit breathing apparatuses such as SCUBA and the like).

The partial pressure of a gas is a function of the fraction of the gas multiplied by the ambient pressure. As a diver descends and the depth increases, the ambient pressure also increases. Thus, for a given fraction of oxygen, the partial pressure increases as the depth increases. If the oxygen partial pressure exceeds a certain threshold (approximately 1.4 bar) the high concentration of oxygen and the risk of hyperoxia-induced seizure and other "oxygen toxicity" symptoms is considered unsafe for the diver. For example, the maximum safe depth at which a diver can breathe a mixture containing 50% oxygen is about 18 meters. On the other hand, the lower the oxygen concentration, the greater the concentration of non-oxygen gas constituents, such as nitrogen or helium. It is these non-oxygen components of the breathing mixture that lead to problems of decompression sickness (DCS), also known as "the bends", which include symptoms ranging from pain in the joints, to paralysis, to death. To maximize the amount of time that can be safely spent at any given depth, the non-oxygen portions of the breathing gas should be kept to a minimum; which means that the oxygen should be kept to its maximum safe limit at all points during the dive.

Thus, the advantage of CCR over conventional open-circuit SCUBA in terms of optimized breathing gas composition results from the fact that a CCR can maintain the maximum safe partial pressure of oxygen (PO2) throughout all depths of a dive, thereby minimizing the concentration of non-oxygen gas constituents—leading to increased allowed time at any give depth and/or reduced risk of DCS.

But this advantage comes at a cost. Whereas the breathing mixture for a conventional open-circuit SCUBA diver is fixed based on the composition of the gas in the supply cylinder, the breathing mixture in a CCR is dynamic. Although it is this dynamic mixture capability that affords the CCR one of its primary advantages, a failure of the oxygen control system can be extremely dangerous. A malfunction that allows the PO2 to get too high places the diver at risk of a hyperoxia-induced seizure, which would almost certainly cause the diver to drown. A malfunction that allows the PO2 to get too low may lead to hypoxic-induced blackout, causing the diver to drown and/or suffer severe brain damages. Therefore, perhaps the most critical aspect of any CCR design involves the reliability of the oxygen control system.

Most modern CCRs incorporate one or more electronic oxygen sensors that directly measure the PO2 of the breathing gas. Most such sensors involve a galvanic reaction that produces a voltage output that is proportional to the concentration of the oxygen exposed to the sensor. Electronic systems interpret the signals from the oxygen sensor(s) to control a valve connected to an oxygen supply. When the oxygen sensors detect a PO2 below a certain "setpoint" threshold, the valve is opened and a small amount of oxygen is injected into the breathing gas. The reliability of the oxygen sensors, therefore, is of paramount importance for ensuring a safe breathing gas mixture when using a CCR.

There are a number of ways that oxygen sensors—considered by most experienced CCR divers as the weakest link in the oxygen control system—can fail (i.e., provide false readings), e.g. due to faulty calibration, sensor failure or condensation etc.

In the exemplifying discussions that follow we will assume a commonly available galvanic oxygen sensor (essentially a fuel cell that produces voltage output in response to the PO2 level) that is widely in use in CCR apparatus. However, the following discussions apply mutatis mutandis to all sensors that produce an output signal proportional to PO2 or similar for any other gas.

Calibration

All galvanic oxygen sensors must be calibrated to ensure accurate readings. If a sensor falls out of proper calibration the electronic control system of a CCR will misinterpret the readings. A calibration process typically involves exposing the sensors to one or more known gas mixtures at a known ambient pressure, and deriving calibration constants to the electronic logic that interprets the sensor readings. Calibration is typically conducted manually or semi-automatically prior to the dive, but is sometimes only done periodically. Calibration constants can be recorded incorrectly if the calibration gas mixture deviates from expected (e.g., if the calibration process assumes a mixture of 100% oxygen when a contaminated calibration gas is actually only 80% oxygen), if the ambient pressure is not properly taken into account, if the sensor fails in certain ways as described below, and/or if the user performs the calibration process incorrectly. Attempts to mitigate these problems have included automated calibration routines as part of the standard pre-dive process, incorporation of ambient pressure sensors into the calibration process, and testing against threshold values intended to detect calibration errors.

Sensor Failure by Exhaustion or Similar

Galvanic oxygen sensors eventually fail either through exhaustion of their chemical reaction or other age related degradation of active sensing elements and/or from a host of other environmental and user-caused effects (e.g. abuse, improper use). In many cases, a sensor will simply fail to generate sufficient output voltage at the time of calibration, and will be identified. In other cases, however, a sensor can perform normally up to a certain point, but deviate significantly from linearity in output voltage once the oxygen concentration exceeds a certain value. For example, a sensor could perform normally up to an oxygen concentration of 1.1 bar partial pressure, but then fail to produce a correspondingly higher output voltage at higher oxygen concentrations. Because the calibration process of most CCR systems uses 100% oxygen at ambient pressure (i.e., 1 bar partial pressure) in a pre-dive calibration, the calibration process may appear to complete correctly, but the system may not be able to properly interpret readings when the sensor is exposed to oxygen partial pressures above 1 bar.

Sensor Failure by Condensation or Similar

Moreover, one of the most common modes of oxygen sensor failure involves condensation. The breathing gas in a CCR is humidified to near-saturation when the gas is exhaled from the diver's lungs. In most cases, ambient water temperature is cooler than body core temperature, so as the breathing gas is cooled in the CCR breathing loop, liquid condensation inevitably forms. As a consequence, the inside walls of the CCR breathing pathways are typically dripping wet with condensation after a short period of time. The total volume of condensate can exceed several tens of milliliters per hour of dive time. This condensation can affect the oxygen sensor and cause erroneous readings. It can also lead to premature failure of the sensor. In some circumstances, a thin film of condensate can form across the active sensing face of the oxygen sensor (frequently a metal mesh or hydrophobic membrane), trapping a tiny pocket of gas against the sensor that is isolated from the breathing gas mixture. This is among the most dangerous forms of oxygen sensor failure, because it provides a false but plausible reading to the electronics, concealing the nature of the failure. For example, if the trapped pocket of gas has an oxygen concentration that is below a certain "setpoint" threshold, then the control system will continue to add oxygen to the breathing loop until the actual breathed PO2 reaches dangerously high levels. Conversely, if the trapped pocket of gas has a PO2 above the "setpoint" value, the control system will fail to add any oxygen at all, and the PO2 of the breathing gas will gradually diminish due to the diver's metabolic oxygen consumption, until hypoxic levels are reached and the diver blacks out.

Attempts to mitigate this problem include "water traps" and absorbent pads in the breathing loop designed to divert collected condensate away from the oxygen sensors; strategic placement of sensors in areas least likely to form condensation; placement of sensors on different planes to reduce the probability of multiple sensors collecting condensate simultaneously.

Even more importantly, almost all electronically-controlled CCR systems thus far developed attempt to safeguard against the consequences of failed oxygen sensors through the incorporation of triplex redundancy (that is, by incorporating three oxygen sensors in the CCR). This is i.a. based on the notion that if only one oxygen sensor is used, and it fails in a way that gives otherwise plausible readings, then there is no logical way to recognize that the sensor has failed. Similarly, if two sensors are used and one of them is giving a false reading, the control system can logically recognize a problem (unless both sensors fail in the same way), but cannot determine which sensor is correct and which has failed. With three oxygen sensors, so the conventional thinking goes, the system has "voting" logic. Assuming only one sensor fails at a time then the control system can be designed to interpret the two readings that agree within some pre-accepted tolerance as correct and thereby isolate the bad sensor reading.

Examples of breathing apparatuses that use three oxygen sensors and a "voting" logic or similar are disclosed in the patent documents U.S. Pat. No. 6,712,071 (Parker), GB 2404593 (Deas) and CA 2564999 (Straw).

Though ubiquitous among modern rebreather designs, the three-sensor approach to monitoring oxygen concentration in the breathing mixture is far from perfect. First, some more or less arbitrary threshold values must be established in order to carry out the voting logic. Because sensor readings can be slightly unstable in the chaotic breathing gas mixture of a CCR, a sensor must deviate from the other two sensors by a certain minimum threshold amount before it is considered suspect.

Then there is the question of what this threshold is measured against? For example, should the basis for the threshold comparison of one potentially errant sensor reading be the average value of the remaining two sensors, or the value of the sensor with the closest reading (i.e., the sensor giving the "middle" reading of the three) or perhaps something else?

Another problem with reliance upon the triple-redundant oxygen sensor system is the fact that sometimes two sensors fail the same way—often due to asymmetric condensate formation or because a user may have replaced one sensor with a fresh one and the other two are at the end of their useful life but may have exhibited in-range readings prior to the start of a dive (there are many such possibilities)—such that the apparently errant sensor reading is actually the correct reading. This mode of failure is particularly dangerous in that the control system actively ignores the true reading. Although this failure mode may seem unlikely, it has been documented on countless occasions in actual dive logs. Indeed, there have even been documented cases where all three sensors fail simultaneously such that all three give the same, but false reading. Other documented cases involve situations where no two sensors agree.

Once the threshold values and basis of comparison (voting logic algorithm) are determined, there is still the question of how best to adjust the oxygen control system in the event of an apparently failed sensor. Given two concordant values, and one errant value, should the control system simply ignore the errant value altogether and base its control logic on the average of the remaining two sensors? Or, should it base its control on the "middle" value of the three sensor readings—just in case the apparently errant sensor may be correct? Or, should additional logic be used such that the "setpoint" is adjusted dynamically, so that both the highest sensor value and the lowest sensor value are both kept within life-sustaining limits at all times? And what should the control system do in the even that no two oxygen sensors agree? Should it bias its logic to safeguard more rigorously against hypoxia, or hyperoxia?

Indeed, there are probably as many different answers to the questions and problems indicated above as there are people who have designed CCR oxygen control systems.

Although using three oxygen sensors and using sensors designed specifically for humid environments can mitigate some of the problems indicated above, all known CCR oxygen control systems are subject to failures due to one or more of the above problems. Hence, in view of the above there seems to be a need of improvements related to the control of oxygen in the breathing gas of a closed-cycle breathing apparatus and similar.

SUMMARY OF THE INVENTION

The present invention represents a new approach to oxygen control systems in closed-cycle breathing apparatuses such as CCRs and similar and other breathing apparatuses wherein the amount of oxygen in the breathing gas has to be controlled, e.g. continuously monitored. Other examples can e.g. be found in the medical area, e.g. such as medical ventilators and respirators of different kinds etc.

The control system involves automated active testing and/or monitoring of an oxygen sensor that is more reliable than the passive triple-redundancy control system that is currently in common use. The approach capitalizes on a repeated testing and monitoring technique and the availability of pure oxygen and/or a primarily non-oxygen gas supply (e.g., air), which are both typically available on almost all CCR systems. Here, it should be emphasised that even if the text herein may focus on closed-cycled breathing apparatuses for diving purposes the same or similar applies mutatis mutandis for other closed-cycled breathing apparatuses or similar.

For example, an oxygen control system according to an embodiment of the present invention incorporates two oxygen sensors (one may be designated as the "Primary Sensor", and the other may be designated as the "Secondary Sensor") and a minimum of three electronically controlled gas valves: two used to inject oxygen, and one used to inject "diluent" gas (i.e., a mixture containing primarily non-oxygen but nonetheless constituting a gas mixture that is directly breathable in open circuit mode within some regime of a planned dive—typically it is designed to be breathable at the maximum planned dive depth). The "diluent" gas supply may e.g. be air (~21% oxygen, ~79% nitrogen and other trace gases), but any breathable mixture containing at least some (known) oxygen fraction will serve the same purpose. It should be added that oxygen gas has a fraction of oxygen that is 1 or nearly 1 (i.e. 100% or nearly 100% oxygen). As indicated above, the it is preferred that the oxygen control system periodically validates the readings of the Primary Sensor using controlled direct injections of either oxygen or diluent (depending on the depth and the circumstances) and monitoring the response of the sensor to validate accurate readings. It is also preferred that these gas injections also serve the purpose of removing any condensation that may form on the face of the sensors, thus eliminating one of the common failure modes described above. It is also preferred that the Secondary Sensor is used to monitor the oxygen content of the breathing gas while the Primary Sensor is being validated, and also to safeguard against possible failure modes of the Primary Sensor validation system, e.g. possible leakage in the control valves that inject oxygen or diluent onto the primary sensor which would cause faulty oxygen readings.

Initial Sensor Calibration

Since it is preferred that the primary sensor in the present invention has direct access to both oxygen and known diluent mixtures (e.g., air) via electronically-controlled microvalves, the system is capable of calibrating itself without any input from the user and it is capable of performing the calibration with an exceedingly small volume of consumable gas, which is an important performance measure in CCR systems and which allows these systems to be substantially more compact than open circuit systems providing equivalent diving range at a given depth. Nor do preferred embodiments of the present invention require any reliance of proper user-initiated calibration routines or any interaction of the user at all. At initial power-up, the system will automatically inject a burst of pure diluent gas (e.g., air) directly on the primary Oxygen Sensor, reliably exposing it to a known low-oxygen mixture. If a diver is not breathing on the CCR breathing loop at the time of calibration, then a sufficient volume of diluent gas can be injected to also expose the nearby Secondary Oxygen Sensor. The same procedure applies to the oxygen supply mixture as well. These two known points provide a precise 2 point calibration for the primary oxygen sensor.

Although there may have been previous attempts to automatically calibrate oxygen sensors as part of the normal start-up routine in a CCR, typically these calibrations only apply to the pure oxygen portion of the calibration and typically they require a large wasteful volume of oxygen to adequately ensure that the sensors themselves are exposed to a reliably high concentration of oxygen. One reason for known calibration approaches being wasteful and inaccurate with regard to auto-calibration is that the same system used to add metabolic oxygen is the one used in the calibration. It is traditional industry practice to inject metabolic make up oxygen in a fashion that mixes the gas in the breathing loop long before reaching the oxygen sensors. Because of this, if one is using the metabolic oxygen valve for calibration purposes the entire breathing loop (as much as 7 liters in volume) must be completely flushed several times in order to approximate an good calibration. Even so, such loop-flushing procedures are never 100% complete and are subject to user intervention (e.g. setting a valve position wrong prior or during the calibration). Similarly, the breathing loop must then be manually completely flushed with air in order to achieve the 2-point calibration. Both actions require the interaction of the diver with the system and are therefore not truly automatic. Further, this approach is only possible on the surface prior to a dive; it cannot be used to detect a true sensor failure during a dive. Further, such an approach is subject to all of the above-described sensor failure and spoofing scenarios which could lead to a significant probability of an incorrect calibration.

Preferred embodiments of the invention described here—because of the availability of oxygen and diluent (e.g., air) directly applied to the primary Oxygen Sensor via the electronically-controlled Oxygen Test Valve and Diluent Test Valve, and the proximity of the Secondary Oxygen Sensor to the Primary Oxygen Sensor—are much more effective and efficient for establishing accurate calibration of the oxygen sensors prior a dive.

Additional embodiments of the invention have been made even more reliable by:

1) incorporating threshold limits to detect when a sensor falls out of acceptable output voltage values at calibration time;
2) use of algorithmic analysis of a stored log of calibration values to detect calibration trends, alerting the user to a need to replace a sensor; and
3) clear "Do not Dive" indicators that prevent the user from operating the system in the event that the pre-dive calibration process does not complete successfully.

An additional benefit of the automatic pre-dive check as indicated above is that it can also serve as a pre-dive verification that the correct gas mixture (oxygen or diluent) is connected to the correct supply regulator (within calibration threshold tolerances of the sensors).

In-Dive Sensor Testing with Diluent Gas

Another new feature of embodiments of the oxygen control system described herein is the ability to monitor and test the function of oxygen sensors during the course of the dive— either at periodic time intervals, or in response to specific circumstances detected by the Electronic Control System. When desired, the system can automatically inject a small amount of diluent gas onto the Primary Oxygen Sensor, and then observe the resultant reading from the sensor as it is interpreted by the electronic control system. With an ambient pressure sensor and a known oxygen fraction in the diluent supply, the Primary Oxygen Sensor can be exposed to a known partial pressure of oxygen at any moment during the dive, and monitored to ensure that the sensor responds with the correct reading. Failure of this test can initiate an alert to the diver that the dive should be aborted immediately.

In-Dive Sensor Testing with Oxygen

Because embodiments of the system also has access to 100% oxygen and can inject it directly onto the Primary Oxygen Sensor, the system is also capable of testing the linearity of the sensor voltage output at partial pressures in excess of 1 bar (i.e., the maximum calibration value during pre-dive). For example, when the Electronic Control System detects via an ambient pressure sensor that the diver has reached a depth of 20 feet (6 m), where the ambient pressure is approximately 1.6 bar, a small burst of oxygen directly on the Primary Oxygen Sensor can ensure that the calibration constants apply reliably for readings at partial pressures well above 1.0 bar. Thus, if the system is set to maintain an oxygen partial pressure of 1.3 bar, there can be confidence in the reliability of the readings at that value, even though it is higher than the maximum pre-dive calibration value of 1.0 bar. As with the diluent injections, the volume of oxygen needed to be injected to perform this test is so small that it would not have a significant impact on the overall gas composition in the CCR breathing loop. Hence, embodiments of the invention described herein offer a full range sensor calibration extending beyond the typical calibration performed on the surface at 1 bar. Furthermore, this calibration can be performed in a fully automated fashion that is "transparent" to, and requires no interaction from, the user.

Although in theory the in dive validation could be done through the use of either diluent or pure oxygen, it is safer to use diluent since it can be injected safely over the entire range of possible ambient pressure profiles without the risk of excess gas addition leading to a potential oxygen toxic state. Furthermore, most oxygen sensors have a limiting output value and this value can be easily exceeded if pure oxygen were injected, for example, during the deeper portions of a dive. For these reasons, it is recommended that most auto-validation is done with diluent gas.

A Secondary Oxygen Sensor

The incorporation of a Secondary Oxygen Sensor into embodiments of the system adds to the reliability of the overall sensor monitoring system architecture in several ways. During periods when the Primary Oxygen Sensor is not being actively tested, the Secondary Oxygen Sensor can be compared to the Primary Oxygen Sensor to ensure concurrency of readings. If the readings are not concurrent, the system can be triggered to perform a test on the Primary Oxygen Sensor. If the discrepancy of readings was caused by condensation on the Primary Oxygen Sensor, the test itself may correct the problem. If the Primary Oxygen Sensor fails the test, the system can issue an abort alert, and initiate a test of the Secondary Oxygen Sensor, e.g. by increasing the volume of gas injected at the Primary Oxygen Sensor. If the Primary Oxygen Sensor passes the test, but the Secondary Oxygen Sensor is still providing inconsistent readings (e.g., if condensation has formed on the Secondary Oxygen Sensor, or if the Secondary Oxygen Sensor has failed for some other reason), then an abort alert can be issued to the diver. Another reason for incorporating a Secondary Oxygen Sensor that is not connected directly to the output from the Diluent Test Valve or the Oxygen Test Valve, is that it can serve as a "sentry" to safeguard against small leaks from either of the test valves. If there was a large leak of either of these valves, it is likely that the control logic of the Electronic Control System would recognize it immediately, and initiate an abort alert to the diver. However, if there was a very small leak in either of the test valves, a trickle of gas onto the Primary Oxygen Sensor might be such that it would bias the reading, but not so much that it could be detected by the Electronic Control System. The sensor would be functioning normally, and would pass all tests, but because the gas in immediate proximity to the sensor membrane is exposed to a contaminated gas mixture (not the actual breathing gas mixture) it would provide erroneous readings and lead to a malfunction of the oxygen control system. Malfunction in this sense meaning that the metabolic oxygen addition solenoid would fail to add oxygen in the event that the true PO2 dropped below the pre-set threshold for adding oxygen or, alternatively, that the metabolic oxygen addition solenoid would add oxygen when the true PO2 was within acceptable limits or higher than acceptable limits. Having a Secondary Oxygen Sensor that is not directly exposed to the gas coming from the test valves would result in detection of this failure mode due to discrepancy of readings between the two sensors (as described above). If the leak is so large that it causes contamination of the Secondary Oxygen Sensor, it would be large enough to detect by itself, and even still would not affect the Secondary Sensor as much as the Primary Oxygen Sensor, hence causing a (detectable) discrepancy in readings. Yet another reason for having a Secondary Oxygen Sensor is that it can be used to monitor the actual breathing gas while the Primary Oxygen Sensor is being tested. Whereas the Primary Oxygen Sensor is not exposed to the actual breathing mixture during tests, the Secondary Oxygen Sensor continues to monitor the breathing loop gas.

Diluent Injection Capability

Having an electronically controlled diluent valve also provides an opportunity for a feature not available in any other known CCR control system: that is, the ability to automatically reduce the oxygen concentration in the breathing loop. Whereas most CCR oxygen control systems operate by injecting oxygen via an electronically-controlled valve whenever the oxygen concentration in the breathing gas drops below a certain "setpoint" value, they are incapable of responding in any way to a situation when the oxygen level increases above the setpoint value. They are, in fact, "open loop" control systems. The system described here is capable true closed-loop control—that is, the diluent valve can be used to inject a volume—preferably a substantial volume—of diluent gas into the breathing mixture if the detected oxygen concentration is too high. Although this may temporarily obfuscate the readings of the oxygen sensors, the sensors would restore functionality as soon as the breathing gas moved through the loop as the diver breathed, and the important factor is that a safer (reduced oxygen concentration) gas mixture would be delivered to the diver.

Oxygen Replenish Valve

Because oxygen replenishment is a normal function of a CCR oxygen control system, it would be unwise to use the Oxygen Test Valve for this purpose. Thus, the present invention utilizes a separate Oxygen Replenish Valve (or a plurality of valves) for injecting oxygen, intended to replenish that which is consumed by the diver, into a location on the breathing loop where it will not impact the oxygen sensor readings directly. The oxygen injected to replenish the metabolized oxygen would be adequately mixed with the breathing loop gas before it reaches either oxygen sensor.

However, in an emergency situation in which the normal oxygen replenish valve(s) fail to add oxygen to the system, or in a situation wherein an auxiliary safety valve (either manually operated or automatically operated) has closed the oxygen supply feeding the oxygen replenishment valves, then it would be possible to use the oxygen test valve to automatically add oxygen to the system. In such an event, which would be rare, the firmware residing on the system microcontroller would halt the normal oxygen sensing and firing algorithm and would wait for a period of time necessary for the oxygen that was injected through the oxygen test valve to have cleared the respective oxygen sensor cavitie(s) and been flushed with the mixed breathing gas resulting from the emergency oxygen addition pulse. At this point the firmware emergency algorithm may re-assess the situation, measure the system PO2, and determine if further emergency oxygen addition is required through the oxygen test valve.

Automated Condensation Purge

The injections of (dry) diluent gas directly onto the sensor as mentioned above also have the simultaneous effect of blowing off any accumulated condensation near the sensor membrane. It is preferred that this injection process is turbulent and designed in such a fashion (e.g. through computational fluid dynamics modelling and empirical testing) as to lift off condensation from the oxygen sensor sensing surface and cause it to be ejected into the breathing loop where it can be captured and stored (e.g. in a sponge trap), and to achieve this effect with the least amount of expended consumable gas. For example, in some embodiments it is preferred that the gas is injected at an oblique angle with respect to the surface of the oxygen sensor. The oblique angle may e.g. be less than 70 degrees or less than 60 degrees or less than 50 degrees, or less than 40 degrees or less than 30 degrees with respect to the surface of the oxygen sensor. Indeed, the oblique angle may be substantially equal to or just exceeding zero degrees, indicating that the gas is injected substantially in parallel to the surface of the oxygen sensor. This is in clear contrast to an injection at substantially 90 degrees, which would achieve a very poor condensation purge. Such a purge would even risk pressuring gas molecules into the surface of the oxygen sensor with a potential of disturbing and/or obfuscating the measures.

It is also preferred that the injected gas can be pre-warmed by exposure to a heat exchange mechanism with the ambient breathing loop gas to offset the chilling effect on the gas when it is decompressed from an intermediate pressure stage (i.e., upstream of the test valves). If only the Primary Oxygen Sensor is to be tested, a small volume of gas is injected. If there is a need to test the Secondary Oxygen Sensor, a larger volume of gas can be injected and the response of the Secondary Sensor can be monitored for accuracy and correct calibration. In either case (small injection or "large" injection), the volume of gas injected is small enough that it will have negligible impact on the overall breathing gas composition but it will have the beneficial effect of purging condensate automatically from the primary sensor without diver intervention.

A first embodiment of the present invention is directed to an oxygen sensor arrangement for sensing the oxygen in a breathing loop of a breathing apparatus. The oxygen sensor arrangement comprises: at least one primary oxygen sensor arranged to operatively measure the oxygen in the breathing loop, and a control arrangement for obtaining measures from said oxygen sensor. A test channel arrangement is adapted to operatively provide a first gas having a first fraction of oxygen from a first gas supply to said primary oxygen sensor at a position adjacent to or directly adjacent to said primary oxygen sensor. At least a first test valve arrangement is arranged to operatively open and close the flow of said first gas through said test channel arrangement. The control arrangement is arranged to operatively actuate said first test valve arrangement so as to provide an amount of said first gas to said primary oxygen sensor via said test channel arrangement.

A second embodiment of the present invention, comprising the features of the first embodiment, is directed to an oxygen sensor arrangement wherein: the test channel arrangement is adapted to provide a second gas having a second fraction of oxygen from a second gas supply to said primary oxygen sensor at a position adjacent to or directly adjacent to said primary oxygen sensor. At least a second test valve arrangement is arranged to operatively open and close the flow of said second gas through said test channel arrangement. The control arrangement is arranged to operatively actuate said second test valve arrangement so as to provide an amount of said second gas to said primary oxygen sensor via said test channel arrangement.

A third embodiment of the present invention, comprising the features of the second embodiment, is directed to an oxygen sensor arrangement wherein: the test channel arrangement comprises a first test channel arrangement for providing said first gas from said first gas supply to said primary oxygen sensor at a first position adjacent to or directly adjacent to said primary oxygen sensor, and a second test channel arrangement for providing said second gas from said second gas supply to said primary oxygen sensor at a second position adjacent to or directly adjacent to said primary oxygen sensor.

A fourth embodiment of the present invention, comprising the features of the first embodiment, is directed to an oxygen sensor arrangement wherein: the control arrangement is arranged to operatively obtain at least one first test measure from said primary oxygen sensor when it is provided with an amount of said first gas.

A fifth embodiment of the present invention, comprising the features of the fourth embodiment, is directed to an oxygen sensor arrangement wherein: the control arrangement is arranged to operatively obtain at least one second test measure from said primary oxygen sensor when it is provided with an amount of said second gas.

A sixth embodiment of the present invention, comprising the features of the fifth embodiment, is directed to an oxygen sensor arrangement wherein: the control arrangement is arranged to operatively: calculate at least a first calibration point using said first test measure and at least using the known fraction of oxygen in the first gas, and calculate at least a second calibration point using said second test measure and at least using the known fraction of oxygen in the second gas, and generate a calibration curve for said primary oxygen sensor at least based on said first calibration point and said second calibration point.

A seventh embodiment of the present invention, comprising the features of the fourth or the fifth embodiment, is directed to an oxygen sensor arrangement wherein said control arrangement is arranged to operatively: obtain a validation point value using said first test measure or said second test measure, and obtain an expected value for the validation point value, at least using the known fraction of oxygen in the first gas or the known fraction of oxygen in the second gas, and determine if the validation point value deviates from the expected value more than a predetermined amount.

An eighth embodiment of the present invention, comprising the features of the sixth and the seventh embodiments, is directed to an oxygen sensor arrangement wherein said control arrangement is arranged to operatively: obtain the expected value for the validation point value by using the calibration curve so as to compensate for possible deviations in said primary oxygen sensor.

A ninth embodiment of the present invention, comprising the features of the fourth or the fifth embodiment, is directed to an oxygen sensor arrangement comprising at least one pressure sensor for measuring the ambient pressure affecting the breathing loop, wherein: the control arrangement is arranged to operatively obtain measures from said pressure sensor in connection with at least one of said first test measure or said second test measure, so as to provide the partial pressure of oxygen (PO2) for at least one of said first test measure or said second test measure.

A tenth embodiment of the present invention, comprising the features of any one of the first, the second or the third embodiment, is directed to an oxygen sensor arrangement wherein: said first oxygen sensor is arranged in a cavity that is in fluid communication with the breathing loop and that is provided with at least one output orifice for said test channel arrangement, which output orifice is arranged at a position adjacent to or directly adjacent to said oxygen sensor so that at least on of said first gas or said second gas can be operatively injected at an oblique angle with respect to the surface of the primary oxygen sensor.

An eleventh embodiment of the present invention, comprising the features of the first or the second embodiment, is directed to an oxygen sensor arrangement further comprising at least one secondary oxygen sensor for measuring the oxygen in the breathing loop, wherein: said control arrangement is arranged to operatively obtain measures from the secondary oxygen sensor and the primary sensor when no test valve arrangements are actuated.

A twelfth embodiment of the present invention, comprising the features of the eleventh embodiment, is directed to an oxygen sensor arrangement wherein: said control arrangement is arranged to operatively actuate at least one of said first test valve arrangement r said second test valve arrangement if the primary sensor measures deviates from the secondary oxygen sensor measures more than a predetermined amount.

A thirteenth embodiment of the present invention, comprising the features of the eleventh embodiment, is directed to an oxygen sensor arrangement wherein: said secondary oxygen sensor is arranged at a distance from the gas output of at least one of said first test valve arrangement or said second test valve arrangement, such that a gas leakage from at least one of said first test valve arrangement or said second test valve arrangement will cause the secondary sensor to operatively provide a different measure compared to the measure provided by the primary oxygen sensor.

A fourteenth embodiment of the present invention, comprising the features of the eleventh embodiment, is directed to an oxygen sensor arrangement wherein: the secondary oxygen sensor is arranged nearby the primary sensor so as to enable said control arrangement is arranged to operatively actuate at least one of said first test valve arrangement or said second test valve arrangement so as to validly expose the secondary oxygen sensor by gas having said first fraction of oxygen or said second fraction of oxygen.

A fifteenth embodiment of the present invention, comprising the features of the first or the second embodiment, is directed to an oxygen sensor arrangement wherein: at least one cut-off valve arrangement, operable by the control arrangement, is arranged to operatively open and close a possible gas leakage from at least one of said first test valve arrangement or said second test valve arrangement to said at least one primary oxygen sensor.

A sixteenth embodiment of the present invention, comprising the features of the fifteenth embodiment, is directed to an oxygen sensor arrangement wherein: said cut-off valve arrangement is opened during actuation of said first test valve arrangement or during actuation of said second test valve arrangement.

A seventeenth embodiment of the present invention is directed to a method for sensing the oxygen in a breathing loop of a breathing apparatus wherein the method in an oxygen sensor arrangement comprises the steps of; actuating a first test valve arrangement so as to provide an amount of a first gas having a first fraction of oxygen via a test channel arrangement to a primary oxygen sensor at a position adjacent to or directly adjacent to said primary oxygen sensor.

An eighteenth embodiment of the present invention, comprising the features of the seventeenth embodiment, is directed to a method comprising the steps of: actuating a second test valve arrangement so as to provide an amount of a second gas having a second fraction of oxygen via said test channel arrangement to said primary oxygen sensor at a position adjacent to or directly adjacent to said primary oxygen sensor.

A nineteenth embodiment of the present invention, comprising the features of the eighteenth embodiment, is directed to a method comprising the steps of providing said first gas through a first test channel arrangement to said primary oxygen sensor at a first position adjacent to or directly adjacent to said primary oxygen sensor, and providing said second gas through a second test channel arrangement to said primary oxygen sensor at a second position adjacent to or directly adjacent to said primary oxygen sensor.

A twentieth embodiment of the present invention, comprising the features of the seventeenth embodiment, is directed to a method comprising the steps of: obtaining at least one first test measure from said primary oxygen sensor when it is provided with an amount of said first gas.

A twenty first embodiment of the present invention, comprising the features of the twentieth embodiment, is directed to a method comprising the steps of obtaining at least one second test measure from said primary oxygen sensor when it is provided with an amount of said second gas.

A twenty second embodiment of the present invention, comprising the features of the twenty first embodiment, is directed to a method comprising the steps of calculating at least a first calibration point using said first test measure and at least using the known fraction of oxygen in the first gas, and calculating at least a second calibration point using said second test measure and at least using the known fraction of oxygen in the second gas, and generating a calibration curve for said primary oxygen sensor at least based on said first calibration point and said second calibration point.

A twenty third embodiment of the present invention, comprising the features of the twenty first embodiment, is directed to a method comprising the steps of obtaining a validation point value using said first test measure or said second test measure, and obtaining an expected value for the validation point value, at least using the known fraction of oxygen in the first gas or the known fraction of oxygen in the second gas, and determining if the validation point value deviates from the expected value more than a predetermined amount.

A twenty fourth embodiment of the present invention, comprising the features of the twenty second and the twenty third embodiments, is directed to a method comprising the steps of obtaining the expected value for the validation point value by using the calibration curve so as to compensate for possible deviations in said primary oxygen sensor.

A twenty fifth embodiment of the present invention, comprising the features of the twenty first or the twenty second embodiment, is directed to a method comprising the steps of obtaining measures the ambient pressure from a pressure sensor in connection with at least one of said first test measure or said second test measure, so as to provide the partial pressure of oxygen (PO2) for at least one of said first test measure or said second test measure.

A twenty sixth embodiment of the present invention, comprising the features of any one of the seventeenth or the eighteenth or the nineteenth embodiment, is directed to a method comprising the steps of injecting said first gas or said second gas at an oblique angle with respect to the surface of the primary oxygen sensor.

A twenty seventh embodiment of the present invention, comprising the features of the seventeenth or the eighteenth embodiment is directed to a method comprising the steps of obtaining measures from a secondary oxygen sensor and the primary sensor when no test valve arrangements are actuated.

A twenty eighth embodiment of the present invention, comprising the features of the twenty seventh embodiment, is directed to a method comprising the steps of actuating at least one of said first test valve arrangement or said second test valve arrangement if the primary sensor measures deviates from the secondary oxygen sensor measures more than a predetermined amount.

A twenty ninth embodiment of the present invention, comprising the features of the twenty seventh embodiment, is directed to a method comprising the steps of arranging the secondary oxygen sensor at a distance from the gas output of at least one of said first test valve arrangement or said second test valve arrangement, such that a gas leakage from at least one of said first test valve arrangement or said second test valve arrangement will cause the secondary sensor to operatively provide a different measure compared to the measure provided by the primary oxygen sensor.

A thirtieth embodiment of the present invention, comprising the features of the twenty seventh embodiment, is directed to a method comprising the steps of arranging the secondary oxygen sensor nearby the primary sensor and actuating at least one of said first test valve arrangement or said second test valve arrangement so as to validly expose the secondary oxygen sensor by gas having said first fraction of oxygen or said second fraction of oxygen.

A thirty first embodiment of the present invention, comprising the features of the seventeenth or the eighteenth embodiment, is directed to a method comprising the steps of actuating at least one cut-off valve arrangement to open and close a possible gas leakage from at least one of said first test valve arrangement or said second test valve arrangement to said at least one primary oxygen sensor.

A thirty second embodiment of the present invention, comprising the features of the thirty first embodiment, is directed to a method comprising the steps of opening said cut-off valve arrangement except actuation of said first test valve arrangement or during actuation of said second test valve arrangement.

Further advantages of the present invention and embodiments thereof will appear from the following detailed description of the invention.

It should be emphasized that the term "comprises/comprising" when used in this specification is taken to specify the presence of stated features, integers, steps or components, but does not preclude the presence or addition of one or more other features, integers, steps, components or groups thereof.

It should also be emphasised that the methods defined in the appended claims may, without departing from the present invention, comprise further steps and/or the steps specified may be performed in another order than the order in which they appear in the claims.

DETAILED DESCRIPTION OF EMBODIMENTS

Basic Breathing Apparatus

Figure 1:
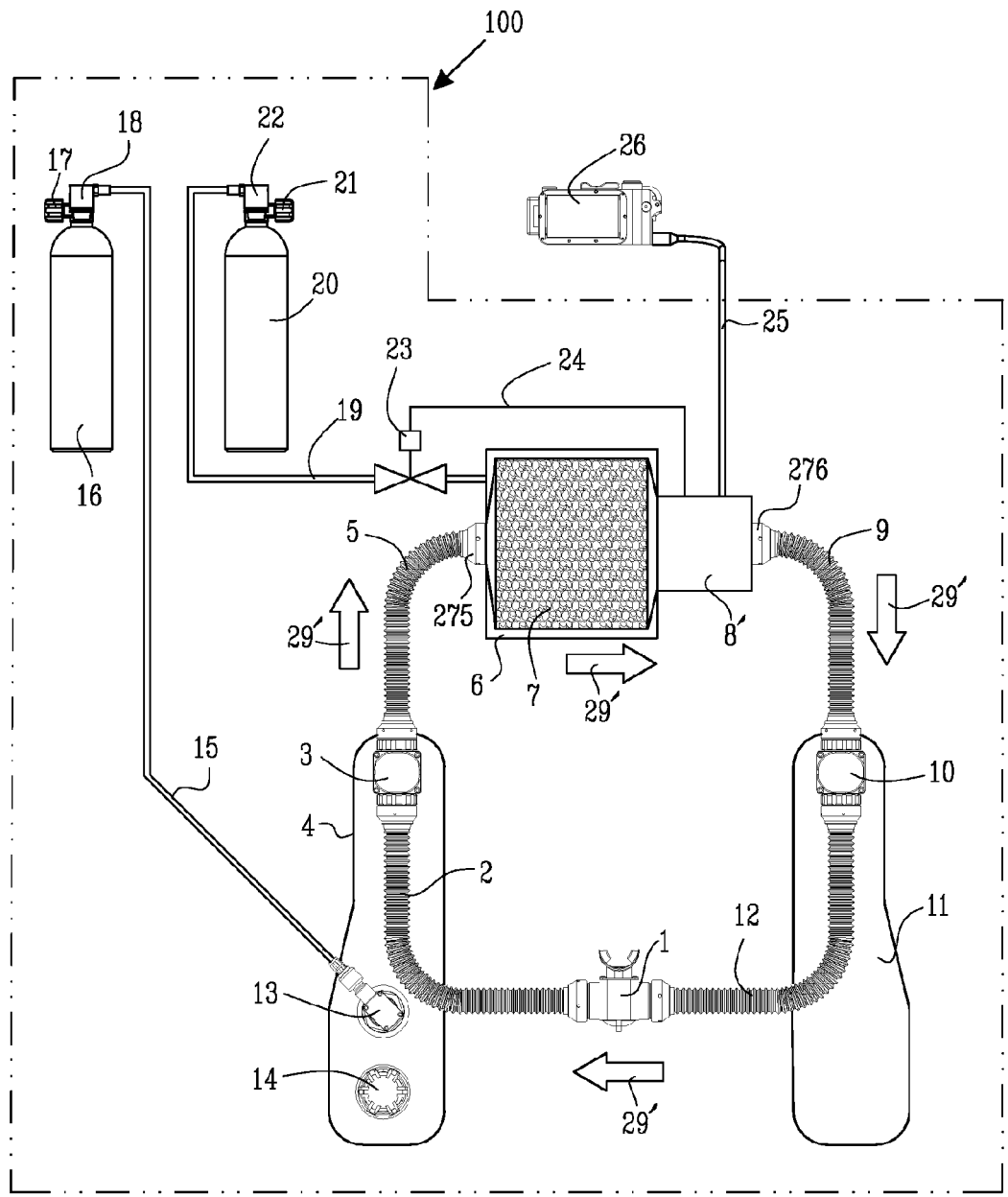
FIG. 1 shows in schematic mode an exemplifying breathing apparatus in the form of a typical modern Closed-Circuit Rebreather (CCR) 100.

FIG. 1 shows in schematic mode of an exemplifying breathing apparatus 100 in the form of a typical modern CCR architecture, e.g. as elaborated in the patent document U.S. Pat. No. 4,964,404 (Stone). The general operation of such a CCR is as follows: the user breathes into a mouthpiece 1 that contains checkvalves (not shown) that enforce the flow of gas in a preferential direction, as schematically indicated by the arrows 29' in FIG. 1. The expelled gas (from exhalation) travels down breathing hose 2 and into junction block 3, which permits passage of the gas into a flexible bladder 4 known as a "counterlung". In advanced CCR designs (e.g. as in the patent document by Stone cited above) two counterlungs are used—an exhalation counterlung 4 and an inhalation counterlung 11 such that each has a volume equal to about half the exhalation volume of the diver. As the exhalation counterlung 4 fills the gas then continues through junction block 3 and through breathing hose 5, which carries the gas to a hose junction 275 with a gas processing unit 6. Inside the gas processing unit 6 the gas is passed through a carbon dioxide removal means 7, which frequently takes the form of an absorbent that chemically reacts with the gaseous carbon dioxide to form a carbonate molecule. The clean gas then continues on to an Oxygen Control Module 8', which i.a. performs the critical oxygen sensing and control functions of the CCR, which preferably includes at least the following tasks:

Sense the PO2 of the breathing gas

Determine whether the measured PO2 is below acceptable limits

Control a valve so as to add oxygen if the PO2 is too low

Send a signal to a display that displays the current PO2

When oxygen is added pure oxygen contained in a pressure vessel 20 with manual tank valve 21 and first stage regulator 22 sends pure oxygen gas at reduced pressure (generally at 8 to 12 bar pressure) through tube/hose means 19 to an electronically controlled valve 23 (e.g. a solenoid valve), which is connected to the Oxygen Control Module 8' by an electrical control cable 24.

There are many variations on the well known general concept as indicated above and the decision making process can be either performed using analogue or digital electronics, although the later has almost entire supplanted the former in the last decade. It is common now to have cable 25 (or wireless data relay means) leading from the Oxygen Control Module 8' to a display 26 that can provide sophisticated amounts of alphanumeric and symbolic information to the user relating to the status of the apparatus breathing apparatus 100 and, as well, tactical information both direct (e.g. present depth, tank supply gas pressures) as well as derived (e.g. decompression status, maximum depth etc) information.

The breathing gas then exits the Gas Processing Unit 6 and the Oxygen Control Module 8' at manifold 276, travels through hose 9 to junction block 10 and enters the inhalation counterlung 11, which continues to fill up until the volume of gas in counterlung 11 combined with that in counterlung 4 comprise the complete volume of gas exhaled by the user (assuming no loss). Upon inhalation, the diver first draws air (through mouthpiece 1) from the inhalation counterlung 11 until it collapses, whereupon gas remaining in exhalation counterlung 4 is pulled through the Gas Processing Unit 6 and the Oxygen Control Module 8' as described previously until the diver's lungs are full. If a diver is descending during this cycle of breathing the volume of gas in the system is reduced due to hydrostatic compression and the amount of gas inhaled by the user will be less than is required to achieve full lung volume. At this point exhalation counterlung 4 collapses and activates a diluent gas addition valve 13, which automatically provides sufficient gas to allow the user to complete inhalation where upon it ceases to add diluent gas to the system. The diluent gas which is supplied to valve 13 is provided by a pressure vessel 16 containing a supply of a breathable diluent gas. The pressure vessel contains a shutoff valve 17 and a first stage regulator 18 which reduces the pressure to between 8 to 12 bar typically and supplies this gas via tube 15 to the counterlung "Automatic Diluent Valve" or "ADV" 13 which acts as described above. When a user is ascending from depth, the reverse occurs and the user's exhaled lung volume will eventually exceed the combined volumes of counterlungs 4 and 11 and the rise in system pressure will trigger a pressure relief valve 14 that dumps the excess gas overboard. The user may then be free to initiate the next breath.

As is well known to those skilled in the art, there are many variations on the general concept of the CCR architecture 100 and similar breathing apparatus as indicated above, However, the above comprises typical basics features of modern digitally-controlled CCR apparatus and similar breathing apparatus for which the subsequent discussion herein pertain.

Basic Breathing Apparatus—Oxygen Control Arrangement

Figure 2:
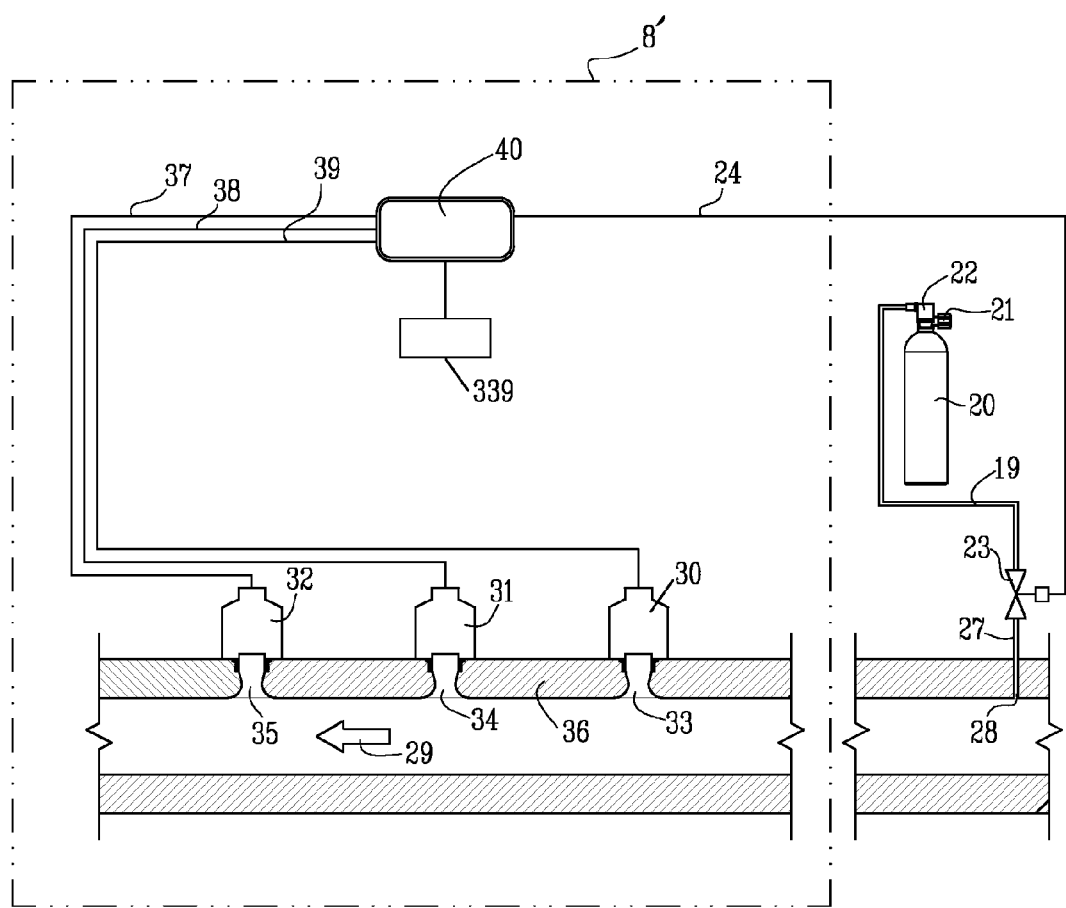
FIG. 2 shows in schematic mode an exemplifying architecture of the Oxygen Control Module 8' of the CCR in FIG. 1.

We now specifically turn our attention to what is inside the Oxygen Control Module 8' of a typical modern CCR as indicated in FIG. 1. For this purpose FIG. 2 provides a schematic architecture that shows a basic internal system including three oxygen sensors 30, 31, and 32 that attach to sensing manifold structure 36 and are exposed to the breathing gas that flows through gas pathway 29 at access ports 33, 34, and 35 respectively. The electrical signals from oxygen sensors 30, 31, and 32 are carried by electrical cables 39, 38, and 37 respectively to a control arrangement preferably a control unit 40 comprising software and/or hardware designed to process and interpret the signals and to provide that information to the decision making software and/or hardware that resides on the control unit 40. The control unit 40 is powered by one or more power means 339 such as a battery or similar that provides portable electrical power to the control unit 40. The control unit 40 can then operate oxygen solenoid valve 23 as needed via cable 24 and provide information to a display 26 via cable 25. The oxygen supply 20 and oxygen solenoid valve 23 are as previously defined in FIG. 1 with the exception that we further clarify that the output from solenoid valve 23 is sent through tube 27, which connects to manifold structure 36 and then is injected into the breathing loop at orifice 28. It is typical in all present-day CCR designs to inject the metabolic makeup oxygen at a point such that:
1) it will not cause the user at any point to directly inhale a slug of pure oxygen, and
2) it will not inject a slug of oxygen directly or near the oxygen sensors because of the risk of temporarily spoofing (confusing) the sensors.

As mentioned above in the section "Background", examples of breathing apparatuses as the one shown in FIG. 2 utilizing three oxygen sensors per se are e.g. disclosed in the patent documents U.S. Pat. No. 6,712,071 (Parker), GB 2404593 (Deas) and CA 2564999 (Straw).

The compromise that is generally reached is to inject metabolic makeup oxygen at the inlet (upstream) manifold for the carbon dioxide removal canister 7 e.g. near or at the hose junction 275 as shown in FIG. 1, such that the oxygen has a chance to mix with the gas flow prior to reaching the oxygen sensors so as to eliminate PO2 spiking of the oxygen sensors. Thus in FIG. 2 the metabolic oxygen injector orifice 28 is shown as being well upstream of the oxygen sensors 30, 31 and 32 with the flow in breathing gas pathway 29 from right to left.

Hence, prior to the disclosure of the present invention the concept of injecting oxygen even in the close proximity of the oxygen sensors would have been considered a bad idea due to the risk of temporarily affecting the oxygen sensors in a negative manner. In fact, the idea of injecting oxygen substantially directly into the oxygen sensor as in the present invention would have been, and will probably be, considered radically incorrect by mainstream CCR designers. Hence, the invention offers a non-obvious path forward to a more reliable, and safe CCR Oxygen Control System.

Additionally, in FIG. 2 all of the oxygen sensor failure scenarios described earlier in the section "Background" are extant and there is no remedy for dealing with these problems during a dive other than to read the displayed sensor values and attempt to make an immediate decision—rightly or wrongly—by human intuition alone whether they represent a life-threatening situation. It is primarily for this reason that electronically controlled CCR systems have been viewed by some as "more dangerous" than open-circuit breathing apparatuses and similar. Below follows a discussion of embodiments of the invention that will eliminate or at least mitigate the ambiguity in this crucial decision making process.

Oxygen Sensor Arrangement—Two Sensors, One Auto-Calibrated/Auto-Validated

Figure 3A:
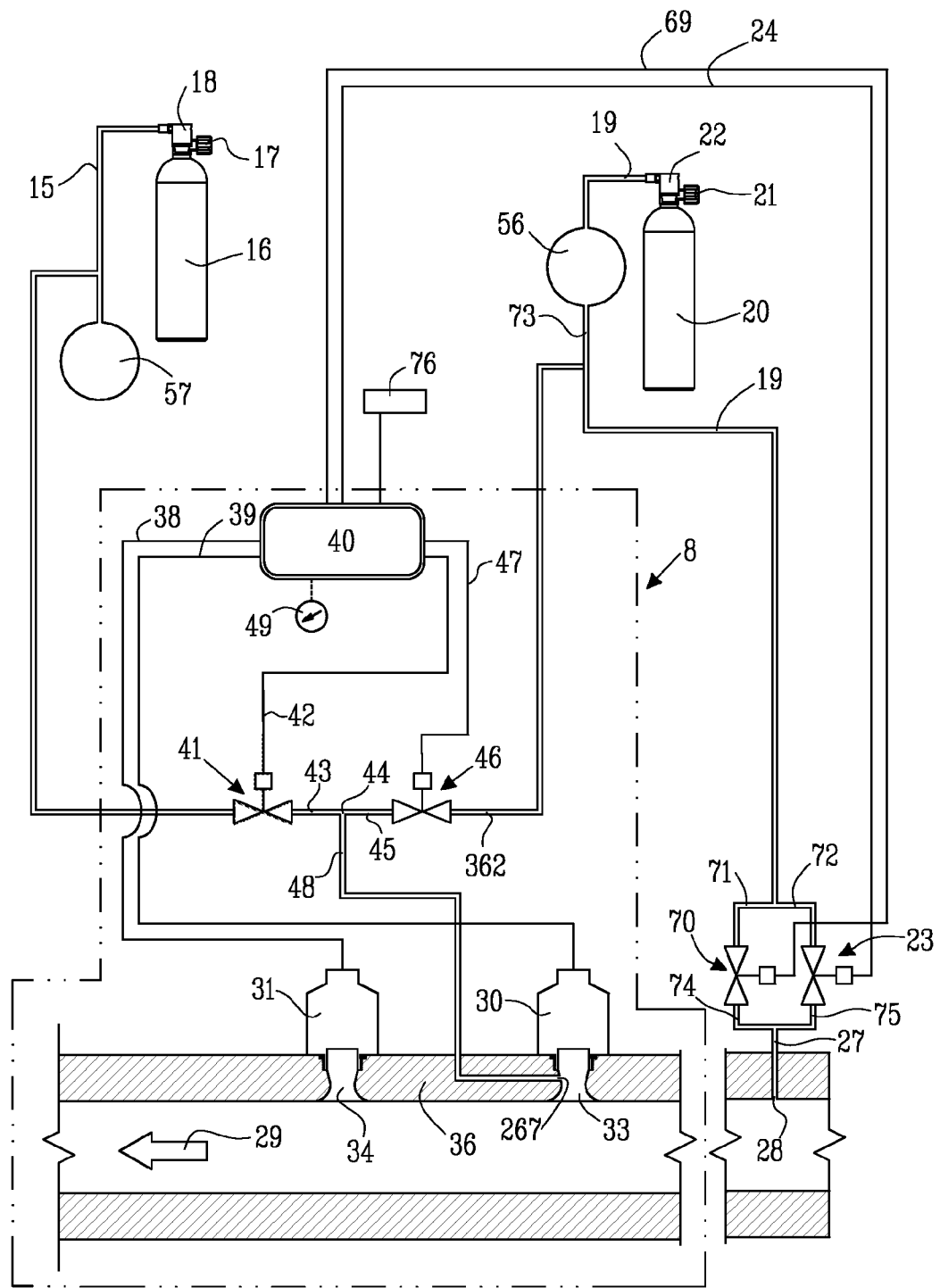
FIG. 3a shows in schematic mode an exemplifying architecture of an Oxygen Sensor Arrangement 8 for a simple embodiment of the invention comprising a Primary Oxygen Sensor and a Secondary Oxygen Sensor.

FIG. 3a shows the schematic architecture for a simple embodiment of the invention, focusing on the Oxygen Sensor Arrangement 8, corresponding to Oxygen Control Module 8' in FIG. 1.

Before we proceed it should be emphasised that the same or similar references in the Figures of the appended drawings correspond to the same or similar features, unless otherwise indicated herein. For example, the oxygen supply 20 is the same in FIGS. 1, 2 and 3a.

As can be seen in FIG. 3a, the Oxygen Sensor Arrangement 8 comprises or is at least connected to a control unit 40 according to an embodiment of the present invention. The control unit 40 is arranged to operatively control and supervise the operation of the Oxygen Sensor Arrangement 8 and the oxygen sensors in particular and the oxygen in the breathing gas in the breathing loop of the CCR 100 in general as indicated by 29' in FIG. 1, i.e. particularly the oxygen in the breathing pathway 29 in FIG. 3a that forms a part of the breathing loop 29' of the CCR 100. The control unit 40 may be implemented by means of hardware and/or software, and it may comprise one or several hardware units and/or software modules, e.g. one or several separate processor arrangements provided with or having access to the appropriate software and hardware required for the functions to be performed by the Oxygen Sensor Arrangement 8. Various programmable oxygen control modules such as module 40 capable of supervising the oxygen sensors in a CCR and the oxygen of the breathing gas in the breathing loop of a CCR are well known per se by those skilled in the art and they need no detailed description as such, see e.g. the patent documents U.S. Pat. No. 6,712,071 (Parker), GB 2404593 (Deas) and CA 2564999 (Straw) mentioned above.

However, the control unit 40 related to embodiments of the present invention comprises novel features that will be elaborated in the following.

The control unit 40 is powered by battery module 76 or a similar power source, which must not necessarily be a part of the Oxygen Sensor Arrangement 8. The ambient pressure is preferably measured by a pressure sensor 49 that transmits the pressure information to control unit 40 so that onboard firmware has, at all times and in real-time, access to the absolute ambient pressure (preferably measured in bars). It should be emphasised that the pressure sensor 49 may be omitted in some embodiments of the invention. This may e.g. be the case in embodiments that are used at a substantially constant pressure, e.g. in breathing apparatuses intended to be used at the surface, e.g. such as medical equipment (e.g. medical ventilators and respirators etc). Primary Oxygen Sensor 30 and Secondary oxygen sensor 31 are connected to the control unit 40 by signal wires 39 and 38, respectively and convey real-time information on the PO2 sensed by each sensor via access ports 33 and 34, respectively in manifold structure 36 such that each sensor is exposed to the breathing gas flow through gas pathway 29.

Control unit 40 in turn separately controls four or more microvalves 23, 70, 46, and 41 via electrical connections 24, 69, 47, and 42 respectively. Oxygen is supplied by pressure vessel 20 which includes a manual shutoff valve 21, first stage regulator 22 and a low pressure (8 to 12 bar) delivery tube 19 that connects to a low pressure accumulator volume 56. From the accumulator volume 56, tubes 73, 19, 71, and 72 transport oxygen to the metabolic makeup microvalves 23 and 70 which are both of a normally-closed design. It is preferred that when the control unit 40 determines that the measured PO2 (following calibration and validation, which we will discuss below) is below the PO2 control setpoint by some pre-set tolerance, tol, (e.g. determined by means of empiric test) a signal is sent to open the primary metabolic oxygen makeup solenoid microvalve 23 such that oxygen is sent through tubes 75 and 27 to the injection port 28 into the gas processing unit 6, see FIG. 1. It is preferred that the injection point 28 is arranged upstream of the carbon dioxide canister 7 and downstream of the breathing hose 5, such that the injected oxygen will be mixed with the breathing gas as it passes through the carbon dioxide absorbent chamber 7 prior to reaching the oxygen sensors 30, 31. As can be seen in FIG. 3a it is further preferred to have a second parallel, normally un-used metabolic makeup oxygen injection microvalve 70 that can be activated when the control unit 40 determines that more metabolic makeup oxygen is needed than is capable of being supplied solely by the primary oxygen microvalve 23 or in the event of a failure in the closed state of microvalve 23.

The oxygen test microvalve 46 connected to oxygen tubes 73 19 via tube 362 is primarily dedicated to automated calibration of the Primary Oxygen Sensor 30. The output of microvalve 46 travels through tube 45 to junction 44, and then via tube 48 to a test orifice 267 from which the output is injected to the access port 33 of the oxygen sensor 30.

It is preferred that the test orifice 267 or similar opening is arranged in a position that is adjacent to or directly adjacent to the Primary Oxygen Sensor 30 so that the distance between the test orifice 267 and the oxygen sensor 30 (preferably the sensing surface of the oxygen sensor or similar part of the oxygen sensor preferably arranged in the access port 33) is less than 150 millimeters (mm), or less than 100 millimeters, or less than 50 millimeters, or less than 25 millimeters, or less than 20 millimeters, or less than 15 millimeters, or less than 10 millimeters, or less than 5 millimeters, or less than 2.5 millimeters, or less than 1 millimeter or less than 0.5 millimeter, but preferably larger than 0.1 millimeter.

It is also preferred that the gas from the test orifice 267 is injected into the access port 33 of the oxygen sensor 30 in such a fashion as to create turbulence that will lift condensation off of the sensing surface of sensor 30 but not cause damage to that surface. At the same time, the surface will thus be exposed to a burst of pure oxygen with a PO2 corresponding to pure oxygen at the ambient pressure sensed by pressure sensor 49.

It is also preferred that the access port 33 of the Primary Oxygen Sensor 30 is implemented as a cavity in the sensing manifold structure 36 enclosing the gas pathway 29 so as to define a test volume that is preferably smaller than 100 milliliters (mL), or smaller than 90 milliliters, or smaller than 80 milliliters, or smaller than 70 milliliters, or smaller than 60 milliliters, or smaller than 40 milliliters, or smaller than 30 milliliters, or smaller than 20 milliliters, or smaller than 10 milliliters or smaller than 5 milliliters, but preferably larger than 1 milliliter, or larger than 2 or larger than 3 milliliters. Consequently it is preferred that the test valves 41, 46 are controlled by the control unit 40 so as to provide an amount of gas to the Primary Oxygen Sensor 30 that corresponds to the volume of the cavity of the access port 33 for the Primary Oxygen Sensor 30, e.g. provide a volume that is substantially equal to or less than the volume of the cavity or twice that volume and hence preferably at least not larger than 200 milliliters.

In a similar manner as the oxygen gas described above, diluent gas is provided to the test orifice 267 and the access port 33 via pressure vessel 16 which includes a manual shut-off valve 17, first stage regulator 18 and a low pressure (8 to 12 bar) delivery tube 15 that connects to a low pressure accumulator volume 57. The purpose of accumulator 57 is to provide a significant volume of low pressure gas adjacent or immediately adjacent the associated diluent test microvalve 41 such that when that valve is commanded to add gas that line pressure loss effects do not prevent the required volume from being injected through the valve 41. From the accumulator 57, tube 15 continues to the diluent test microvalve 41 which is of a normally-closed design. The output of microvalve 41 proceeds through delivery tube 43 to junction 44. From there it proceeds through tube 48 and is injected into the cavity 33 of the Primary Oxygen Sensor 30 at orifice 267, i.e. the same as for the oxygen gas injection described above.

It is also preferred that the control arrangement 40 comprises information or is arranged to operatively receive information corresponding to the fraction of oxygen in the diluent (e.g. air with approximately 21% oxygen) and/or in the oxygen (approximately 100% oxygen), so as to be able to operatively compare said representation with measures from the Primary Oxygen Sensor 30 obtained when the sensor 30 is provided with an amount of gas via the test orifice 267 by means of test valves 41 and/or 46. For example, the control arrangement 40 may be provided with information about the fraction of oxygen in the diluent and/or oxygen in question by the user actuating buttons or similar input means on the Oxygen Sensor Arrangement 8 or on the display unit 26 or similar before a dive. Alternatively, information corresponding to the fraction of oxygen in the diluent and/or oxygen to be used may be provided to the control unit 40 during manufacturing or distribution or similar, or it may be provided by information read from the diluent source and/or oxygen source 20 when these sources are connected to the CCR 100 and the control unit 40, e.g. read by means of electric signals communicating with a memory or similar comprised by the source 16, 20.

Given the exemplifying architecture as outlined above, the oxygen auto-calibration and/or testing method according to embodiments of the invention provide a series of particularly advantageous capabilities as will be further elaborated below.

True Automated Pre-Dive Calibration

Referring again to FIG. 3a, at initial power-up at the surface before use of the CCR 100 according to an embodiment of the present invention, control unit 40 will automatically fire the diluent test microvalve 41 to inject a burst of pure diluent gas (e.g., air) substantially directly on the Primary Oxygen Sensor 30, reliably exposing it to a known low-oxygen mixture at the ambient pressure. The output signal from oxygen sensor 30 is then stored by the control unit 40 (preferably in a non-volatile memory) as a first oxygen calibration point. Next, control unit 40 will automatically fire the oxygen test microvalve 46 to inject a burst of pure oxygen directly on the Primary Oxygen Sensor 30, reliably exposing it to pure oxygen at the ambient pressure. The output signal from sensor 30 is then stored by the control unit 40 (preferably in a non-volatile memory) as a second oxygen calibration point. In actual practice, it is preferred that a plurality of readings (e.g. at least 10 readings) are made at each calibration point and the results averaged. In both cases (diluent and oxygen injection) the ambient pressure is preferably measured via pressure sensor 49. The ambient pressure (absolute), combined with the known decimal fractional content of oxygen (FO2) in both the diluent (at 1 bar at the surface, air, for example, would have an FO2 of 0.21) and the pure oxygen supply (FO2=1.0), allows for the direct calculation of the PO2 at the two calibration points from which a linear or at least substantially linear calibration curve (see FIG. 3d and/or FIG. 3f) can be automatically generated and stored by the control unit 40 (preferably in a non-volatile memory). It is preferred that this stored curve that will be used throughout a dive for the determination of metabolic oxygen makeup gas injection, unless one of the trigger events listed below occurs first.

Figure 3B:
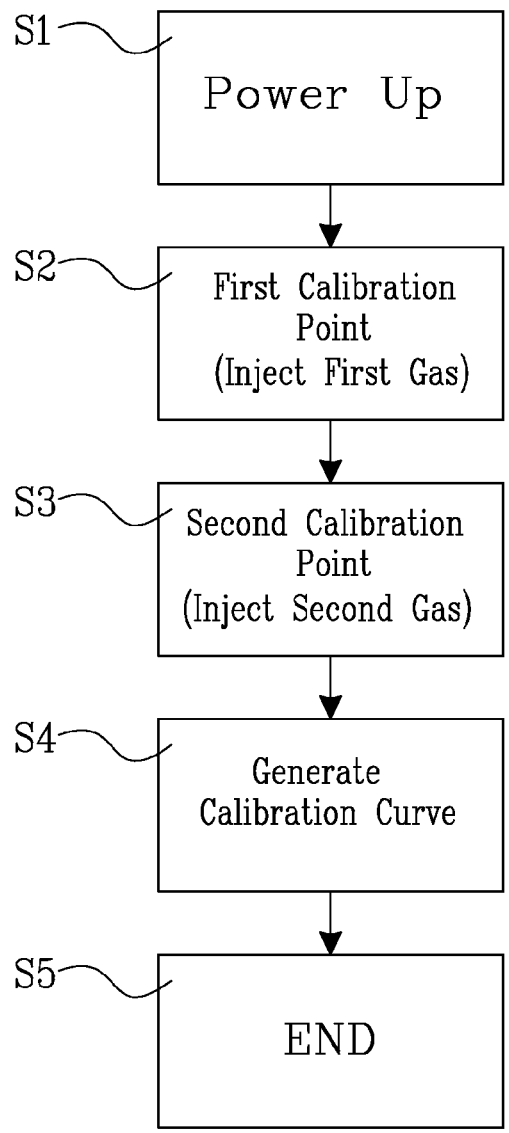
FIG. 3b shows an exemplifying pre-dive calibration according to an embodiment of the present invention.
Figure 3C:
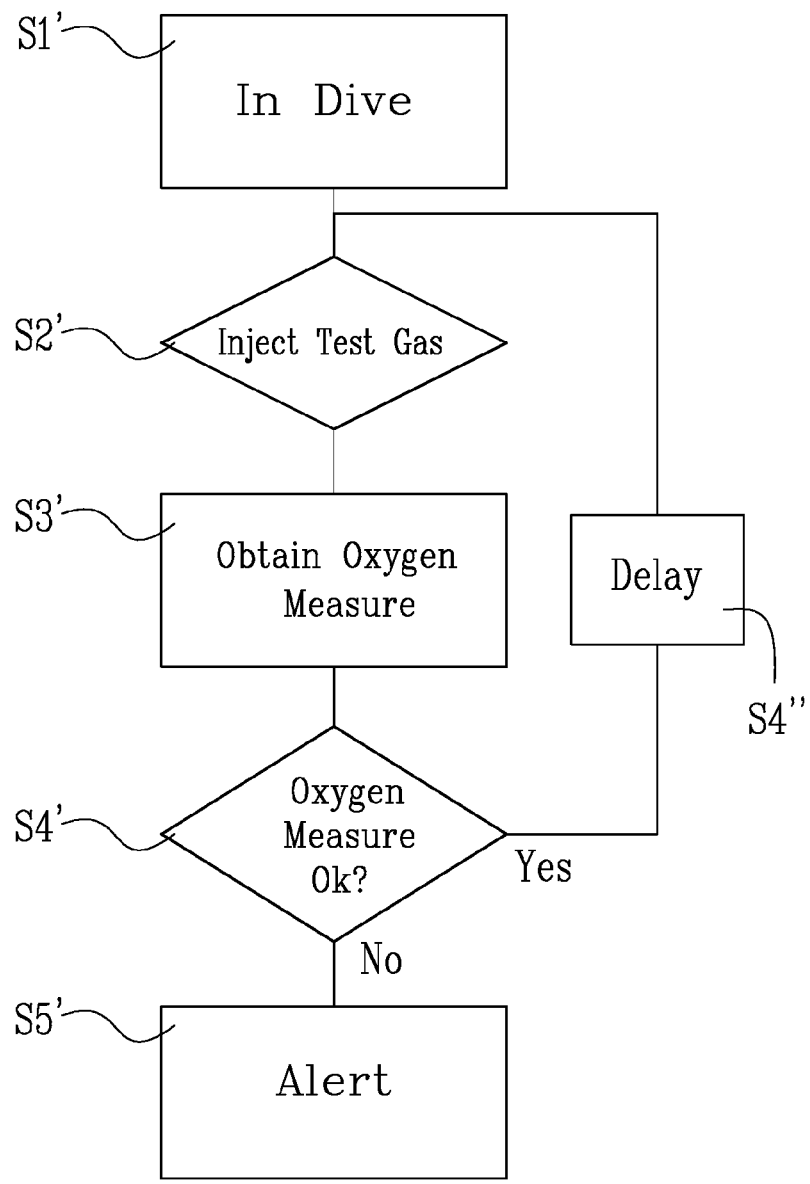
FIG. 3c shows an exemplifying in-dive validation according to an embodiment of the present invention.

FIG. 3b shows an exemplifying pre-dive calibration according to an embodiment of the present invention as indicated above.

In a first step S1 it is preferred that the CCR 100 and the control unit 40 are powered up. This step may e.g. include diagnostic activities and other start up routines.

In a second step S2, the system will start a calibration of the Primary Oxygen Sensor 30 by automatically injecting a burst of pure diluent gas (e.g., air) substantially directly on the Primary Oxygen Sensor 30, reliably exposing it to a known low-oxygen mixture. This is accomplished by the control unit 40 actuating the diluent test valve 41 in FIG. 3a. Here, it is also preferably that the ambient pressure is measured by the pressure sensor 49. This is preferably done just before or during the injection of diluent gas. It is preferred that the output signal from the oxygen sensor 30 and the pressure sensor 49 or representations thereof are stored by the control unit 40 as a first oxygen calibration point. The same applies mutatis mutandis for diluent test valves 352, 353, 354, 368 as will be clearly understood by later discussions referring to FIGS. 13, 14, 15, 16, 17, 24, 25, 26, 27 and 28.

In a third step S3, the system will automatically inject a burst of pure oxygen gas substantially directly on the Primary Oxygen Sensor 30, reliably exposing it to pure oxygen. This is accomplished by the control unit 40 actuating the oxygen test valve 46 in FIG. 3a. Optionally the ambient pressure may be measured again by the pressure sensor 49, just before or during the injection of oxygen gas. It is preferred that the output signal from the oxygen sensor 30 and the pressure sensor 49 or representations thereof are stored by the control unit 40 as a second oxygen calibration point. The same applies mutatis mutandis for oxygen test valves 355, 356, 357, 372 as will be clearly understood by later discussions referring to FIGS. 13, 14, 15, 16, 17, 24, 25, 26, 27 and 28.

Figure 3D:
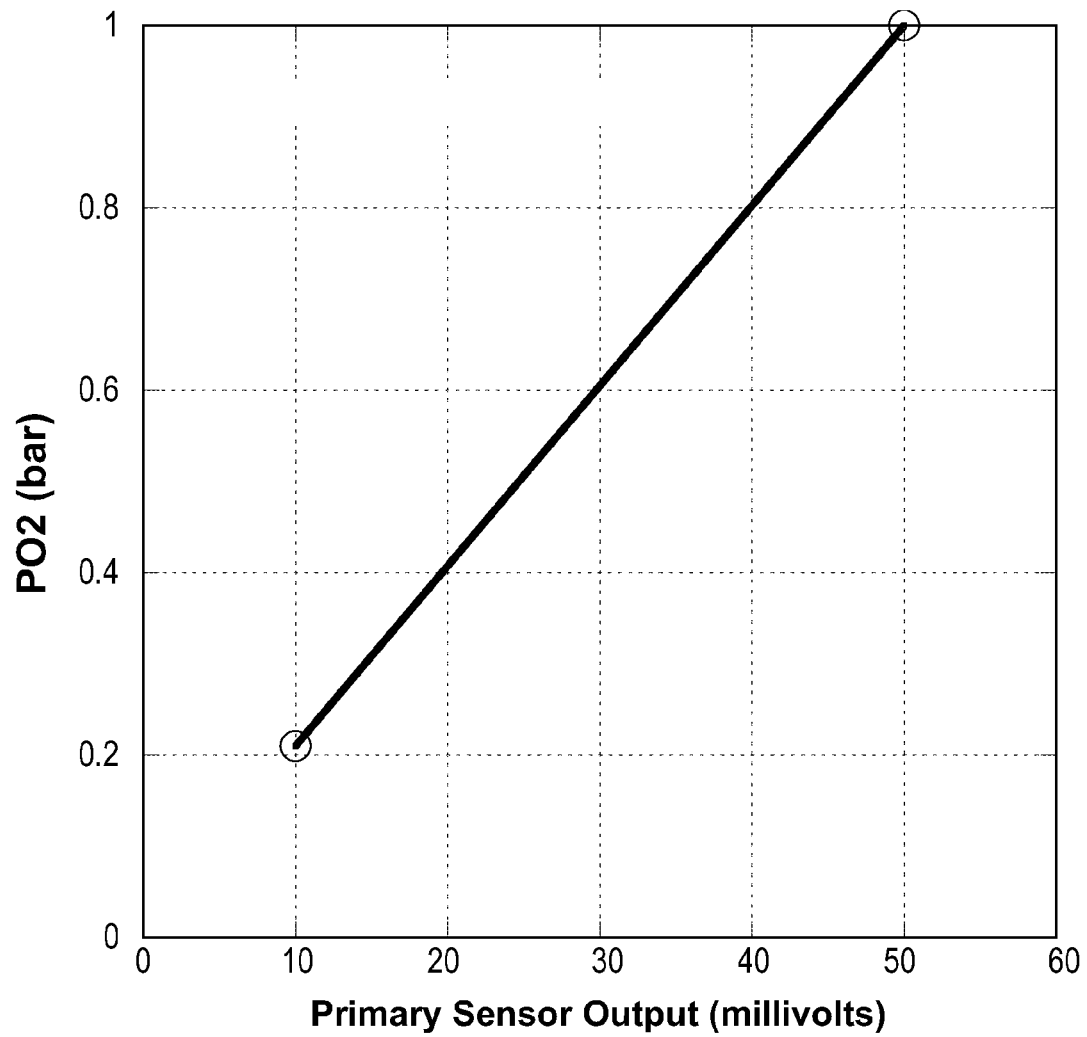
FIG. 3d shows an exemplifying substantially linear 2-point calibration curve.

In a fourth step S4 it is preferred that the system (preferably the control unit 40) calculates a calibration curve based on the two oxygen calibration points obtained in step S2 and S3, see FIG. 3d. This is preferably accomplished by calculating the PO2 at the two oxygen calibration points, which can be done in a well known manner by utilising the measures from the oxygen sensor 30 and the pressure sensor 49. The two oxygen calibration points are then preferably used to generate a linear or at least substantially linear calibration curve, which is preferably stored by the control unit 40.

The pre dive calibration ends in a fifth step S5. The fifth step S5 may check whether the calibration was successful or not. For example, it may be checked whether the two calibration points obtained in step S2 and S3 respectively are reasonable. For example, the first calibration point should produce a PO2 near 0.21 if air is used and the second calibration point should produce a PO2 near 1.0 if oxygen is used. If this is not the case an abortion notification may be produced by the control unit 40.

In-Dive Sensor Validation and Condensate Purging with Diluent Gas

Referring again to FIG. 3a, periodically during the course of a dive (possibly more often than every 30 second, or more often than every minute, or more often than every two minutes, or more often than every three minutes, or more often than every four minutes, or more often than every five minutes, but generally on a 5 to 10 minute interval, although this value can be stored by the control unit 40 (preferably in a non-volatile memory) as a user-definable constant) the control unit 40 will cause diluent test microvalve 41 to fire and thus inject a small burst of diluent gas into the oxygen sensor cavity 33 via injection orifice 267. This burst of diluent gas will have the previously described primary effects of automatically removing condensate from the sensing surface of Primary Oxygen Sensor 30 and simultaneously exposing the sensing surface to a gas mixture with a fixed FO2 (decimal fraction of oxygen). The control unit 40 will then obtain the resultant PO2 reading from Primary Oxygen Sensor 30 and obtain the current ambient pressure from the pressure sensor 49. With the ambient pressure sensor 49 and a known oxygen fraction (FO2) in the diluent supply 16, the Primary Oxygen Sensor 30 can be exposed to a known partial pressure of oxygen (PO2) at any moment during the dive, and monitored to ensure that the sensor responds with the correct reading. The correct reading is simply the absolute ambient pressure (in bar) times the known FO2 of the diluent. Repeated failure of this test will cause the control unit 40 to initiate an alert to the diver that the dive should be aborted immediately. The alert can be issued by means of any safety system well known to those skilled in the art as being commonly used in CCRs, including but not limited to visual and/or audible signalling.

FIG. 3c shows an exemplifying in-dive validation according to an embodiment of the present invention as indicated above.

In a first step S1' according to the present embodiment it is preferred that the CCR 100 and the control unit 40 are active. The CCR may e.g. be active under water or otherwise active at an ambient pressure above 1 bar. However, other embodiments of the invention may certainly be active at other pressures, e.g. embodiments of the invention implemented in breathing apparatuses that are active at the surface at an ambient pressure of substantially 1 bar.

In a second step S2', the system will start a validation of the Primary Oxygen Sensor 30 by automatically injecting a burst of pure diluent gas (e.g., air) substantially directly on the Primary Oxygen Sensor 30, reliably exposing it to a known low-oxygen mixture. This is accomplished by the control unit 40 actuating the diluent test valve 41 in FIG. 3a.

Figure 3E:
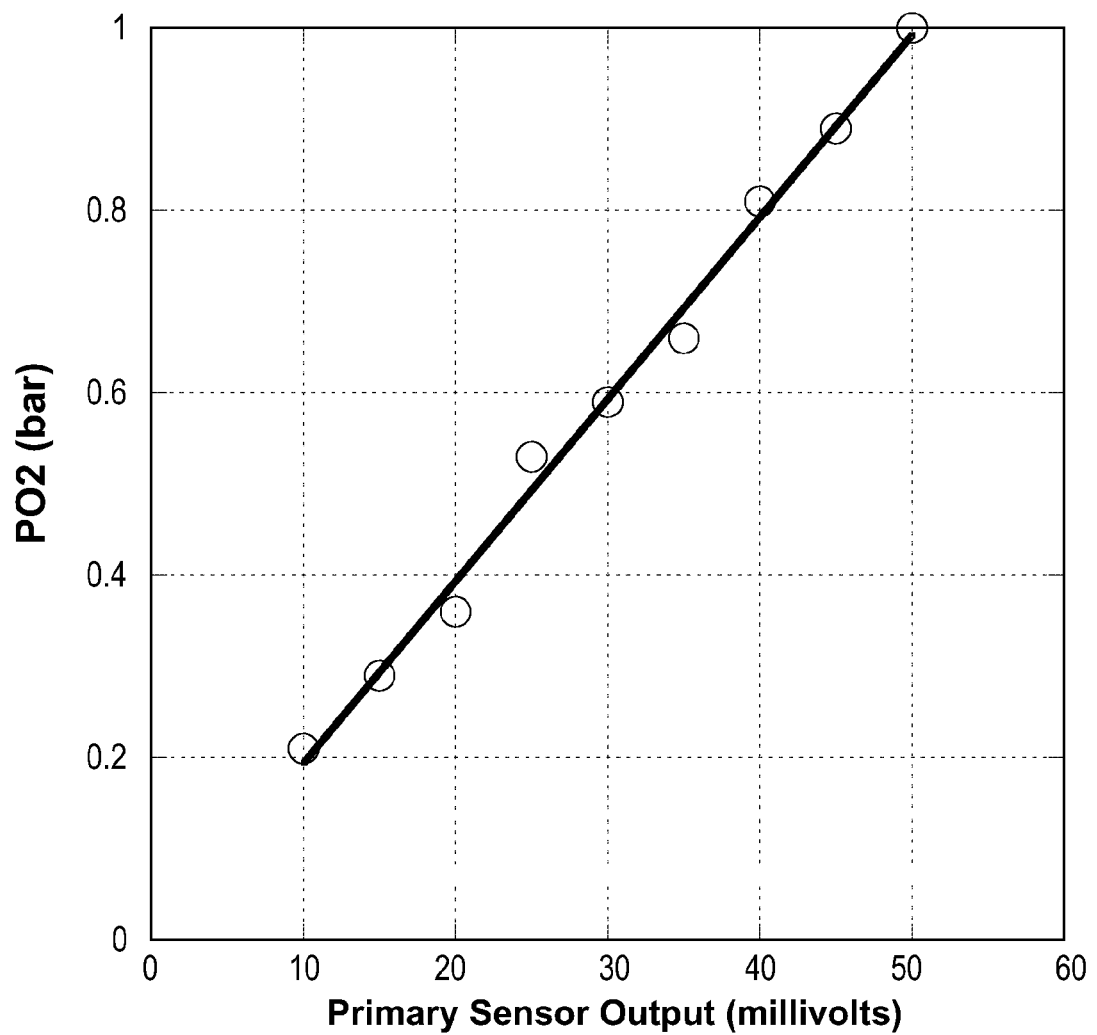
FIG. 3e shows an exemplifying number of validation points.
Figure 3F:
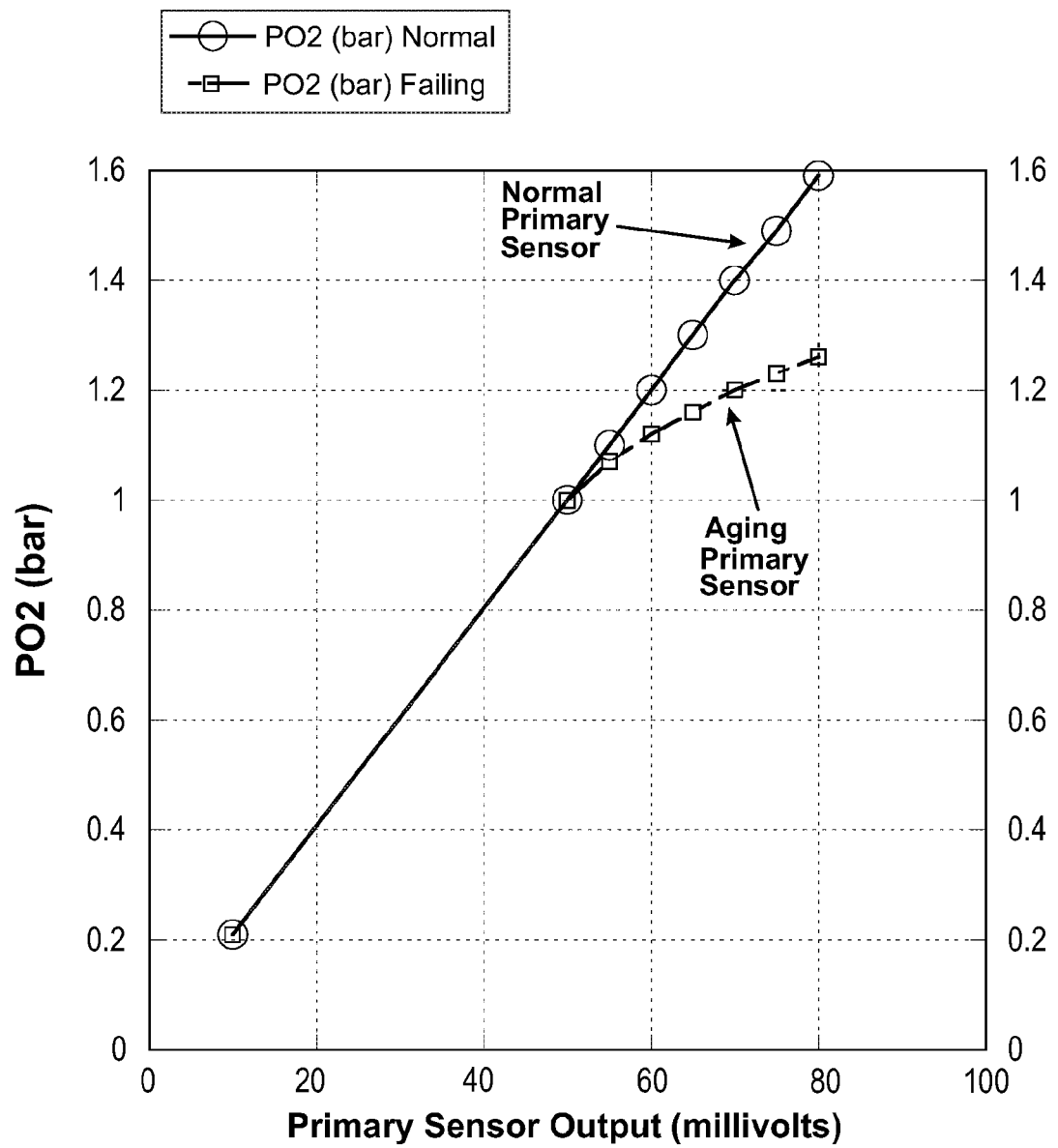
FIG. 3f shows an exemplifying substantially linear calibration curve based on 3 or more calibration points.

In a third step S3' during the exposure of the Primary Oxygen Sensor 30 a measure is obtained from the oxygen sensor 30 and from the pressure sensor 49. The pressure is preferably measured just before or during the injection of diluent gas. At each such occasion it is preferred that the output signal from the oxygen sensor 30 and the pressure sensor 49 or representations thereof are stored by the control unit 40 as validation points, see the circles in FIG. 3e. The procedure described for diluent test valve 41 applies mutatis mutandis for diluent test valves 352, 353, 354, 368 as will be clearly understood by later discussions referring to FIGS. 13, 14, 15, 16, 17, 24, 25, 26, 27 and 28.

In a fourth step S4' it is preferred that the system (preferably the control unit 40) calculates the expected PO2 for the validation point using the known fraction of O2 in the diluent and the current ambient pressure obtained from the pressure sensor 49. The expected value for the validation point value is preferably calculated by using the calibration curve so as to compensate for possible acceptable deviations in the Primary Oxygen sensor 30. The expected PO2 is then compared to the measure obtained from the Primary Oxygen Sensor 30.

The validation process proceeds to a fifth step S5 if the difference between the expected PO2 and the measure obtained from the Primary Oxygen Sensor 30 exceeds a predetermined threshold and an alert is issued. The threshold may e.g. be determined by means of empirical investigations.

The validation process proceed to delay step 4" if the difference between the expected PO2 and the measure obtained from the Primary Oxygen Sensor 30 is at or below the predetermined threshold and the process is stayed for a predetermined time before returning to the second step S2' to inject another burst of diluent gas on the Primary Oxygen Sensor 30. The predetermined time may e.g. be determined by means of empirical investigations. For example, it may correspond to a validation interval of less than 30 second, less than a minute, less than two minutes, less than three minutes, less than four minutes, less than five minutes, but generally less than a 5 to 10 minute interval.

During the time of the automated testing procedure described above it is preferred that the control unit 40 disables firing of the metabolic oxygen microvalves 23 and 70 and continues to prevent firing after termination of the test for a period necessary to flush the access port 33 of the Primary Oxygen Sensor 30 with uniform breathing gas from the user. This duration is design specific but in general will be approximately 8 to 10 seconds following the termination of the gas pulse entering the sensing cavity 33.

A Secondary Oxygen Sensor

The Secondary Oxygen Sensor 31 and access port 34 are preferably the same or similar as the Primary Oxygen Sensor 30 and access port 33. However, the access port 34 of the Secondary Oxygen Sensor 32 shown in FIG. 3a is not provided with a test orifice such as the test orifice 267 in the access port 33. The access port 34 may therefore have a shape that differs from the shape of access port 33. The primary function of the Secondary Oxygen Sensor 31 is that of auxiliary verification of the functional state of the Primary Oxygen Sensor 30 and cross-correlation that there are no leaks in either of the test microvalves 41 and 46. The Secondary Oxygen Sensor 31 is thus an aid to making the go/no-go (abort/continue) decision that is made primarily based on the PO2 measured by the Primary Oxygen Sensor 30. Hence it is preferred that the Secondary Oxygen Sensor 31 monitors the oxygen content of the breathing gas while the Primary Oxygen Sensor 30 is being validated. It is also preferred that the Secondary Sensor 31 is used to detect possible leakage in the test valves 41 and/or 46 as described in more detail below. However, already here it should be mentioned that leakage detection using two primary oxygen sensors would require at least one extra test valve in addition to the test valves 41 and 46. In addition, it is possible to supply a more extensive injection of diluent via the test orifice 267 into the access port 33 of the Primary Oxygen Sensor 30 so that the injected diluent flows out of the access port 33 and into the access port 34 and the Secondary Oxygen Sensor 31. An advisory warning message or an abort message can be issued if the Secondary Oxygen Sensor 31 provides a good PO2 value while the Primary Oxygen Sensor 30 provides a bad PO2 value, or if both the Secondary Oxygen Sensor 31 and the Primary Oxygen Sensor 30 provides a bad PO2 value.

In-Dive Sensor Calibration and Validation with Oxygen

When conducting an oxygen sensor calibration at sea level standard temperature and pressure (STP) it is only possible to obtain a maximum sensor response of 1 bar PO2 from a sensor when exposed to pure oxygen. Obtaining any higher PO2 reading requires the presence of an ambient absolute pressure greater than 1 bar. However, it is also known that a very common class of chemical (fuel cell) type oxygen sensors that comprise the vast majority of all oxygen sensors used in CCR breathing apparatus are subject to degradation in performance above 1 bar PO2 with aging (see FIG. 3f). The aging degradation manifests itself as a departure from an extended calibration curve obtained as will be described below. Current CCR designs have no means of detecting such aging effects.

Referring again to FIG. 3a, during the descent on a dive (after the surface pre-dive calibration has been performed and the diver has begun a descent underwater) and at a point preferably greater than or equal to 5 meters deep (approximately 1.5 bar) but preferably not deeper than 10 meters (approximately 2.0 bar), and preferably following a successful diluent gas PO2 validation check, the control unit 40 will issue a command to fire the Oxygen Test Valve 46 and inject a small volume of pure oxygen into sensing cavity 33 via jet orifice 267. In other words, an additional calibration point is obtained by the control unit 40 actuating Test Valve 46 at least once to provide an amount of pure oxygen to the oxygen sensor 30 while the ambient pressure is in the interval of approximately 1.5 bar to 2.0 bar, preferably measured by the pressure sensor 49. Knowing the FO2 fraction is 1.0 for oxygen and knowing the ambient absolute pressure from sensor 49 the control unit 40 will preferably calculate the true PO2 and store that value (preferably in a non-volatile memory). Given the above, the control unit 40 will obtain an extended calibration curve, see FIG. 3f. The extended calibration curve is preferably based on the two calibration points previously obtained during surface pressure at the pre-dive calibration and at least the third calibration point now obtained under underwater pressure during dive, e.g. obtained at substantially 1,6 bar or points obtained during a number of pressures between substantially 1 bar to substantially 1,6 bar). Preferably the curve fit is accomplished by a non-linear 3-point least squares optimized curve fit. The extended calibration curve is preferably stored by the control unit 40 (preferably in a non-volatile memory), preferably together with the new extended calibration curve coefficients (linear, parabolic, or cubic depending on the best closed-form fit). This extended range calibration and/or check need only be done one per dive and the results will be compared against previous results logged in non-volatile memory and the trends analyzed. A sensor rejection algorithm analyzes the data and determines whether the latest extended range calibration is within allowable specification. If not, the firmware will issue safety advisory warnings to the diver.

It is generally not recommended to exceed an operating PO2 of 1.6 bar in a CCR for reasons of user safety and avoidance of oxygen toxicity effects. Thus the procedure just described would be executed only briefly at one or a few key points between the absolute ambient pressure of 1.0 to 1.6 bar (approximately sea level on the surface to about 6 meters depth underwater). If we were to acquire such points at $1/10^{th}$ bar increments in absolute ambient pressure during a diving descent from the surface to 6 meters depth, we might obtain the data represented by the circles in FIG. 3f for a properly functioning, new oxygen sensor. If the sensor was old, we might see the type of data represented by the square data points in FIG. 3f.

During the time of the automated testing procedure described above it is preferred that the control unit 40 disables firing of the metabolic oxygen microvalves 23 and 70. It is even more preferred that the control unit 40 continues to prevent firing after termination of a dive test for a period necessary to flush the primary oxygen sensing cavity 33 with uniform breathing gas from the user. This duration is design specific but in general will be approximately 8 to 10 seconds following the termination of the calibration gas pulse entering the sensing cavity.

In-Dive Diluent Injection Capability for PO2 Reduction

Unlike the diluent purge sensor test function defined above, there can be times during a dive profile when the true PO2 (returned from the validated Primary Oxygen Sensor 30) will unavoidably exceed a user-defined (within allowable absolute limits) PO2 level. Allowable absolute limits can e.g. be determined by means of empiric tests. One example of how this might occur would be where a user with a low metabolic oxygen consumption rate makes a rapid descent. In such a situation the rate of increase in PO2 due to the increase in hydrostatic pressure (ambient pressure) exceeds the rate of decrease in PO2 due to low metabolism. In such a situation the PO2 will continue to build until it reaches into the zone of oxygen toxicity. In prior CCR systems known to the inventors there was nothing that could be done about this except to manually intervene, flush the system with diluent, and re-stabilize the automated control system. The generally accepted maximum continuous PO2 level for CCR breathing has been set at 1.4 bar absolute. It is also generally accepted that one can exceed this value to as high as 1.9 bar PO2 for short periods of time. Any value higher than that is considered unacceptable and grounds for an aborted dive should it not be able to be quickly remedied. Hence, in an embodiment of the present invention, it is preferred that to define a maximum PO2 threshold value between 1.6 and 1.9 bar prior to the dive. The threshold value is preferably stored in the control unit 40, preferably in a non-volatile memory. During the actual dive, should the true PO2 exceed this maximum threshold control unit 40 will activate diluent microvalve 41 so as to add a measured quantity of diluent into the system via the test orifice 267. It is also preferred that the emergency diluent addition algorithm (for reduction of dangerously high PO2) tracks the ambient pressure via sensor 49 while furthermore computing the rate of descent, computing the rate of PO2 increase, and thence estimating the volume of diluent that needs to be added in order to reduce the current true PO2 to a PO2 value that is at or below the user-defined maximum allowable PO2 threshold as described above.

During the time the automated diluent purge procedure described above is active the control unit 40 disables firing of the metabolic oxygen microvalves 23 and 70 and will continue to prevent firing after termination of the purge for a period necessary to flush the sensing cavity 33 of the Primary Oxygen Sensor 30 with uniform breathing gas from the user. This duration is design specific but in general will be approximately 8 to 10 seconds following the termination of the purge gas pulse entering the sensing cavity.

Three Sensor System, Two Auto-Calibrated/Auto-Validated Sensors

The architecture described above with reference to FIG. 3a is specifically tailored to a "sport" class CCR in which the certainty of detection of the true PO2 is very high because of the just-described ability to auto-calibrate the system (both on the surface and, as well, to extend the calibration curve to high PO2 zones not reachable on the surface) and to auto-verify the PO2 during the course of a dive. However, a system using the control architecture shown in FIG. 3a is not truly redundant and a failure of the single Primary Oxygen Sensor 30 to deliver the anticipated value during a dive is grounds for an abort to the surface, preferably using an alternate life support system. Typically this is provided by the diver carrying a secondary open circuit "bailout" system that will get them to the surface, and it is assumed that a direct abort-to-surface ascent is possible—that is, technical diving inside sunken ships, inside caves, or any diving involving required decompression should preferably not be a part of the dive plan. While FIG. 3a shows a Secondary Oxygen Sensor 31 this secondary sensor does not constitute a truly redundant backup PO2 measurement system. The role of the secondary sensor 32, as stated earlier, is that of auxiliary verification of the functional state of the Primary Oxygen Sensor and cross-correlation that there are no leaks in either of the auto-calibration microvalves. The secondary oxygen sensor 31 is thus an aid to making the go/no-go (abort/continue) decision that is made primarily based on the PO2 measured by the Primary Oxygen Sensor 30. For the purposes of purely recreational CCR diving (defined as having a direct abort-to-surface ability at any time during a dive) this architecture is compact, safe, and adequate for the purpose.

In the figures that follow we address in detail a more advanced level of capability seeking true redundancy in the design of the CCR oxygen control system as it applies to the acquisition of PO2 in the breathing gas.

Before we proceed it will be instructive to define two distinctly different failure categories affecting life support system design: system failure and mission failure.

A system failure is one in which the failure of any critical path component leads to the complete failure of the system and, in the case of a life support system, the death of the user unless some abort mechanism is provided (as, for example, the above-mentioned open circuit bailout device).

A mission failure, by contrast, means that some key element of a system has failed, but a similar (duplicate) system exists that would permit the use of the device to continue as normal except for the fact that the user is now aware that part of the system has failed (degraded) and that prudence dictates a graceful exit from the present circumstances, negating the possibility of continuing the original "mission". It is an important distinction that the "graceful" exit can be achieved using the normal functionality of the device. Re-stated more specifically, in a CCR it means that the abort can be made in closed-cycle mode without resort to an external bailout system.

Summarizing the above, a mission failure is only possible in a truly redundant system. A system failure, in contrast, occurs after all redundant avenues of operation have been exhausted. Earlier the section "Background" explained the fallacy of claimed redundancy in CCR systems that use three oxygen sensors without the possibility of independent validation prior to and especially during a dive. Where true PO2 validation (as previously described in this disclosure) is available, true PO2 sensing redundancy level is defined as follows:
Non-redundant: one real-time validated oxygen sensor. Failure of sensor validation means that the dive must be aborted on an external bailout system.
Duplex redundant: two real-time independently validated oxygen sensors. Failure of one sensor to pass the validation test leads to an advisory to the user, but the system will permit fully closed operation to continue by using the validated second sensor for system PO2 active control. Subsequent failure of the second sensor to validate means that the dive must be aborted on an external bailout system.
Triplex redundant: three real-time independently validated oxygen sensors. Similar to duplex redundancy except that three sensors must all fail before the dive must be aborted on an external bailout system.

There are important nuances that factor on the independence and isolation of these systems in achieving true redundancy, and the relative importance of these nuances (design features) can only be quantitatively assessed through statistical network failure (e.g. fault tree) analysis. Thus, there is no absolute "non-redundant", "duplex redundant", and "triplex redundant" design, only a series of designs that can be evaluated as indicating the enhanced reduction of failure probability. The measure of these enhancements will add fractionally to the improvement of overall survival probability and at some point, depending on the specific application, the probability of a system failure will be determined to be sufficiently low to safely operate in that environment. The means by which independence and isolation in the measurements can be achieved in a CCR will become clear below.

Figure 4:
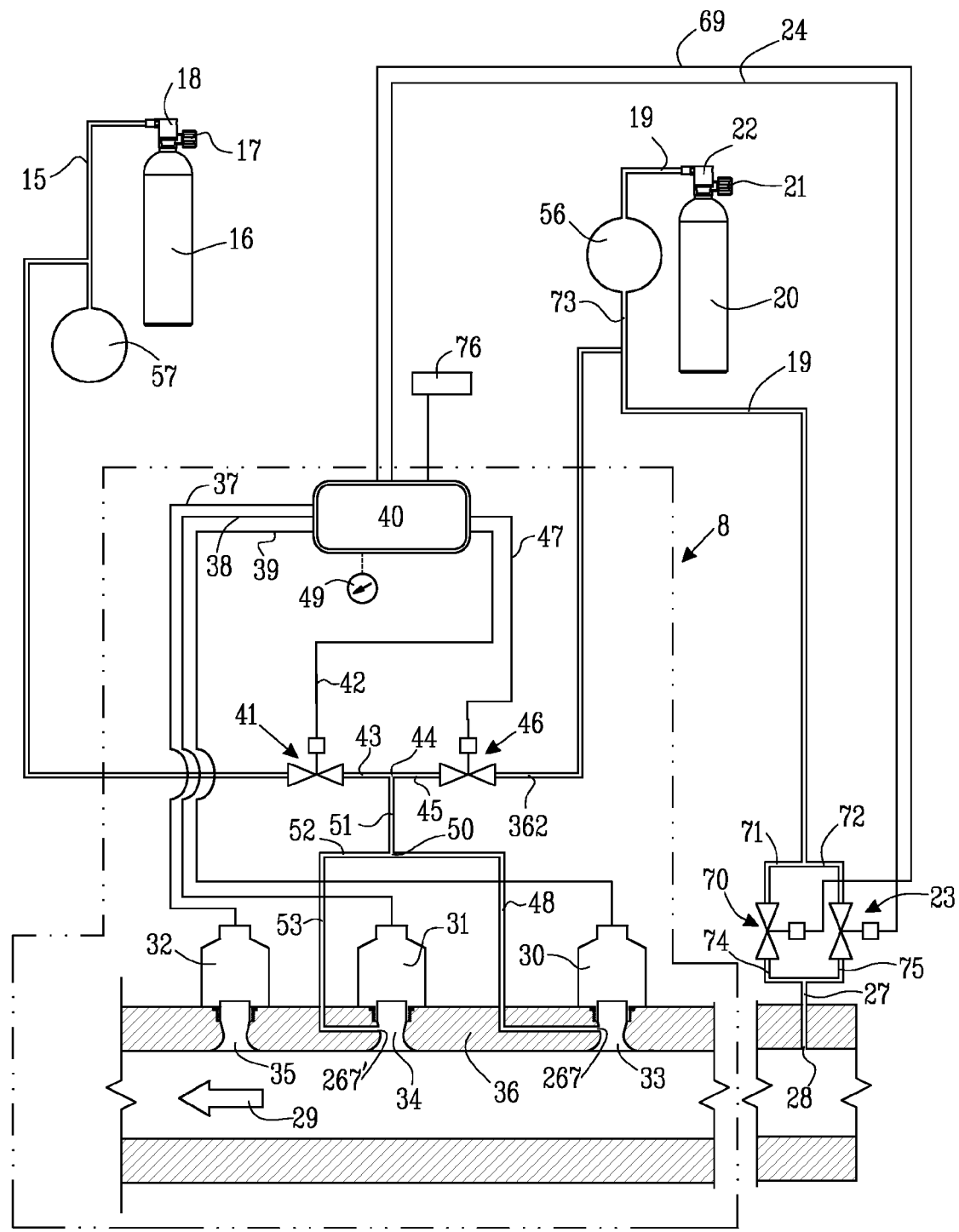
FIG. 4 shows a design that is substantially identical to the one described in FIG. 3a but with three sensors—two auto-calibrated.

FIG. 4 shows a CCR design that is substantially identical to the one described in FIG. 3a, but with the following changes:

a third oxygen sensor 32 mounted on manifold structure 36 with access port 35 to the breathing loop 29 has been added. The Third Oxygen Sensor 32 and access port 35 are the same or similar as the Primary Oxygen Sensor 30 and access port 33 previously discussed with reference to FIG. 3a. Sensor 32 is electrically connected to the control unit 40 via electrical cable 37. Sensor 32 is not subjected to an active calibration and/or validation and it assumes the role of the "Secondary" oxygen sensor.

Oxygen sensor 31, being connected to the control unit 40, is now treated by the control unit 40 as a redundant (parallel) Primary oxygen sensor being identical or substantially identical to sensor 30 in function and form.

The gas outputs from the Diluent Test Valve 41 and Oxygen Test Valve 46 that join at junction 44 as previously described now travel through tube 51 to junction 50 whereupon tube 48, as previously in FIG. 3a, conducts diluent and oxygen to sensor 30. In addition, now, tube 52 and 53 conducts diluent and oxygen to sensor 31 from junction 50 to a test orifice 267' being the same or similar as test orifice 267 for sensor 30.

In this design both auto-calibrated and/or auto-validated oxygen sensors 30 and 31 are fed by the same gas distribution pathways ("tubes" 43, 45, 51) from the separate gas sources 16 and 20, respectively diluent and oxygen. A persistent leak in either the diluent test microvalve 41 or the oxygen test microvalve 46 will spoof (confuse) the readings on both sensors 30 and 31. However, sensor 32, because it is not connected to any of the gas sources 16 or 20, serves to detect such leaks through analysis by the control unit 40 of the data streams from the sensors 30, 31, 32. In the absence of an open-state failure in the normally-closed microvalves 41 and 46 both sensors 30 and 31 are subject to both the auto-calibration and auto-validation procedures described above and as such, the firmware operating on control unit 40 could directly detect that one of either sensors 30 or 31 did not pass a particular test but that the other did. If this situation occurred during the course of a dive then the onboard PO2 control system would cease to use both sensors 30 and 31 for the basis of PO2 control and revert to using the one that passed the particular test. Note, however, that because sensors 30 and 31 are not independently isolated from the potential failure of microvalves 41 or 46, the design of FIG. 4 is not precisely a duplex redundant design. It is, however, clearly more survivable than the design of FIG. 3a because it can solve the common problem of asymmetric condensate formation on oxygen sensors and validate the operational sensors, of which there are now two chances for delivering validated data instead of one.

Three Sensor System, Three Auto-Calibrated/Auto-Validated, No Sensor Isolation

Figure 5:
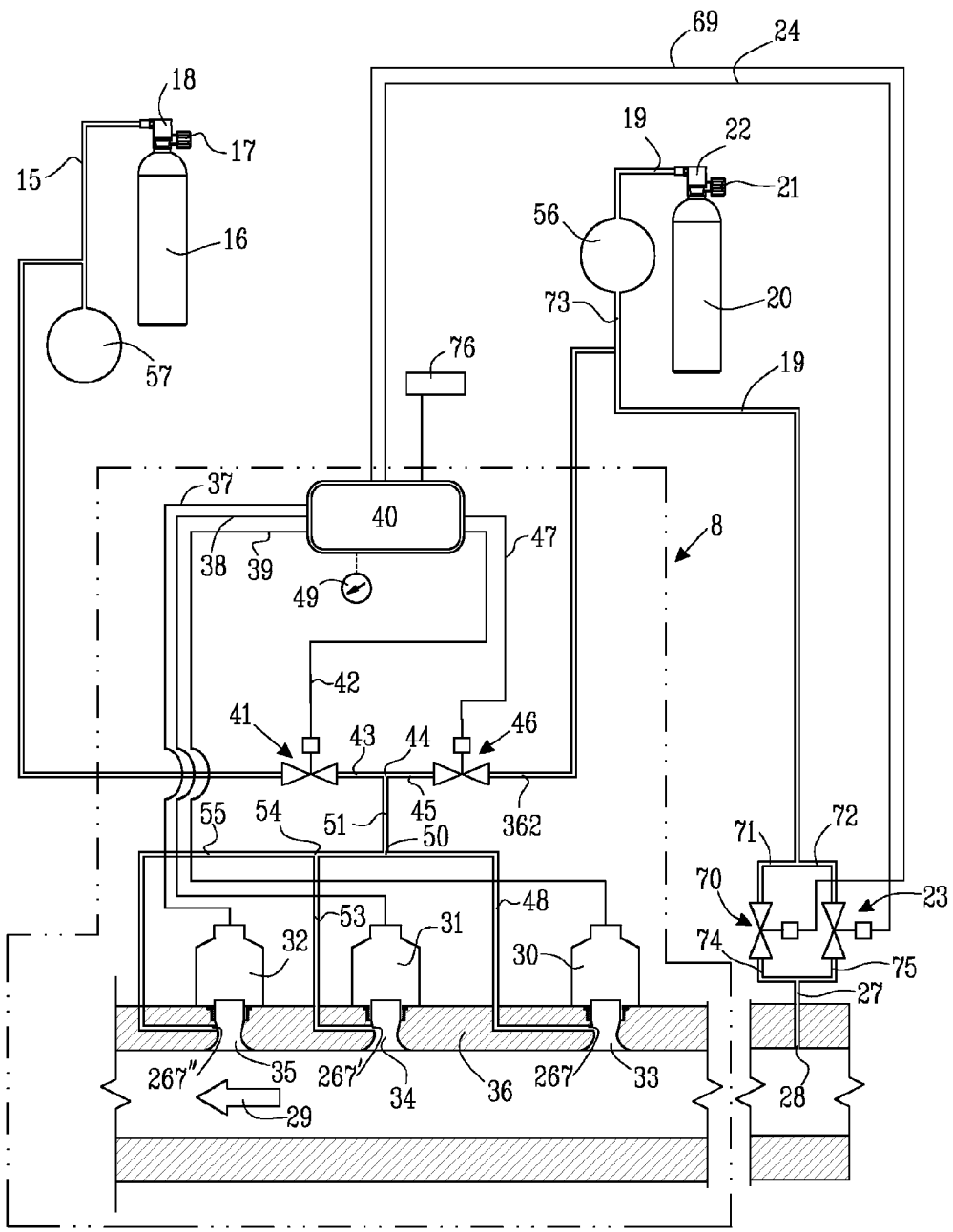
FIG. 5 shows a design that is substantially identical to the one in FIG. 4 but with all three sensors auto-calibrated.

In FIG. 5 we show the same system as in FIG. 4, but with all three oxygen sensors 30, 31, and 32 being connected to the control unit 40 and now treated by the control unit 40 in the same or substantially same manner so as to be redundant (parallel) Primary Oxygen Sensors. The gas outputs from the Diluent Test Valve 41 and Oxygen Test Valve 46 join at junction 44 and travels through tube 51 to junction 50 as previously described. From there, tube 48, as previously in FIGS. 3a and 4, conducts diluent and oxygen to sensor 30, whereas tube 52 and 53 conducts diluent and oxygen to sensor 31 from junction 50. In addition, now, tube 55 conducts diluent and oxygen to sensor 32 from junction 50 to a test orifice 267" being the same or similar as test orifices 267, 267', for sensor 30 and 31 respectively.

Although this system can be built it is less preferred. Under normal operating circumstances this system could discriminate amongst all three sensors because each could be auto-validated for its reading. However, the entire system is subject to potential failure should either of microvalves 41 or 46 fail or partially fail in an open state causing diluent and/or oxygen gas to continuously leak into all three sensor cavities with no independent means to know what the true PO2 is for the breathing gas flowing through breathing pathway 29. In general, it should be noted that the failure probability for microvalves 41 and 46 are orders of magnitude lower than the probability of condensate and other aging-related effects serving to spoof or degrade the sensor signals. But because of the global effect of even a small failure probability in a non-isolated system, the design of FIG. 5 is less preferred.

Two-Sensor Auto-Calibration Architectures

It can be appreciated from FIGS. 3, 4, and 5 that there are families of configurations associated with 2-sensor and 3-sensor PO2 control architectures that are amenable to the concepts of true auto-calibration and real-time auto-validation in embodiments of the present invention. We now formally list these option families and discuss their relative merits and weaknesses. In all of the architecture figures that follow, we have stripped out the details to show only those new features relevant to the auto-calibration and auto-validation.

Two Oxygen Sensors, One Auto-Calibrated/Auto-Validated, One Isolated

Figure 8:
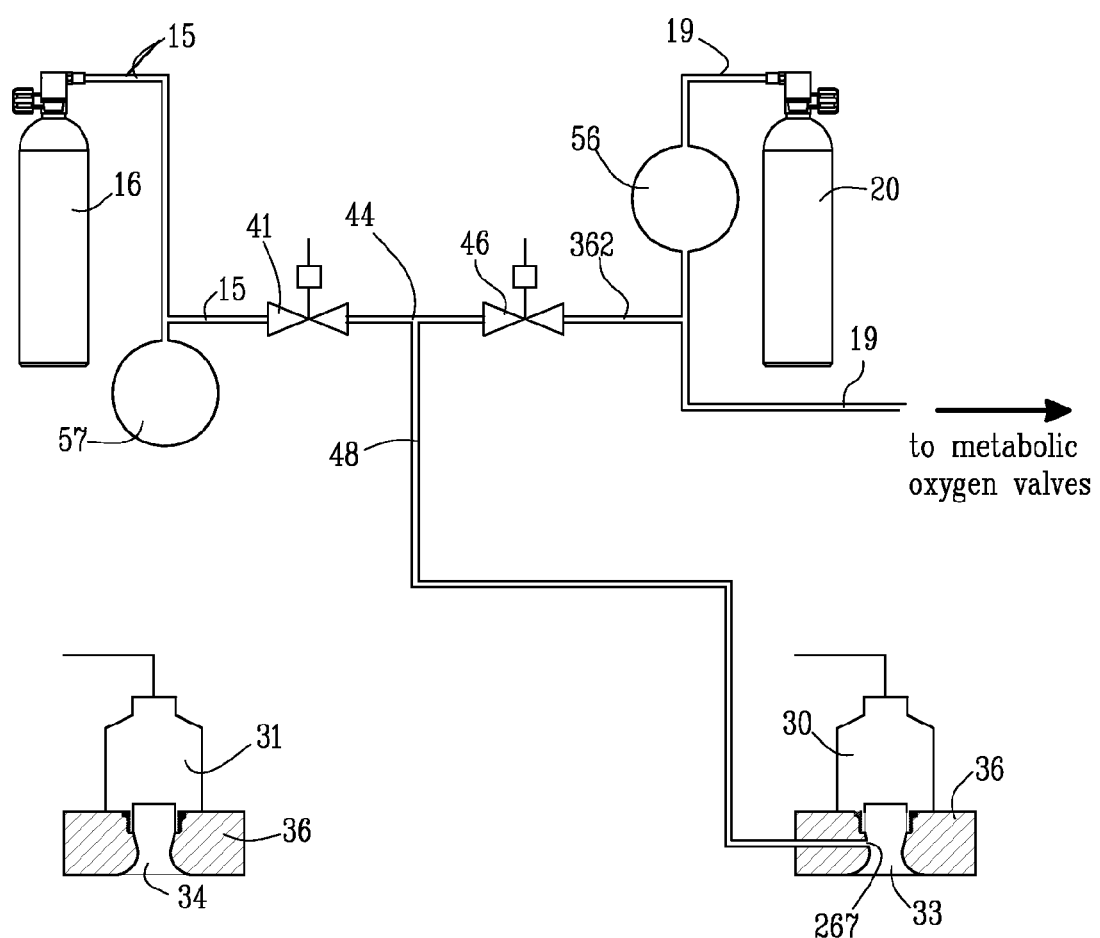
FIG. 8 shows a simplified version of the architecture in FIG. 3a, showing only the auto-calibration and auto-validation components.

FIG. 8 shows a simplified version of FIG. 3a, showing only the auto-calibration and auto-validation components. We will use this as a baseline when comparing other 2-sensor systems in the following. All component numbering and definitions remain as previously described. Hence, FIG. 8 shows a non-redundant 2-sensor system with one auto-calibrated and auto-validated sensor 30 and an independent microvalve leak detection sensor 31 that is isolated from possible leakage from the test valves 41, 46, which leakage e.g. may occur if either of microvalves 41 or 46 fail or partially fail in an open state.

Two Oxygen Sensors, All Auto-Calibrated/Auto-Validated, Non Isolated

Figure 9:
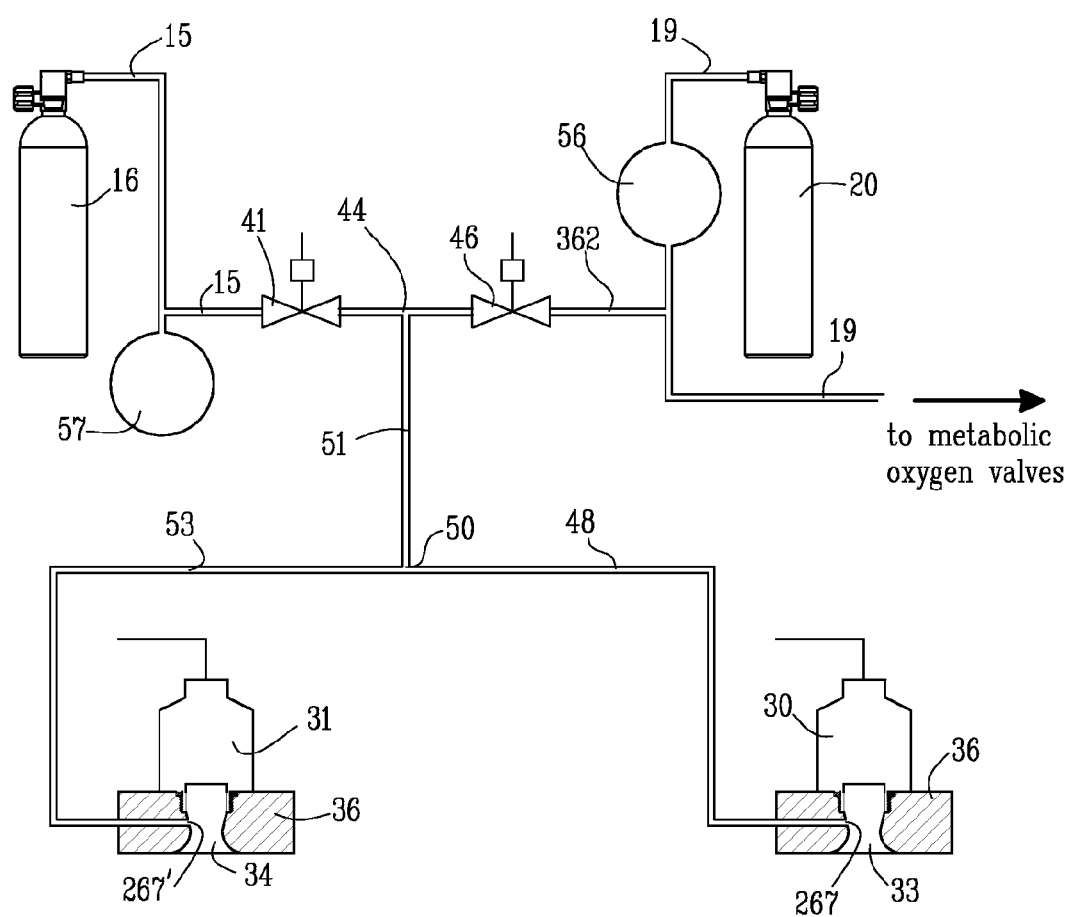
FIG. 9 shows the same architecture as in FIG. 8, except that also oxygen sensor 31 is connected to the diluent and oxygen gases.

FIG. 9 is the same as FIG. 8 except that also the oxygen sensor 31 is now connected to the diluent and oxygen gases via tube 53. The gases commonly flow through tube 51 and split at junction 50 to thence proceed unimpeded to both sensors 30 and 31. As previously described this is a less preferred design because of the small but finite possibility of a leak from test valves 41 and 46 spoofing the readings without any alternative means for independent validation.

Two Oxygen Sensors, all Auto-Calibrated/Auto-Validated, General Isolation Valve

Figure 10:
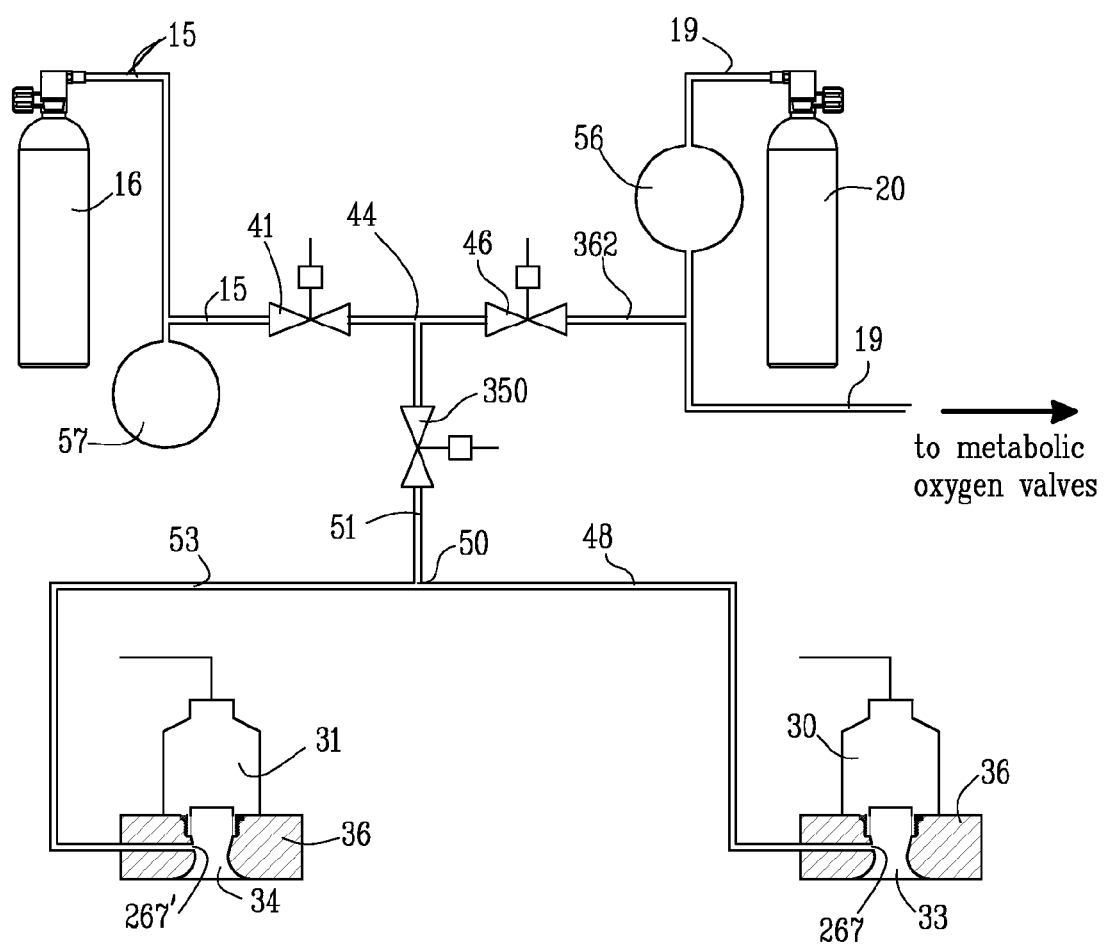
FIG. 10 shows the same as in FIG. 7 except that a general cut-off valve 350 has been added on gas pathway 51 common to both sensors 30, 31.

FIG. 10 is the same as FIG. 9 except that we have added a cut-off valve 350 controlled by the control unit 40 and arranged in the middle of gas pathway 51 to serve as all emergency auto-cut-off valve should either of test valves 41 or 46 be determined to be leaking. In other words, the cut-off valve 350 is arranged to operatively open and close the flow of at least one of said first gas or said second gas through the gas pathway 51 and tubes 15 and 362 mentioned above. While simple in concept, in the system shown here the only way to ascertain whether valves 41 or 46 are leaking is through the use of very accurate digital tank pressure gages on gas supplies 16 and 20. That said, however, this approach has certain advantages. As will be elaborated in some detail below with reference to FIG. 11, the automated valves 41, 46, 350 have low failure rates in the closed position, but substantially lower still failure rates to open when commanded to do so from a normally closed state. Because valves 41 and 350 and 46 and 350 are in series, the probability of either series failing in an open state is $P^2$, where P is the probability of any single valve failing in the open state. Since this combined failure probability is a very small number, the architecture presented in FIG. 10 represents a viable intermediate security level architecture for auto-calibration and auto-validation in closed cycle life support systems. It is important to point out the presence of valve 350, although intended primarily to cut-off a leak, has the possibility under certain circumstances to permit continued functioning of the auto-validation system. If the leak source is known (e.g. by the above tank pressure drop test, wherein the presence of a high resolution digital pressure sensor reports the pressure in both diluent and oxygen gas supplies to control unit 40, FIG. 3a), and the current ambient pressure measured by sensor 49 in FIG. 3a is within the safe range for auto-validation with that particular gas, then it is possible to momentarily open either valves 41 and 350 if diluent auto-validation is desired or valves 46 and 350 if oxygen auto-validation is desired, and then close all respective valves.

Two Oxygen Sensors, all Auto-Calibrated/Auto-Validated, One Auto-Isolated

Figure 11:
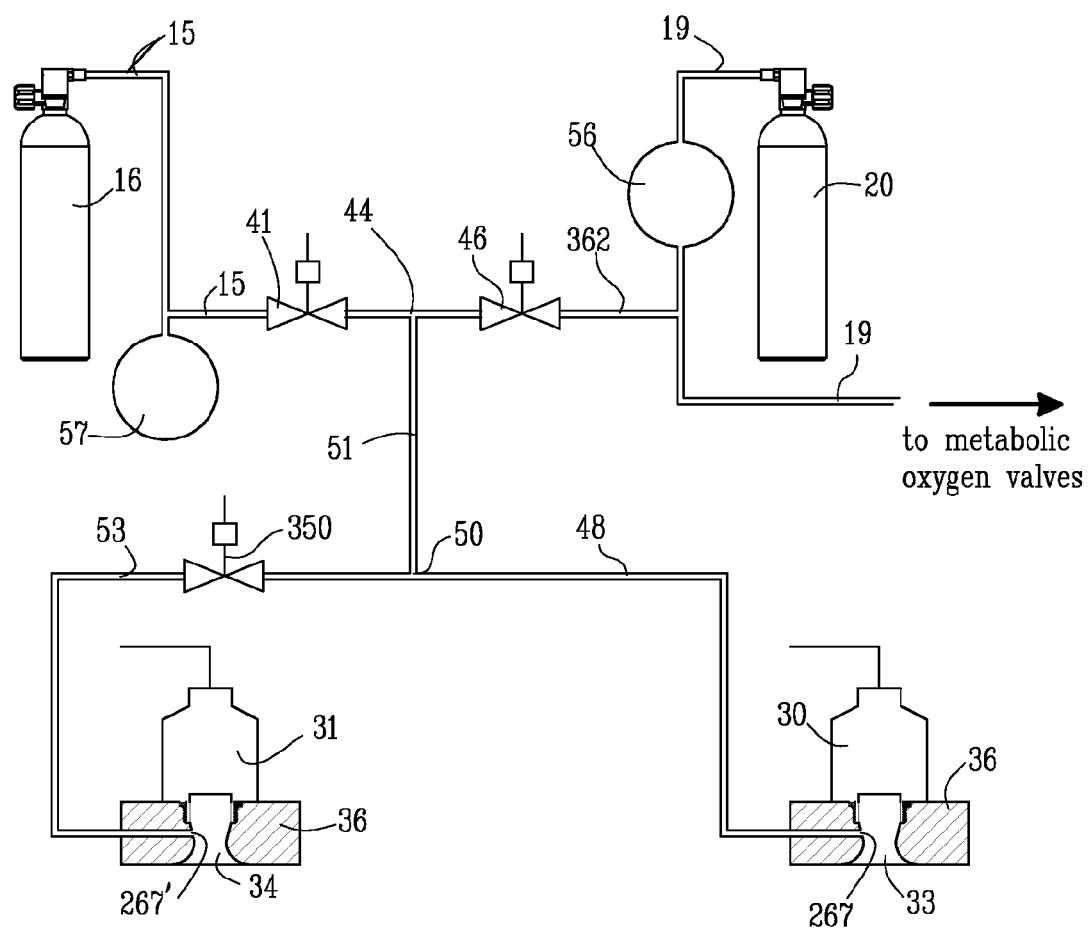
FIG. 11 shows the same as in FIG. 7 except that a cut-off valve 350 has been added on gas pathway 53.

FIG. 11 describes the system shown in FIG. 9 but with the important addition of a cut-off valve 350 controlled by the control unit 40 and arranged on gas pathway 53. Microvalve 350, like microvalves 41 and 46, is a normally-closed design. It therefore normally isolates sensor 31 from the diluent and/or oxygen gases that flow through conduit 51 and on through conduit 48 to Primary Oxygen Sensor 30. High quality microvalves of the type detailed here generally have asymmetric failure probabilities, with two states: failure to open (when normally closed), and failure to close after opening. In general, the "failure-to-open" mode for a normally-closed valve has a significantly lower probability of occurrence than for the "failure-to-close" mode—the latter having a much higher failure probability due to such possibilities as contaminant particles blocking full closure on the valve seat, and physical wearing on the valve seat components through use. Typical failure probabilities for comparison (based on the experience of the inventors in designing and using CCR equipment), including that for the failure of an oxygen sensor to produce a valid reading due to either condensate formation or aging-related effects would be approximately as follows:

Normally-closed solenoid valve failing to open: P=0.0005 (one in 2,000)

Normally-closed solenoid failing to close after opening: P=0.005 (one in 200)

Oxygen sensor failing to report correct PO2: P=0.05 (one in 50)

For this reason, it can safely be assumed that cut-off microvalve 350 will securely isolate sensor 31 from any small leaks from the diluent and/or oxygen gas source supplies (through closing failure in either microvalve 41 or 46). With proper design the line pressure drop at test orifice 267 for both sensing volumes 33 and 34 can be made approximately equal so that during normal operation both sensors 30, 31 could be auto-calibrated and auto-validated. In the event of a leak (or suspected leak) in microvalves 41 or 46 microvalve 350 could be closed and the behavior between sensors 30 and 31 cross correlated to verify whether a serious leak was extant and thence to issue an abort advisory to the user. Thus, in this design, we gain the benefit of having two auto-calibrated and auto-validated sensors during normal mode operation and a means to verify whether there is a leak in either of the auto-calibration and/or auto-validation valves during use.

Two Oxygen Sensors, all Auto-Calibrated/Auto-Validated, all Auto-Isolated

Figure 12:
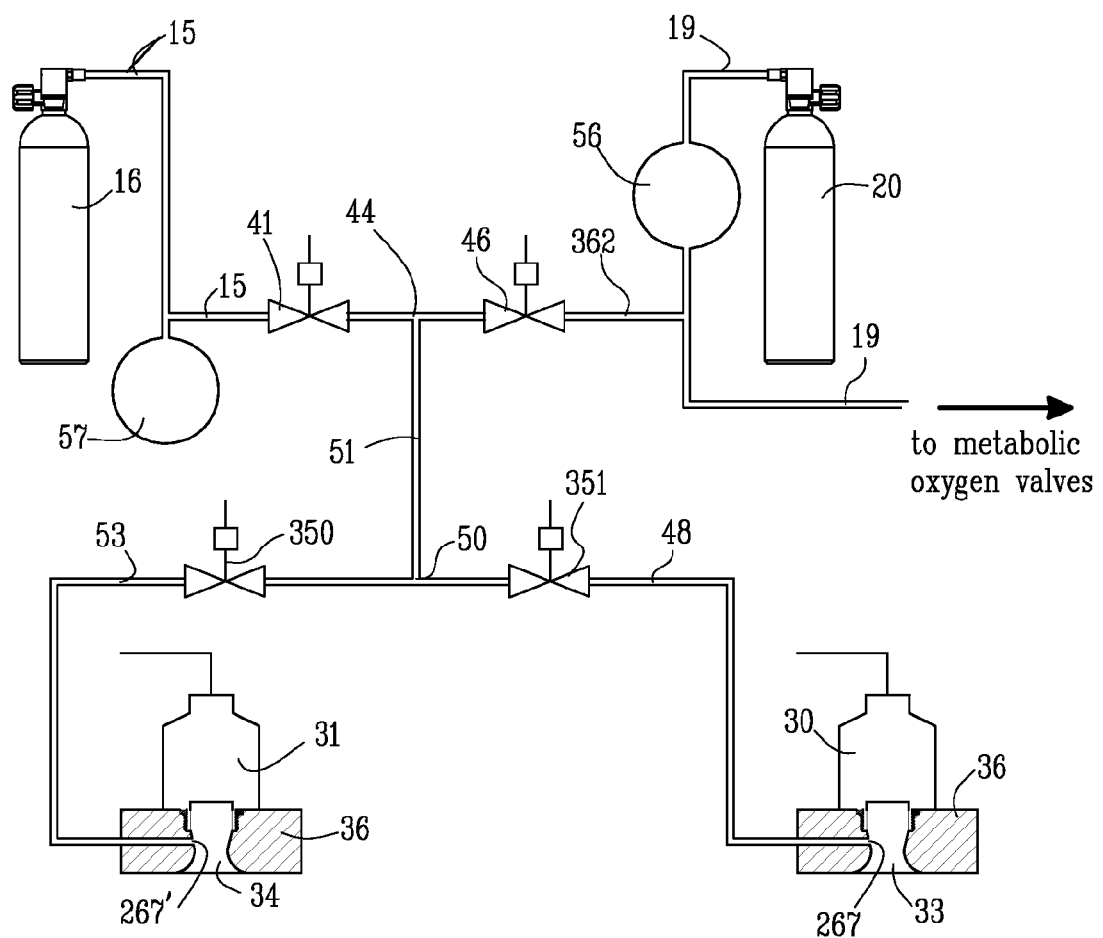
FIG. 12 shows the same as in FIG. 11 except that a further cut-off valve 351 has been added on gas pathway 48.

FIG. 12 describes the system shown in FIG. 11 but with the important addition of a cut-off valve 351 controlled by the control unit 40 and arranged on gas pathway 48. Microvalve 351, like microvalves 41, 46, and 350 is a normally-closed design. It therefore normally isolates sensor 30 from the auto-calibration gases that flow through conduits 51 and 48. This architecture, with the exception of gas pathway 51 and pathway junctions 44 and 50 represents the first true duplex redundant oxygen sensing system presented. With proper engineering and attention to detail, the failure probability of elements 44, 51, and 50 can be reduced to an exceedingly low number since they involve no moving parts and are otherwise inert and their integrity subject to periodic absolute testing. The system shown here in FIG. 12 is more reliable than any of the previous 2-sensor architectures presented. In the event of an open-failure leak in either of test valves 41 or 46, it is possible for the control unit 40 to detect this fact through a series of tests and, if necessary, can isolate sensors 30 and 31 from the leak. Since the leak can be detected (for example, through monitoring of gas tank pressure) it is possible for the computer to further isolate the leaking test valve to its specific source. Knowing this, the system could periodically open (separately) isolation valves 350, 351 and continue to auto-validate sensors 30 and 31, while commensurately issuing a warning advisory to the user.

Figure 13:
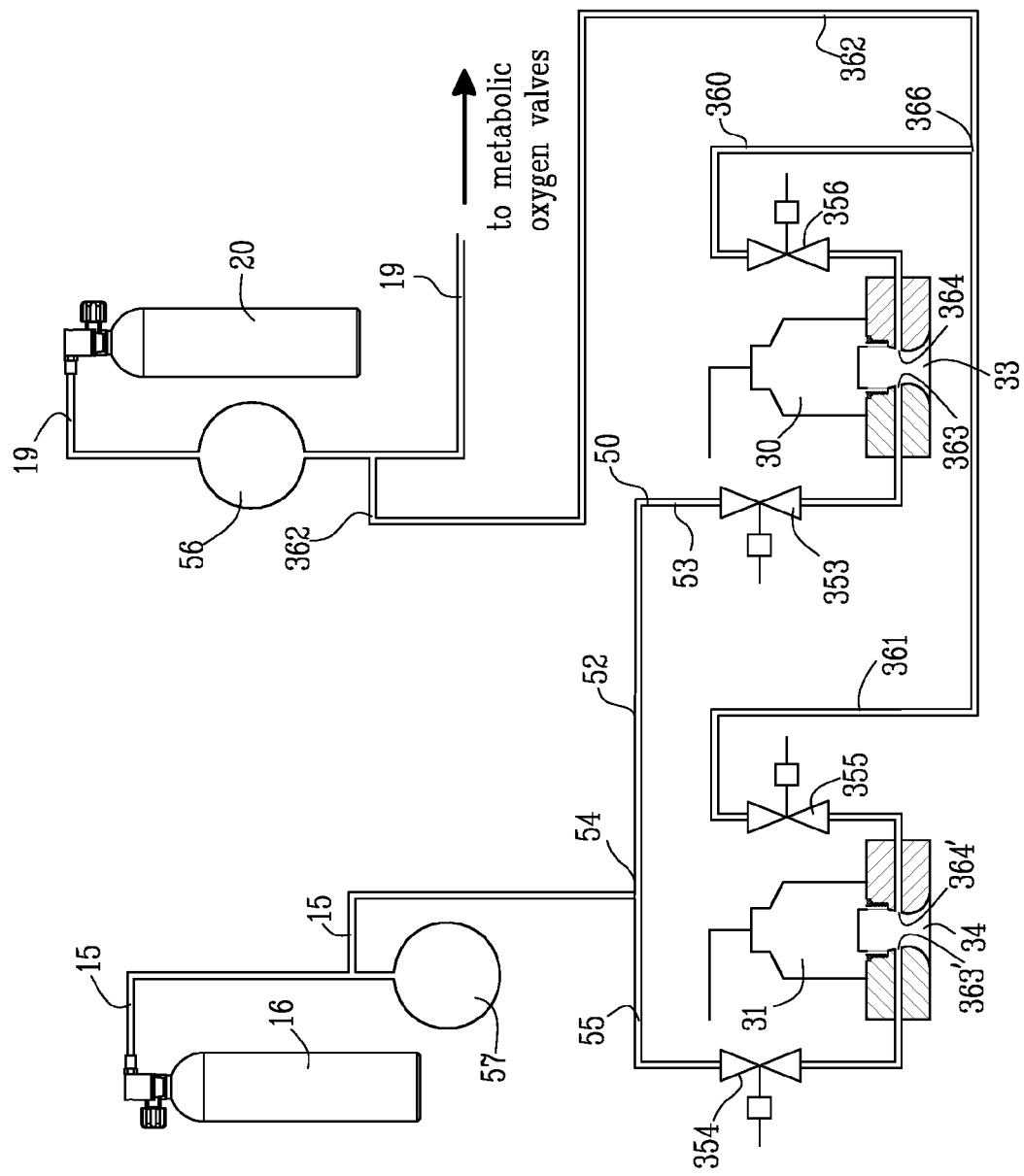
FIG. 13 shows an alternative architecture that eliminates the common manifold in FIGS. 9, 10, 11 and 12.

Two Oxygen Sensors, all Auto-Calibrated/Auto-Validated, all Auto-Isolated, Gas Source Isolation FIG. 13 describes an alternative architecture that eliminates the common pressurized manifold in FIGS. 9, 10, 11 and 12 represented by gas pathways 44, 51, and 50. The alternative architecture independently sends test gases (diluent, 16, and oxygen, 20) to separate final isolation and/or test valves 354 and 353, and 355 and 356 respectively for diluent and oxygen, to sensors 31 and 30, respectively.

Hence, in FIG. 13 oxygen is provided from oxygen supply 20 via tubes 19, 362 to joint 366, from joint 366 via tube 360 to sensor 30 via oxygen test valve 356 and oxygen test orifice 364, and from joint 366 via tube 361 to sensor 31 via oxygen test valve 355 and oxygen test orifice 364'. The test orifice 264, 264' for oxygen sensors 31, 32 are the same or similar as test orifices 267, 267', for sensors 30, 31 respectively.

Similarly, in FIG. 13 diluent is provided from diluent supply 16 via tube 15 to joint 54, from joint 54 via tube 52 to sensor 30 via diluent test valve 353 and diluent test orifice 363, and from joint 54 via tube 55 to sensor 31 via diluent test valve 354 and diluent test orifice 363'. The test orifices 263, 263' for oxygen sensors 31, 32 are the same or similar as test orifices 267, 267', for sensors 30, 31 respectively.

While this eliminates the common manifold failure it introduces double the probability of a valve failure since now there are effectively four test valves instead of two. This concept therefore, is an intermediary step on the path to true redundancy and not one that one would prefer in a practical device. The next four FIGS. 14, 15, 16, and 17) show how the architecture shown in FIG. 13 can be made into an extremely secure, practical life support system with duplex redundancy.

Figure 14:
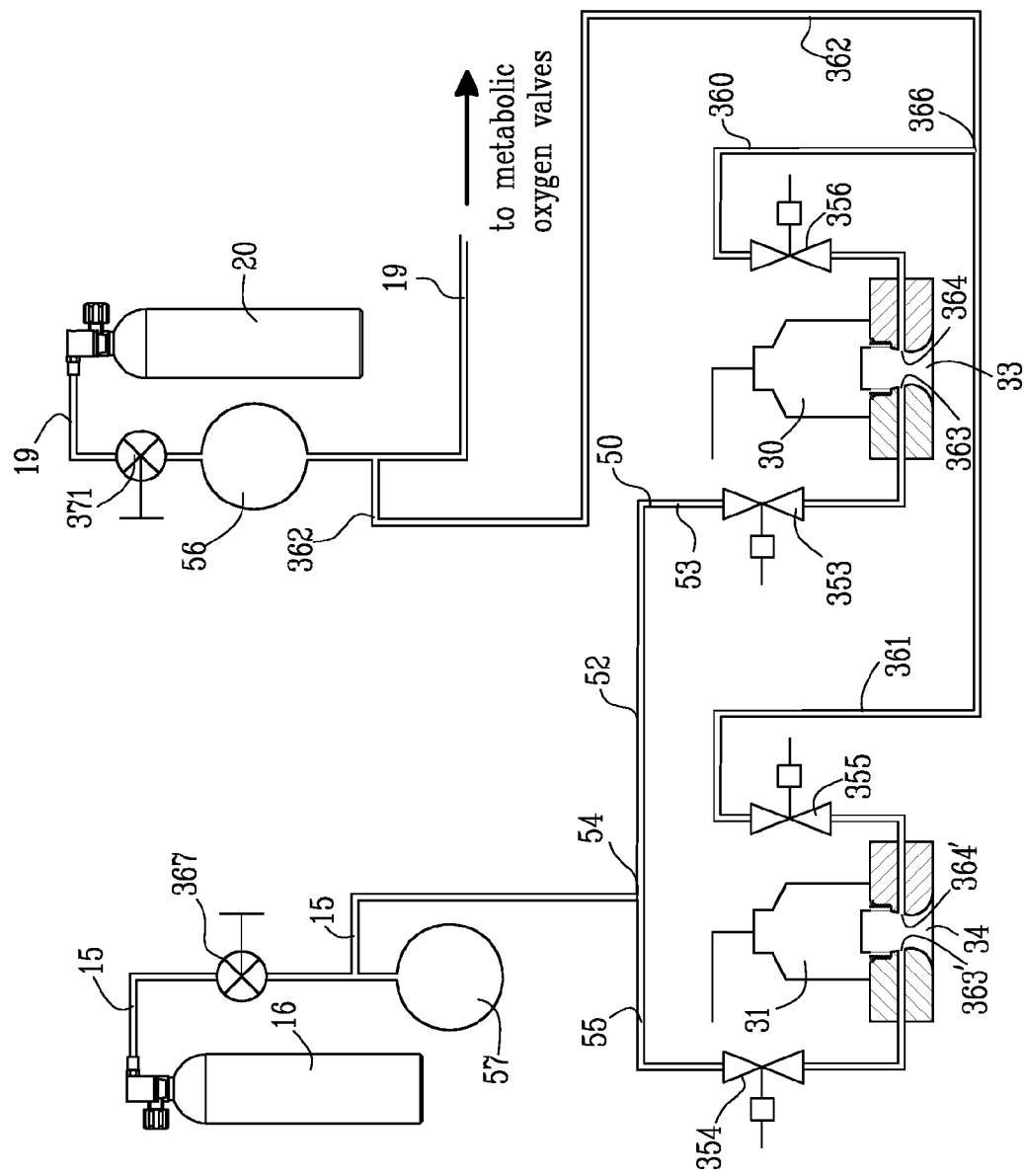
FIG. 14 shows the same as FIG. 13 but with the addition of manual cut-off valves 367 and 371.

Two Oxygen Sensors, all Auto-Calibrated/Auto-Validated, all Auto-Isolated, Gas Source Isolation, Manual Cut-Off Valve FIG. 14 shows the same architecture as FIG. 13 but with the addition of manual cut-off valves 367 and 371 for the auto-calibration diluent 16 and oxygen 20 gas sources, respectively. As can be seen in FIG. 14 the manual cut-of valve 367 is arranged on the diluent supply tube 15 for cutting of the diluent from test valves 353, 354, whereas the manual cut-of valve 367 is arranged on the oxygen supply tube 19 for cutting of the oxygen to the test valves 355, 356.

In and of itself, this does not affect the reliability of the auto-calibration and/or auto-validation system of FIG. 13, but it does give the user the ability to stop a problem caused by a potential leaking test valve 353, 354, 355, 356 and provides time for the user to think through his or her options. Manual cut-off valves of the type shown in FIG. 14 can be obtained in extraordinarily reliable designs such that the ability to isolate the test valve 353, 354, 355, 356 would not be in question. The location of cut-off valves 367 and 371 should be advantageously placed in a location (such as the user's chest) for ease of access in an emergency.

Figure 15:
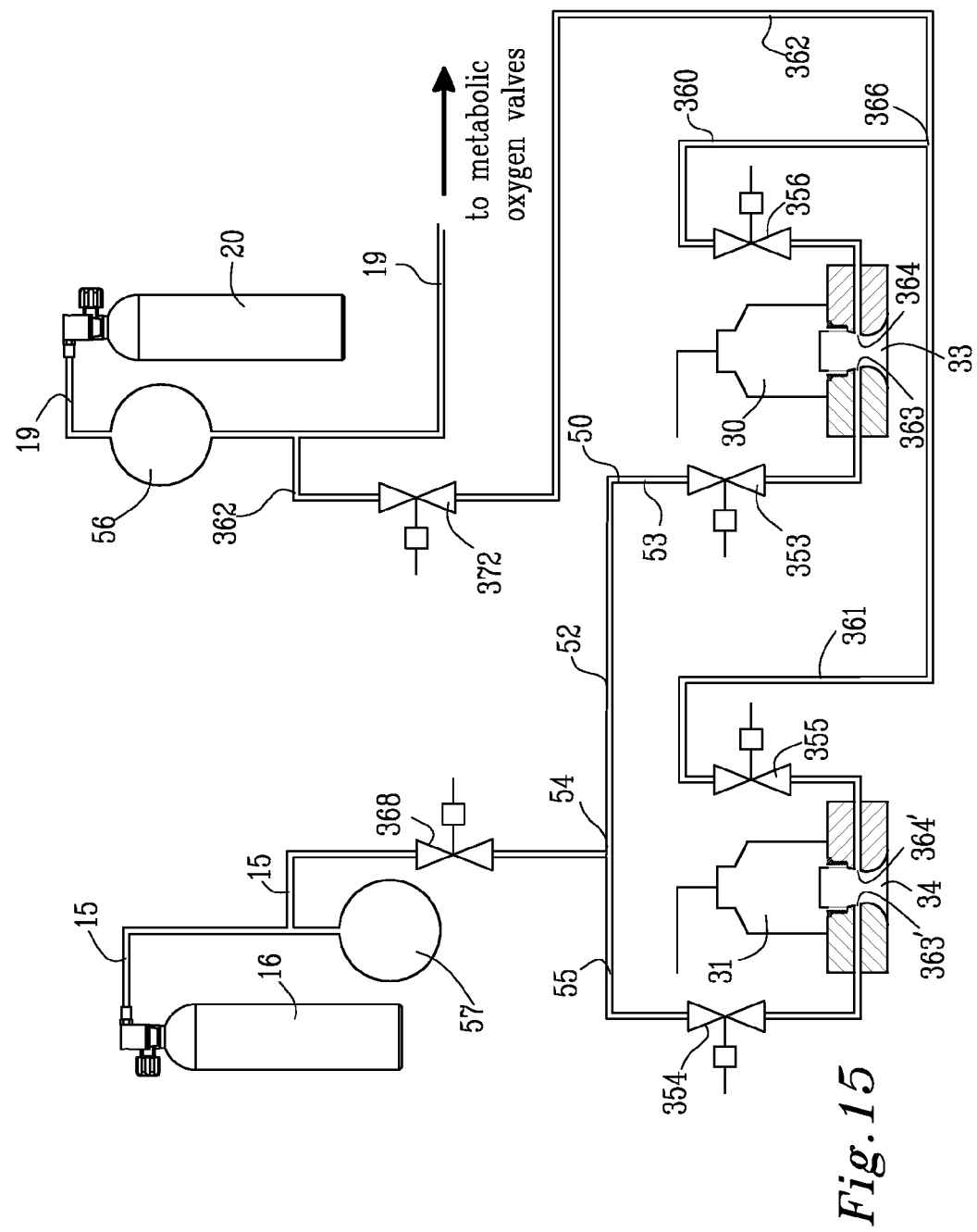
FIG. 15 shows the same as FIG. 14 but with auto cut-off valves 368 and 372, FIG. 16 combines FIGS. 14 and 15 providing both manual cut-off valves 367, 371 and auto cut-off valves 368, 371.

Two Oxygen Sensors, all Auto-Calibrated/Auto-Validated, all Auto-Isolated, Gas Source Isolation, Auto Cut-Off Valve FIG. 15 shows the same architecture as FIG. 14, but with the addition of auto cut-off microvalves 368 and 372 replacing manual cut-off valves 367, 371 and being controlled by the control unit 40 so as to cut-off the auto-calibration and/or auto-validation diluent 16 and oxygen 20 gas sources respectively. As can be seen in FIG. 15, the diluent cut-off valve 368 is arranged on tube 15 from the diluent source 16, whereas the oxygen cut-off valve 372 is arranged on tube 362 from the oxygen supply 20. As can be seen in FIG. 15, it is preferred that both auto cut-off valves 368, 372 are arranged in positions down streams the position of the manual cut-off valves 367, 371 described above.

This has the same advantageous effect as the 4-valve architecture shown in FIG. 12 but with the following additional advantage: each sensor 30 and 31 can be independently auto-calibrated/auto-validated while the other sensor stands by as a leak detection backup. In this fashion we achieve true redundant separation of the two oxygen sensors 30, 31 while being able to auto-calibrate and auto-validate each sensor independently.

Figure 16:
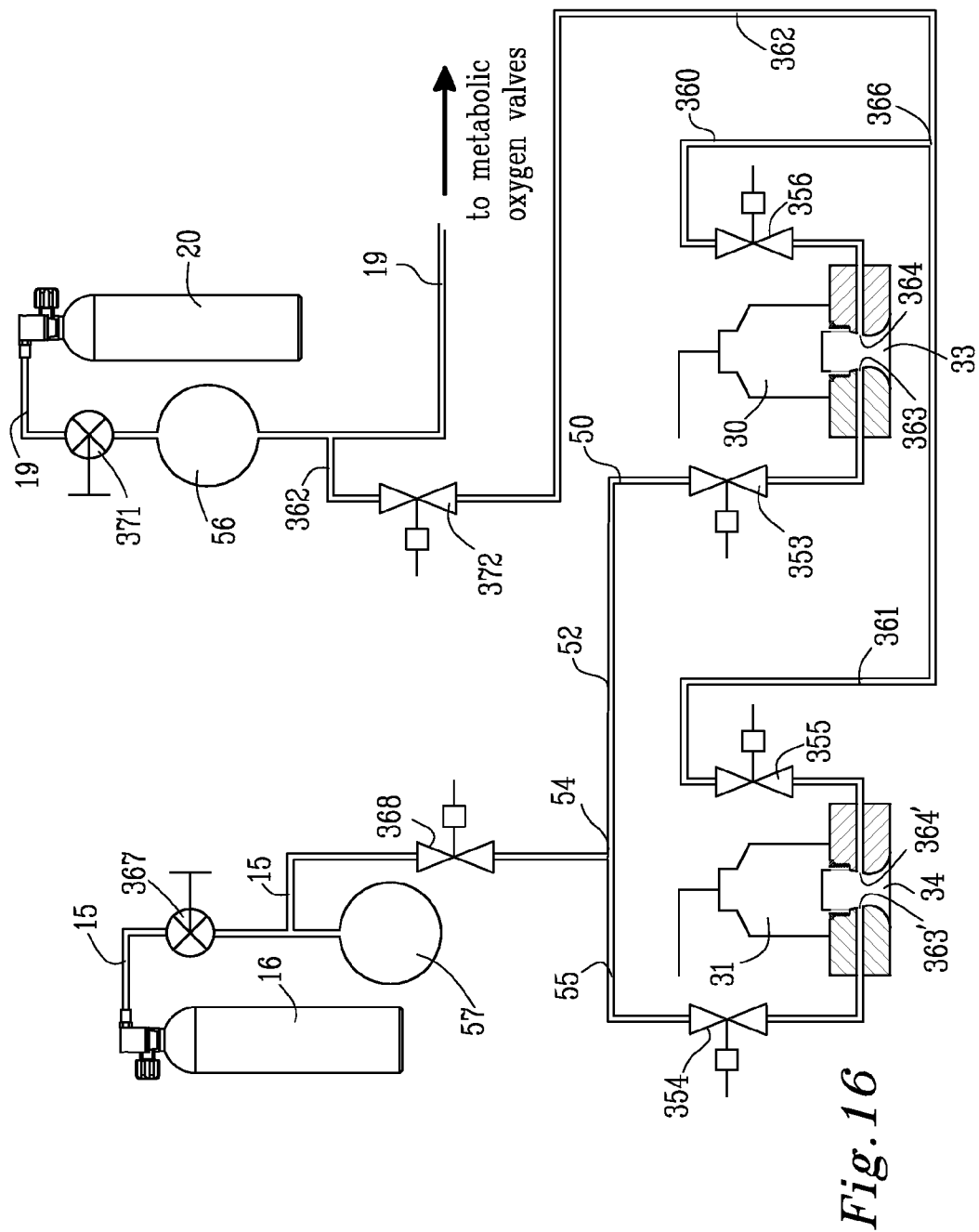

Two Oxygen Sensors, all Auto-Calibrated/Auto-Validated, all Auto-Isolated, Gas Source Isolation, Manual Cut-Off Valve and Auto Cut-Off Valve FIG. 16 combines the features of FIGS. 14 and 15 such that now we also have both the manual cut-off valves 367 and 371 as a last resort while having the benefit of the auto cut-off valves 368 and 371 to automatically handle any likely leak situation without requiring user intervention.

Two Oxygen Sensors, all Auto-Calibrated/Auto-Validated, all Auto-Isolated. Gas Source Isolation, Auto Cut-Off Valve, Manual Cut-Off Valve, Manual Bypass FIG. 17 adds to the features of FIG. 16 a manual bypass valve for both diluent 369 and for oxygen 370. Bypass valves 369 and 370 by themselves have been standard on CCR designs for more than 40 years and are as such not novel. However, the connection of the output of the diluent bypass valve 369 to the test channel line for the auto-calibration and/or auto-validation system (through gas pathways 373, 374, 375 and 377), such that it is possible to manually obtain sensor validation data in the event that the auto-validation system has failed during a mission and must be isolated (either automatically via microvalves 368 and 372 or via the manual cut-off valves 367 and 371). One may say that a manual bypass valve 369 and manual bypass test channel arrangement has been accomplished (through gas pathways 373, 374, 375 and 377) for diluent providing diluent from gas supply 16 to the primary oxygen sensors 30 and 31 at a first positions 363 and 363' adjacent to or directly adjacent to the primary oxygen sensors 30 and 31.

The auto cut-off microvalves 368 and 372 for diluent and oxygen respectively; the manual cut-off valves 367 and 371 for diluent and oxygen respectively; and the manual bypass valves 369 and 370 for diluent and oxygen, respectively, can also be added to all of the former designs to improve the performance and safety of those designs. In particular, the addition of the manual cut-off and manual bypass valves to the architecture of FIG. 12 would make for a potent, compact and highly reliable gas control system for a CCR, while the design in FIG. 17 would be considered both extremely reliable and have the added benefit of additional degraded, but still fully closed cycle and automated, options for operation in an emergency. Both of these designs have the following beneficial effects:

Increased probability of being able to complete a mission even though certain components in the system may fail during the course of a mission Increased safety to the user because the design is truly duplex redundant and therefore both redundant sensing and control lines (including their respective microvalves) must fail independently before the user is forced to abort to an alternative external system for survival.

Figure 17:
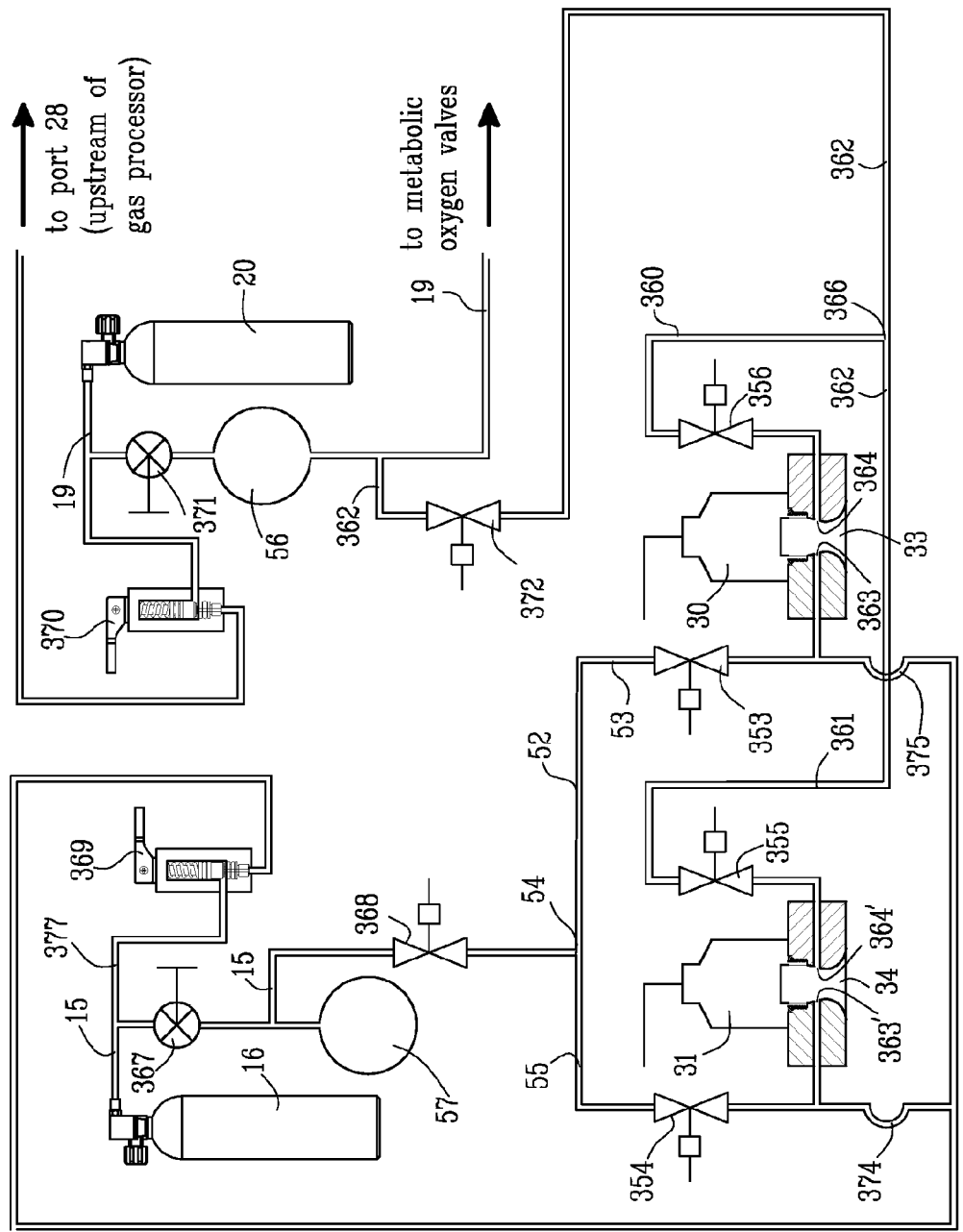
FIG. 17 shows the same as FIG. 16 but with the addition of bypass valves 369 and 370.

In the design of FIG. 17 a manual diluent bypass system receives gas upstream of manual cut-off valve 367 such that the possibility exists of injecting diluent gas into the system manually even in the event of the requirement to manually isolate all electronic valves in the system. In such case, manual bypass valve 369 receives low pressure (8-12 bar) diluent from source tank 16 via gas pathway 377. When triggered manually, diluent gas then travels down gas pathway 373 to diverter pathways 374 and 375 that merge with the respective outputs of diluent test valves 354 and 353, respectively. From that junction the gas is sent to injection orifices 363, 363' that inject gas into sensing cavities 33 and 34.

The nature of this injection creates a turbulent vortex that both lifts sensor condensate off the sensor while simultaneously exposing the sensor to the diluent validation gas yet not causing damage to the sensing membrane of the oxygen sensor.

Three Oxygen Sensors Auto-Calibration/Auto-Validation and Achieving True Triplex Redundancy We now extend the 2-sensor concepts, discussed above with reference to FIGS. 8-17, in to an auto-calibration and auto-validation system wherein three oxygen sensors are employed. In each of the figures that follows, comparisons will be made to similar architectures disclosed in the FIGS. 8-17, ultimately leading to two three-sensor architectures that can be considered to be independent, true triplex redundant oxygen sensing, auto-calibration, and auto-validation systems.

Three Oxygen Sensors, Two Auto-Calibrated/Auto-Validated, One Isolated

Figure 18:
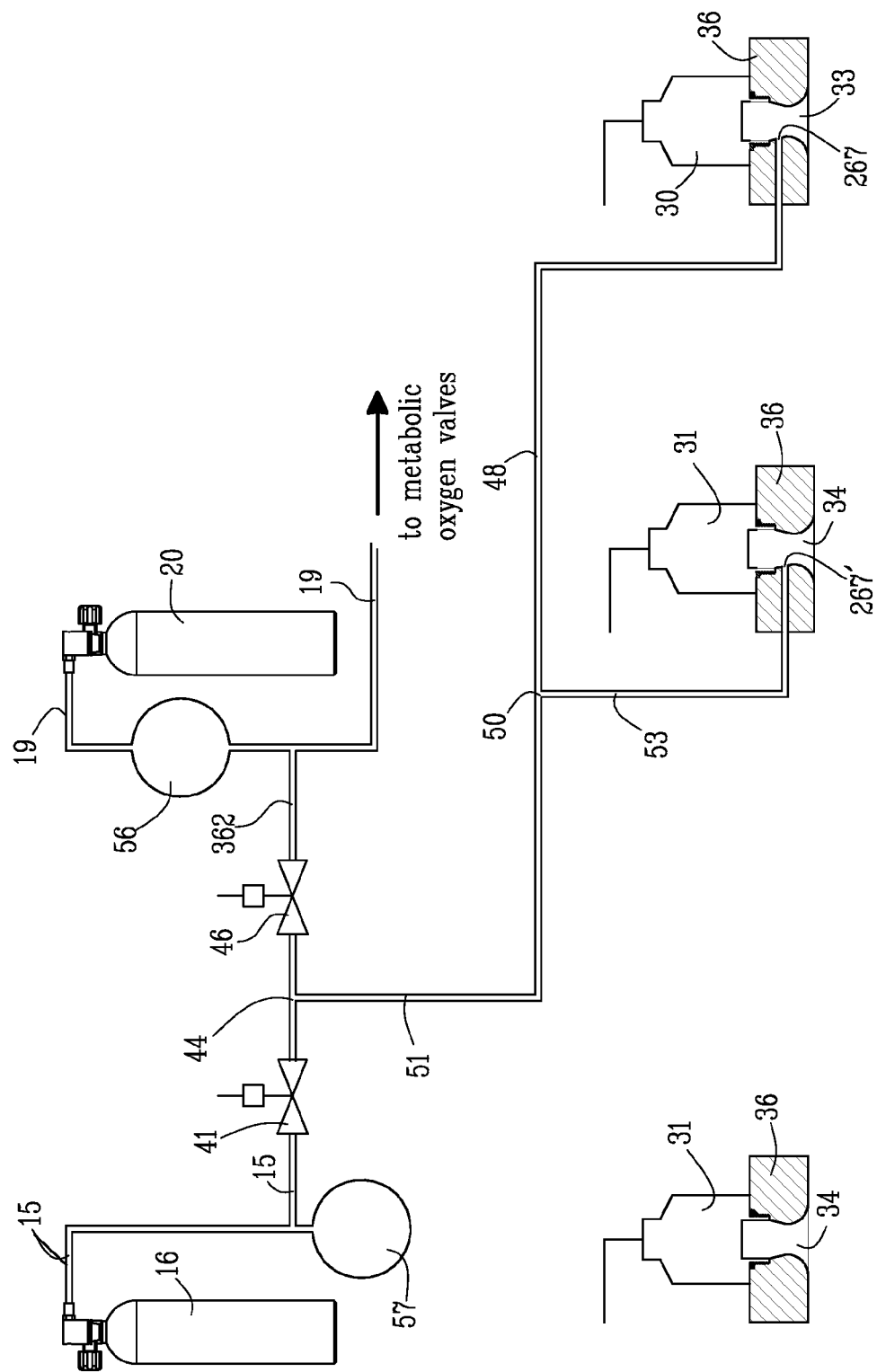
FIG. 18 shows a simplified version of the architecture in FIG. 4, showing only the auto calibration and auto-validation components.

FIG. 18 shows a simplified version of FIG. 4, showing only the auto-calibrating and/or auto-validating components, also cf. FIG. 8. All component numbering and definitions remain as previously described. Hence, FIG. 18 shows a redundant 3-sensor system with two auto-calibrated and/or auto-validated sensors 30, 31 and an independent microvalve leak detection sensor 32 that is isolated from possible leakage from the test valves 41, 46.

The benefit of this design is that it is very simple to implement. Two independent sensors 30 and 31 are able to be auto-calibrated and in addition, during the course of an actual mission, these two sensors 30 and 31 can be auto-validated. Under normal operating conditions (that is to say, no leaks from the normally-closed calibration microvalves 41 and 46), the system will have access to two independently validated sensor readings. If both are within reasonable agreement a simple averaging algorithm can be used for oxygen control in the CCR. If one of the sensors either 30 or 31 fails the auto-validation test, then the control unit 40 can decide to use the single sensor that passes the auto-validation test for automated PO2 control. It will also advise the user of the failed validation test in the alternate sensor, e.g. by means of sound signals and/or light signals as is well known to those skilled in the art. Similar to the system shown in FIG. 4 and also FIG. 9, a leak failure in either of test valves 41 or 46 will serve to render the readings of sensors 30 and 31 meaningless relative to the true PO2 of the gas in the breathing loop. However, unlike e.g. FIG. 9, this is a detectable failure because of the presence of auxiliary secondary oxygen sensor 32.

Three Oxygen Sensors, Three Auto-Calibrated/Auto-Validated, Non Isolated

Figure 19:
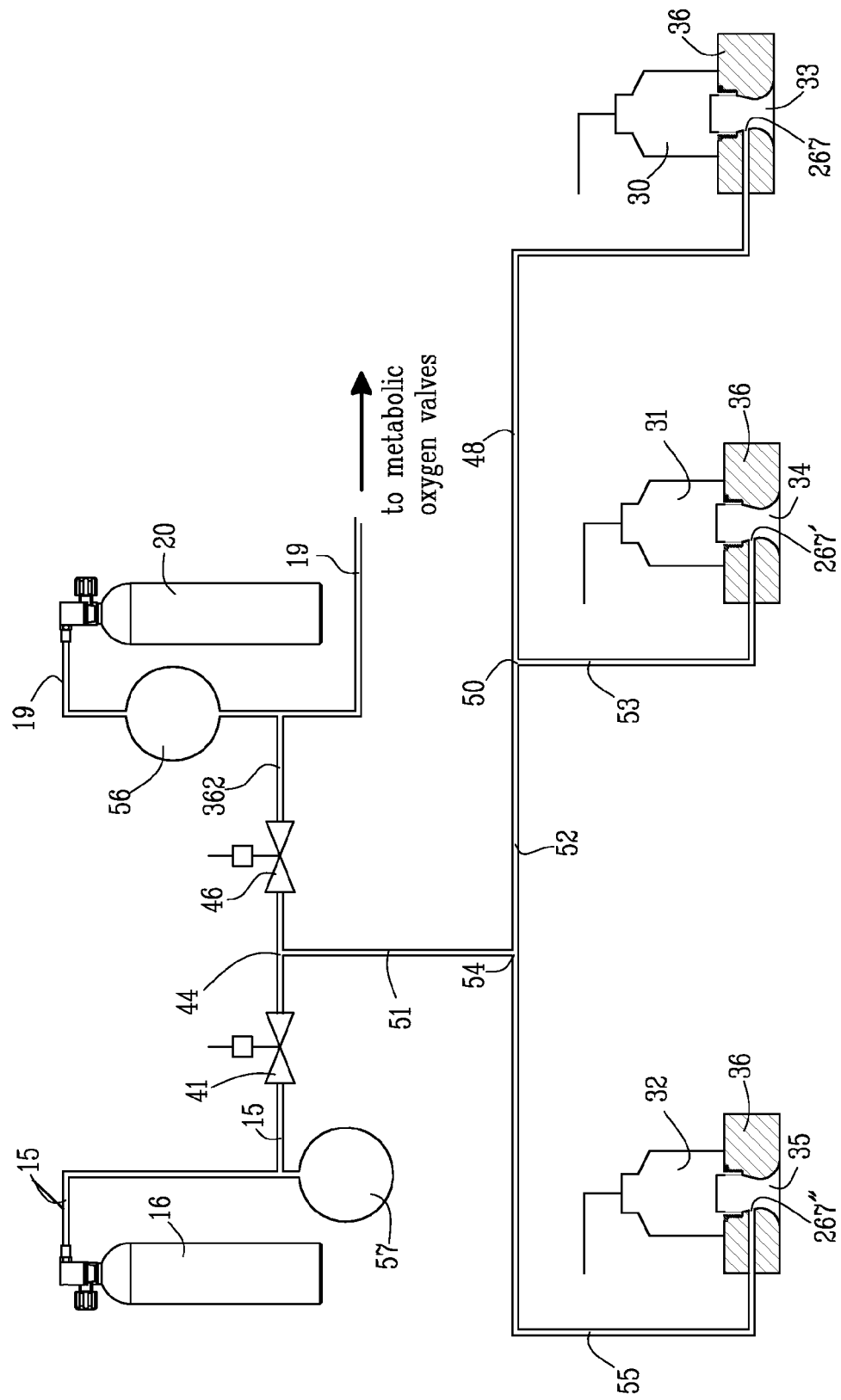
FIG. 19 shows a simplified version of the architecture in FIG. 5, showing only the auto calibrating and/or auto-validating components.

FIG. 19 shows a simplified version of FIG. 5, showing only the auto-calibrating and/or auto-validating components, also cf. FIG. 9. All component numbering and definitions remain as previously described. Hence, FIG. 19 shows a redundant 3-sensor system with all sensors auto-calibrated and auto-validated.

Like FIG. 9, the system shown in FIG. 19 has the common failure mode in which a persistent leak in either of the test valves 41 or 46 will render the entire sensor array incapable of determining the true PO2 in the breathing loop. We show this here for completeness. This is considered as a less preferred design because of the small but finite possibility of a leak from test valves 41 and 46 spoofing the readings without any alternative means for independent validation.

Figure 20:
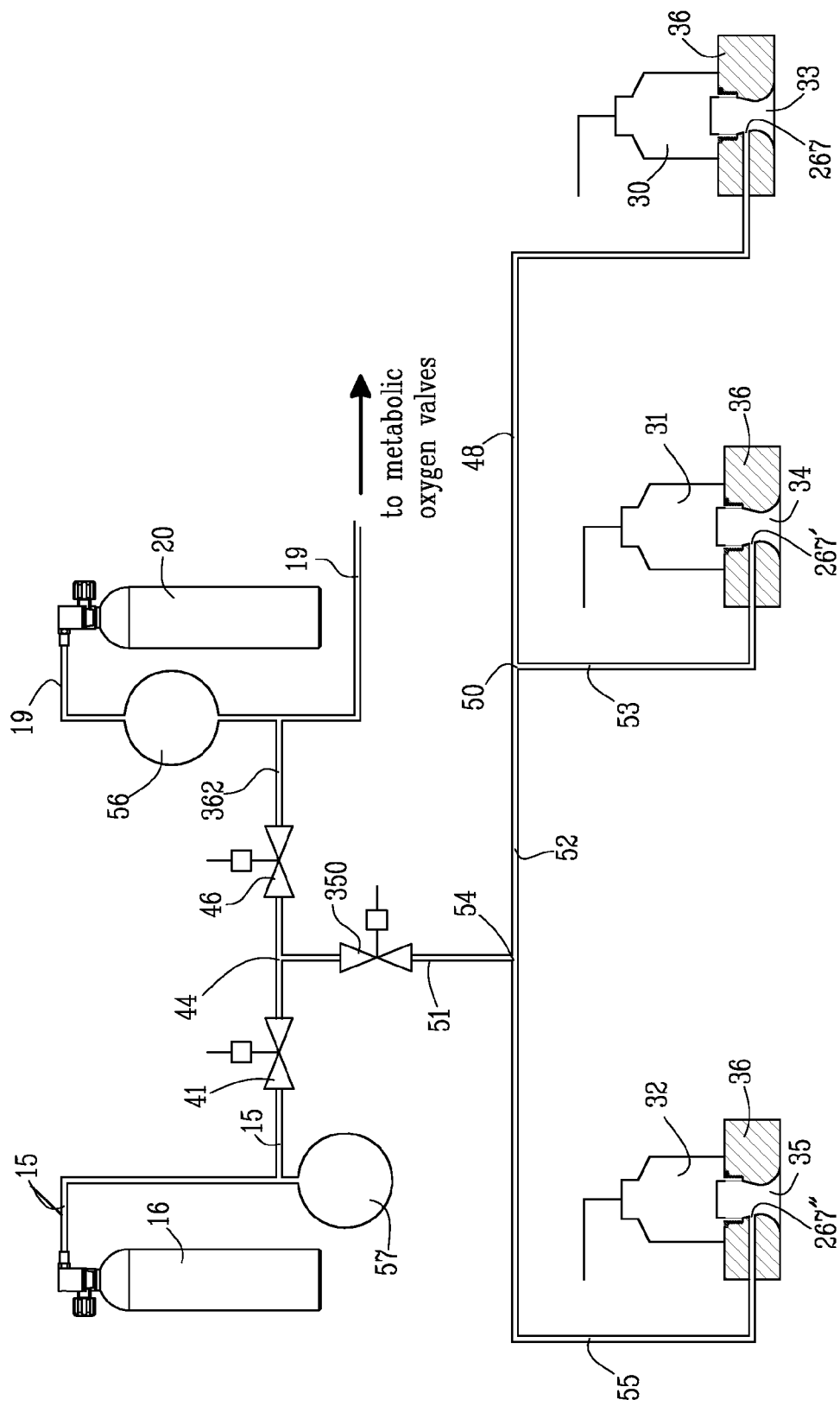
FIG. 20 is the same as FIG. 19 except that an auto cut-off valve 350 has been added on the gas pathway 51.

Three Oxygen Sensors, all Auto-Calibrated/Auto-Validated, General Isolation Valve FIG. 20 is the same as FIG. 19 except that an automated cut-off valve 350 is added on the gas pathway 51 to serve as an emergency auto-cut-off valve should either of test valves 41 or 46 be determined to be leaking. Hence, the comments made above with reference to FIG. 10 apply equally to the architecture of FIG. 20 and this represents a viable, intermediate-level security auto-calibration and auto-validation system for closed cycle life support systems wherein there are now three sensors in use. Because all three can be auto-validated during a mission, all three must fail the auto-validation test before a system abort situation exists.

Three Oxygen Sensors, Three Auto-Calibrated/Auto-Validated, One Auto-Isolated

Figure 21:
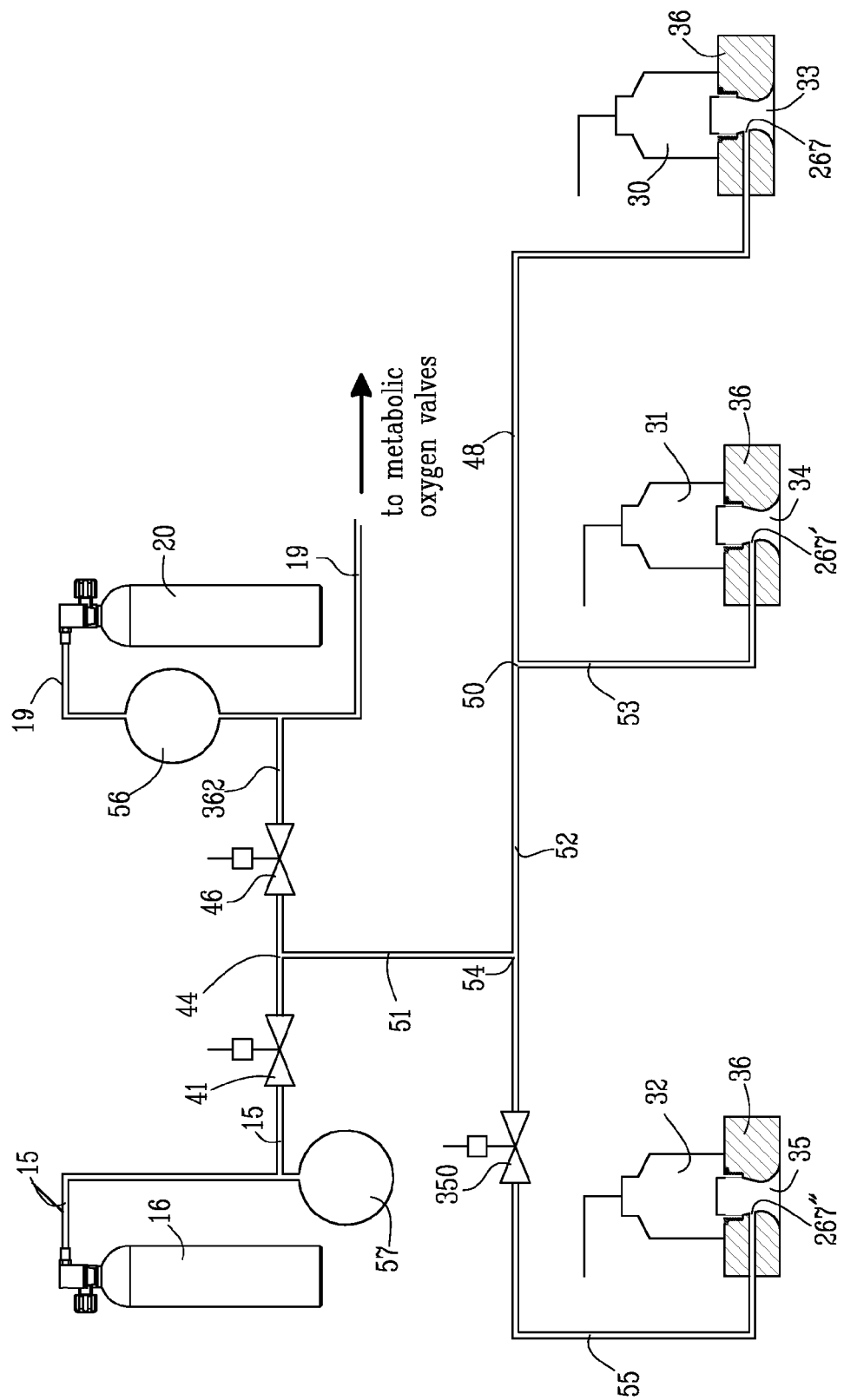
FIG. 21 is the same as FIG. 19 except that an auto cut-off valve 350 has been added after junction 54 on the gas pathway 55.

FIG. 21 is the same as FIG. 19 except that an automated cut-off valve 350 is added after junction 54 on the gas pathway 55, also cf. FIG. 11.

In FIG. 21, oxygen sensors 30 and 31 are connected directly to the test valves 41 and 46 via gas pathways 51 and 52 without any isolation. Oxygen sensor 32, however, although also connected to the test valves 41, 46 (via gas pathways 51 and 55) is isolated by cut-off valve 350. Cut-off valve 350, like test valves 41 and 46 is a normally-closed design. It therefore normally isolates sensor 32 from the auto-calibration and/or auto-validation gases that flow from diluent supply 16 and/or oxygen supply 20 respectively through conduit 51 and on through conduit 48 to Primary Oxygen Sensors 30 and 31.

For reasons previously elaborated in detail above with reference to FIG. 11, it can safely be assumed that cut-off valve 350 will securely isolate sensor 32 from any small leaks in the auto-calibration gas source supplies (through closing failure in either microvalve 41 or 46). With proper design the line pressure drop at test orifices 267, 267', 267" for all sensing volumes 33, 34, and 35 can be made approximately equal so that during normal operation all three sensors 30, 31, 32 can be auto-calibrated and auto-validated. In the event of a leak (or suspected leak) in microvalves 41 or 46 microvalve 350 could be closed and the behavior between sensors 30, 31 and 32 cross correlated to verify whether a serious leak was extant and thence to issue an abort advisory to the user, e.g. in case of a leakage it can be expected that sensor 32 produces a measure that differs from the measures produced by sensors 30, 31 when cut-off valve 350 is closed.

Thus, in this design, we gain the benefit of having three auto-validated sensors during normal mode operation and a means to verify whether there is a leak in either of the auto-calibration and/or auto-validation valves 41, 46 during use.

Figure 22:
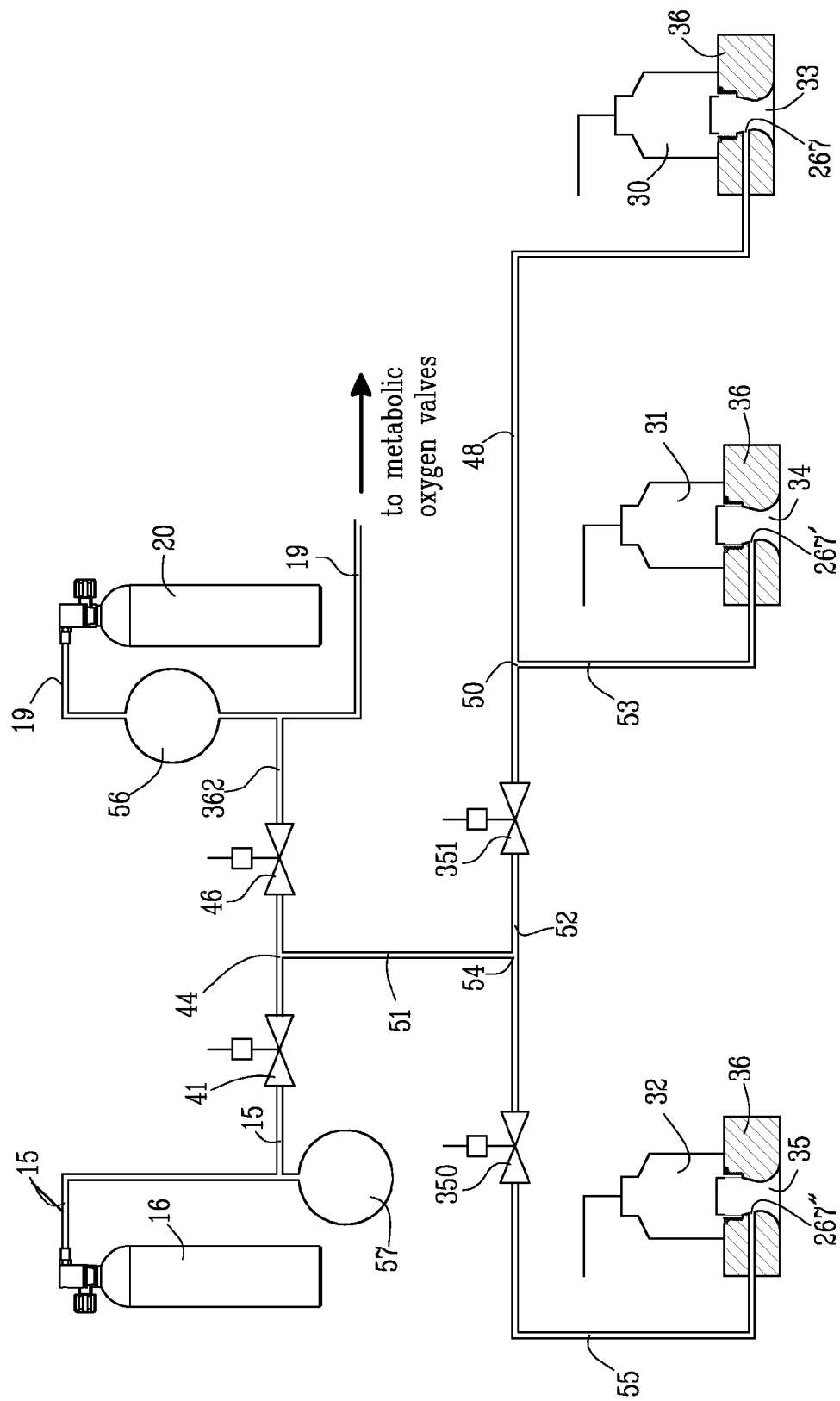
FIG. 22 is the same as FIG. 20, but with the addition of normally-closed cut-off valve 351 on gas pathway 52.

Three Oxygen Sensors, Three Auto-Calibrated/Auto-Validated, Two Sensor Clusters Auto-Isolated FIG. 22 describes the system shown in FIG. 20 but with the addition of normally-closed cut-off valve 351 on gas pathway 52, also cf. FIG. 12. Cut-off valve 351, like microvalves 41, 46, and 350 is a normally-closed design. It therefore normally isolates sensors 30 and 31 from the auto-calibration and/or auto-validation gases that flow through conduits 51 and 52. This architecture has the same merits of the system described in FIG. 12 but now clusters two oxygen sensors 30, 31 downstream of valve 351. Unlike the architecture of FIG. 12 (which is a true duplex redundant design), the architecture presented in FIG. 22 is not a true triplex redundant design, but rather represents an incremental improvement over the duplex redundant design in which a third oxygen sensor is available for auto-validation. This is a viable, real improvement in system reliability because the oxygen sensors themselves (see discussion above with reference to FIG. 11) are in fact the least reliable components in this system (that is, they have the highest probability of failure during a mission) and thus, adding more of them, provided they can be auto-validated, represents an improvement in mission redundancy.

Figure 23:
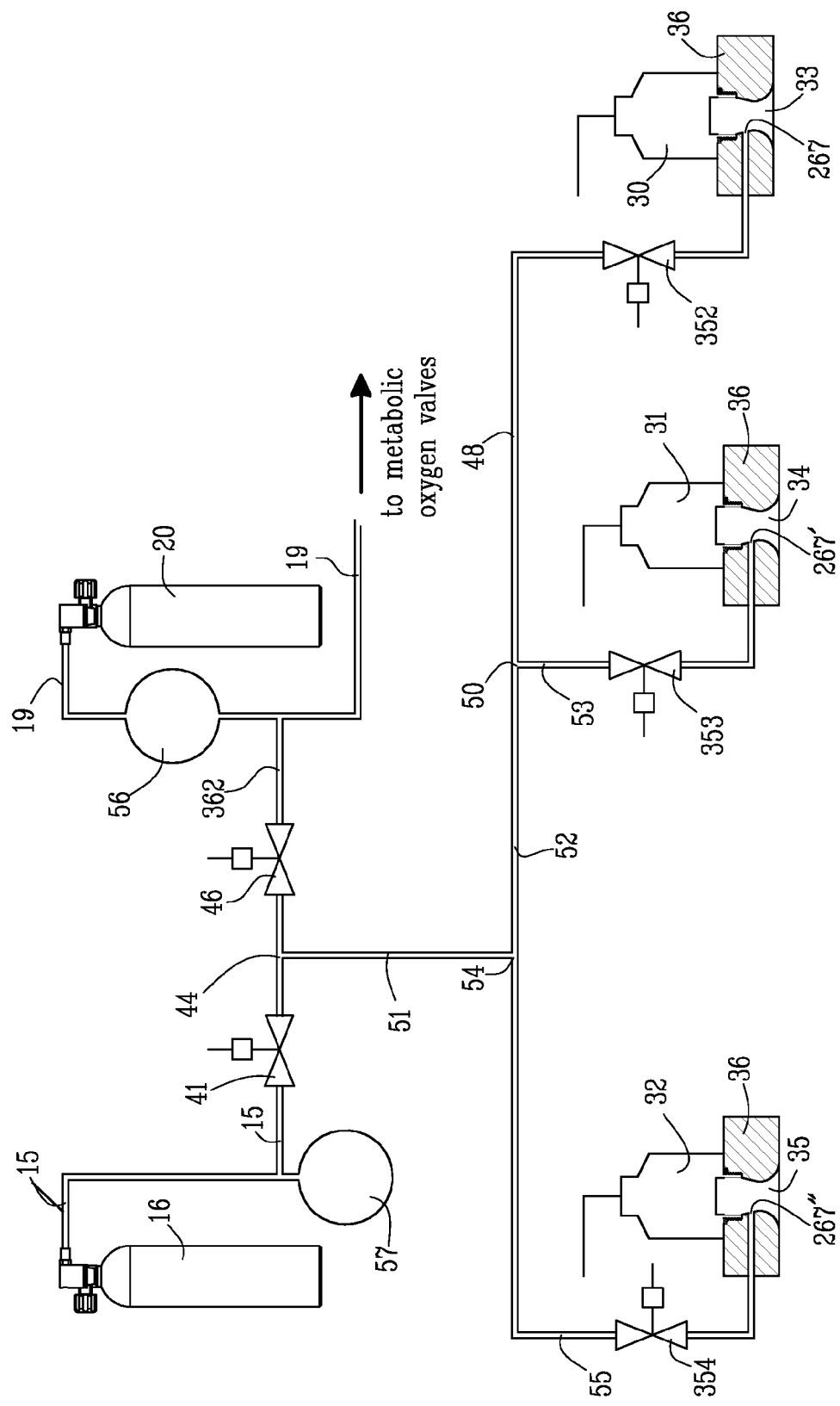
FIG. 23 is the same as FIG. 22, but with the exception that each individual oxygen sensor 30, 31, and 32 has its own auto cut-off valve 352, 353, and 354, respectively.

Three Oxygen Sensors, Three Auto-Calibrated/Auto-Validated, all Sensors Auto-Isolated FIG. 23 describes the architecture of FIG. 22, but with the notable exception that each individual oxygen sensor 30, 31, and 32 has its own auto-cut-off valve 352, 353, and 354, respectively.

As a general remark, it should be emphasised that the gas transfer pathways and junctions between the test valves 41 and 46 and the sensors 30, 31, 32, namely 44, 51, 54, 55, 50, 53, and 48 can, in general, be designed to be failproof relative to the other elements in all of the architectures thus far described. The reason for this is that there are no moving parts, no systems to degrade, and no consumables to use up nor environmental effects of significant concern. An example would be machining these gas pathways inside a block of metal such that the yield stress of the metal is dramatically higher than the service pressure it must hold. Thus, despite the common gas manifold between test valves 41 and 46 and auto-cut-off valves 352, 353, and 354 it is safe to assume that the probability of failure of this system will be for all practical purposes, determined entirely by the reliability of those valves, and not by the connecting static infrastructure. For these reasons, FIG. 23 represents the first architecture for a true triplex redundant oxygen sensing, calibration, and validation system for closed-cycle life support systems.

Figure 24:
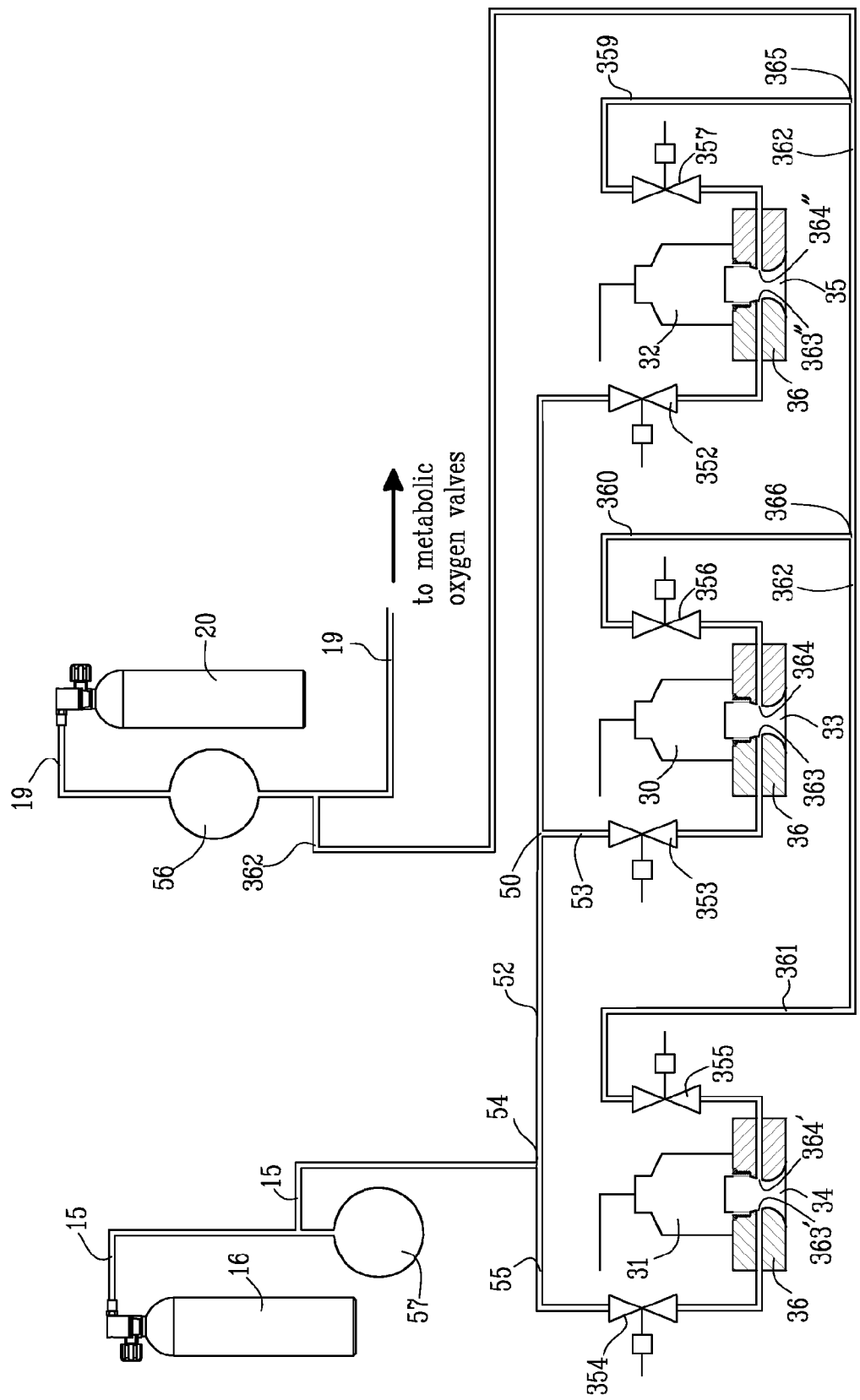
FIG. 24 is same as FIG. 13, but with the addition of a third "gas sensing and validation" unit.

Three Oxygen Sensors, Three Auto-Calibrated/Auto-Validated, all Sensors Auto-Isolated, Gas Source Isolation FIG. 24 describes the architecture of FIG. 13, but with the addition of a third "gas sensing and validation" unit (consisting of sensor 32, auto cut-off valves 352 and 357, and the associated gas pathways required to connect it to the auto-calibration and/or auto-validation gas sources diluent supply 16 and oxygen supply 20 respectively).

FIG. 24 describes an alternative architecture that eliminates the common pressurized manifold in FIGS. 19, 20, 21, 22 and 23 represented by gas pathways 44, 51, and 54. The alternative architecture independently sends test gases (diluent, 16, and oxygen, 20) to separate final isolation and/or test valves 352, 353, 354 and 355, 356, 357 respectively for diluent and oxygen, to sensors 30, 31 and 32, respectively.

Hence, in FIG. 24 oxygen is provided from oxygen supply 20 via tubes 19, 362 to joint 365, from joint 365 to sensor 32 via test valve 375 and orifice 364"; from joint 365 via tube 362 to joint 366, from joint 366 via tube 360 to sensor 30 via oxygen test valve 356 and oxygen test orifice 364; and from joint 366 via tube 361 to sensor 31 via oxygen test valve 355 and oxygen test orifice 364'. Test orifice 264" is the same or similar as test orifices 264, 264'.

Similarly, in FIG. 24 diluent is provided from diluent supply 16 via tube 15 to joint 54, from joint 54 to joint 50 to sensor 32 via diluent test valve 352 and diluent orifice 363"; and from joint 54 via tube 52 to joint 50 to oxygen sensor 30 via tube 53 and diluent test valve 353 and diluent test orifice 363; and from joint 54 via tube 55 to sensor 31 via diluent test valve 354 diluent test orifice 363'.

The arguments presented above with reference to FIG. 13 also apply to this 3-sensor architecture. This concept therefore, is an intermediary step on the path to true redundancy and not one that one would prefer in a practical device. The next four FIGS. (25, 26, 27, and 28) show how the architecture shown in FIG. 24 can be made into an extremely secure, practical life support system with triplex redundancy Three Oxygen Sensors, Three Auto-Calibrated/Auto-Validated, all Sensors Auto-Isolated, Gas Source Isolation, Manual Cut-Off Valve FIG. 25 describes the architecture of FIG. 24, but with the addition of manual cut-off valves 367 and 371. As can be seen in FIG. 24 the manual cut-of valve 367 is arranged on the diluent supply tube 15 for cutting of the diluent from the test valves 352, 353, 354, whereas the manual cut-of valve 367 is arranged on the oxygen supply tube 19 for cutting of the oxygen to the test valves 355, 356, 357.

All of the arguments presented pertaining to FIG. 14 apply but for a three-sensor system. This is an incremental improvement towards a high reliability oxygen sensing, auto-calibration, and auto-validation system for closed cycle life support apparatus.

Figure 25:
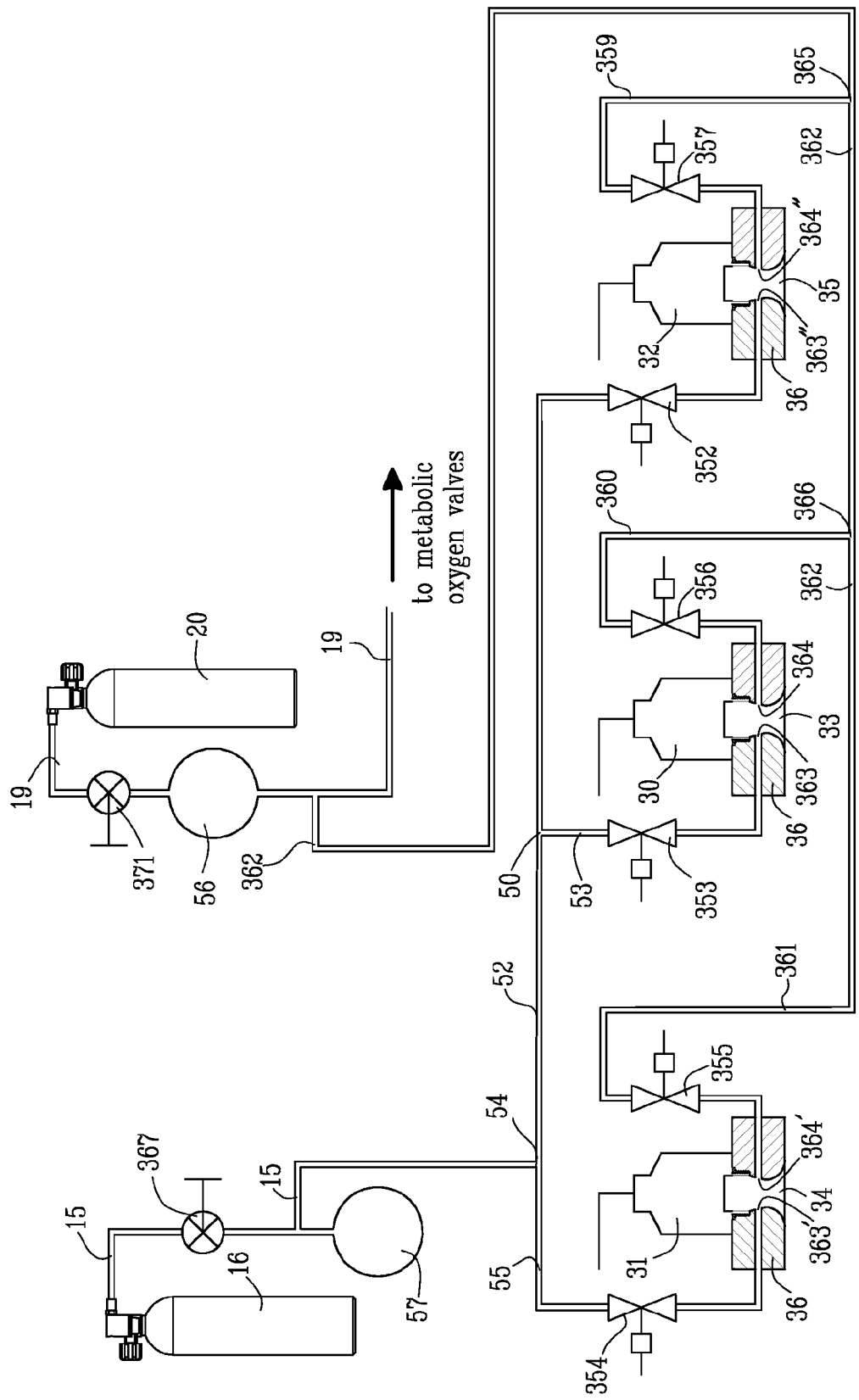
FIG. 25 is the same as FIG. 24, but with the addition of manual cut-off valves 367 and 371.
Figure 26:
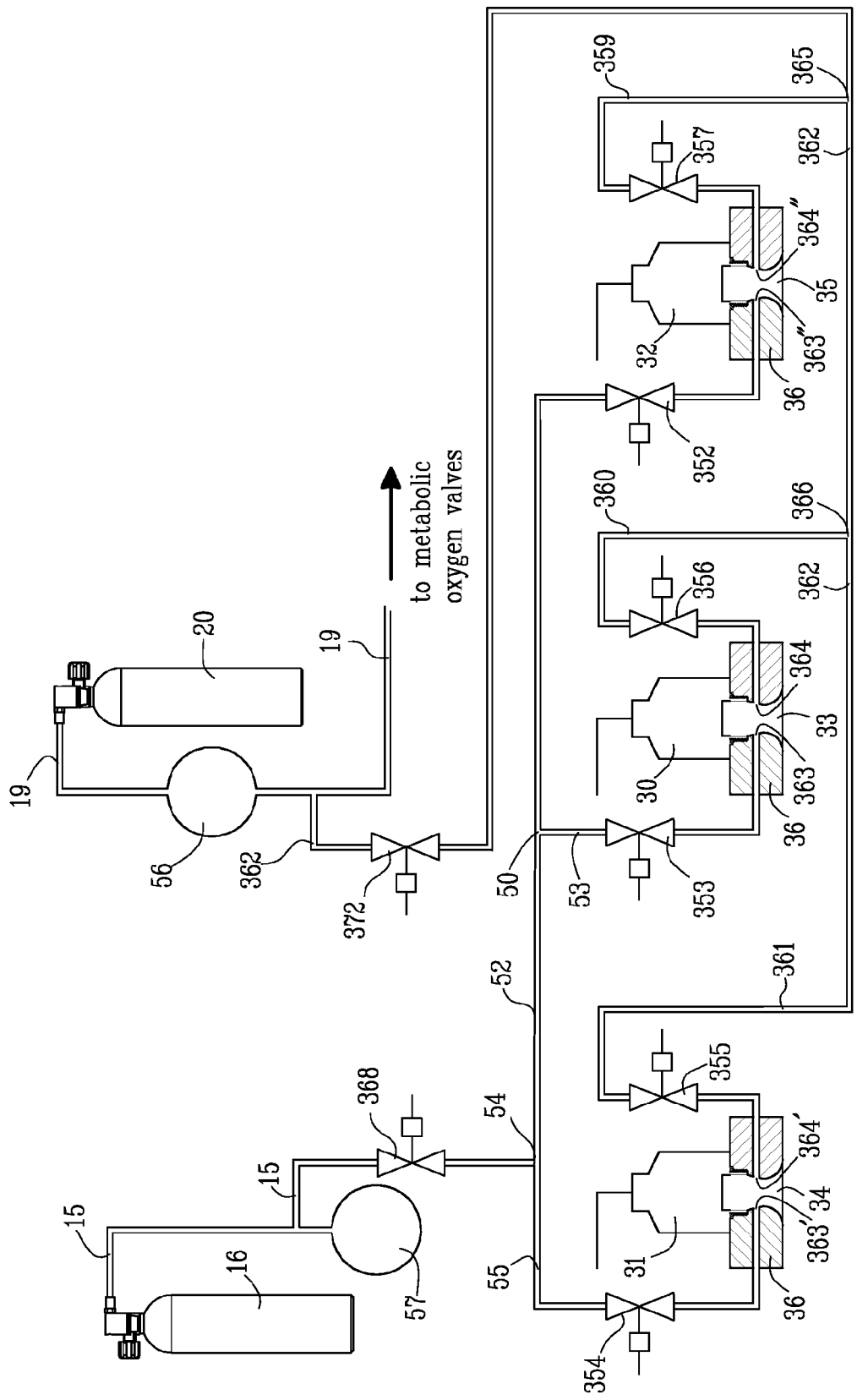
FIG. 26 is the same as FIG. 25, but with the replacement of manual cut-off valves 367, 371 with auto cut-off valves 368, 372, FIG. 27 combines the features of FIGS. 25 and 26 providing both manual cut-off valves 367 and 371 and auto cut-off valves 368, 372.

Three Oxygen Sensors, Three Auto-Calibrated/Auto-Validated, all Sensors Auto-Isolated, Gas Source Isolation, Auto Cut-Off Valve FIG. 26 describes the architecture of FIG. 25, but with the replacement of manual cut-off valves 367 and 371 with auto cut-off valves 368 and 372 being controlled by the control unit 40 so as to cut-off the auto-calibration and/or auto-validation diluent 16 and oxygen 20 gas sources respectively, also cf. FIG. 15. As can be seen in FIG. 26, the diluent cut-off valve 368 is arranged on tube 15 from the diluent source 16, whereas the oxygen cut-off valve 372 is arranged on tube 362 from the oxygen supply 20.

All of the arguments presented pertaining to FIG. 15 apply but for a three-sensor system. This is an incremental improvement towards a high reliability oxygen sensing, auto-calibration, and auto-validation system for closed cycle life support apparatus.

Figure 27:
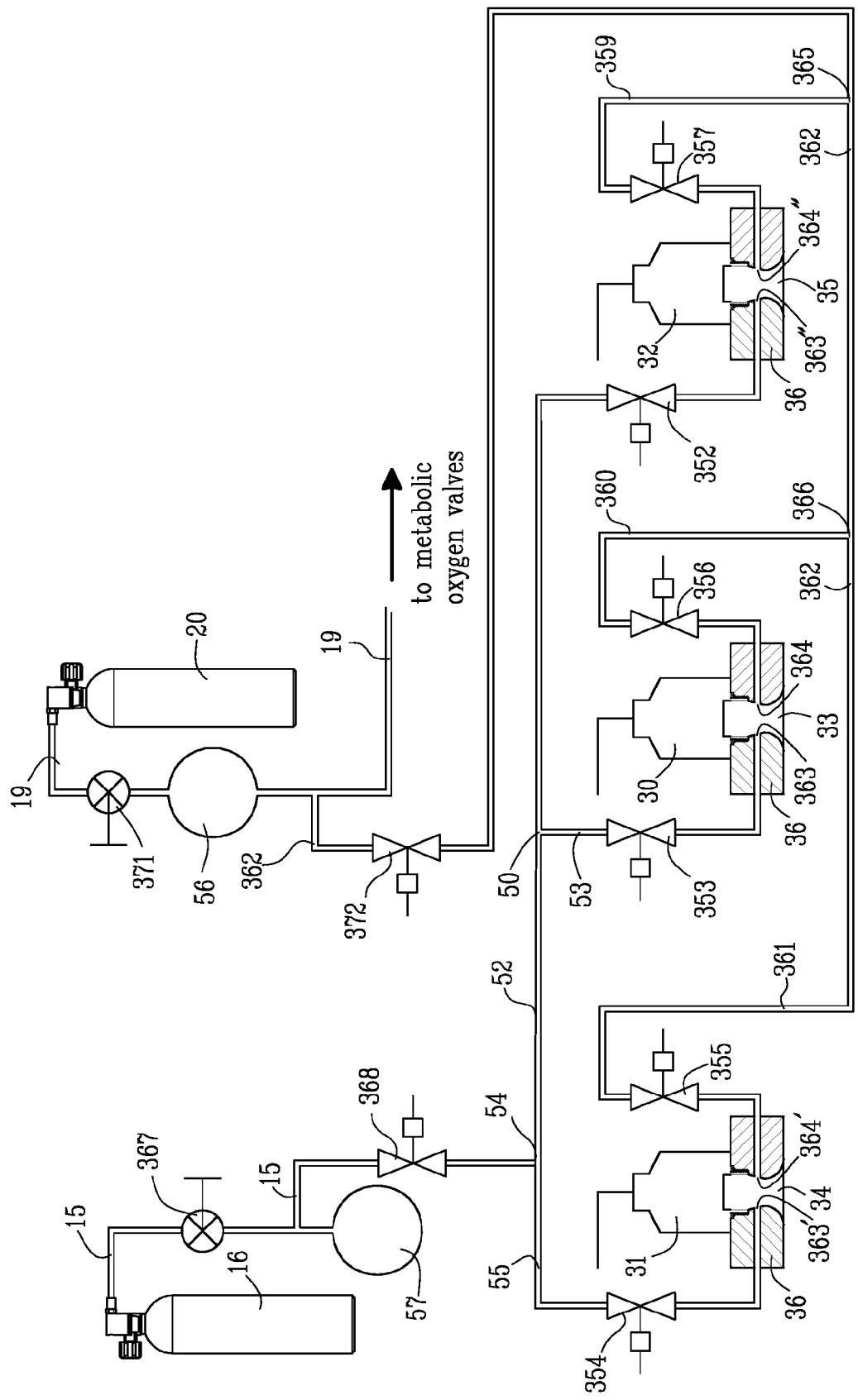

Three Oxygen Sensors, all Auto-Calibrated/Auto-Validated, all Auto-Isolated, Gas Source Isolation, Auto Cut-Off Valve and Manual Cut-Off Valve FIG. 27 combines the features of FIGS. 25 and 26 such that now we also have both the manual cut-off valves 367 and 371 as a last resort while having the benefit of the auto cut-off valves 368 and 371 to automatically handle any likely leak situation without requiring user intervention.

All of the arguments presented pertaining to FIG. 16 apply but for a three-sensor system. This is an incremental improvement towards a high reliability oxygen sensing, auto-calibration, and auto-validation system for closed cycle life support apparatus.

Figure 28:
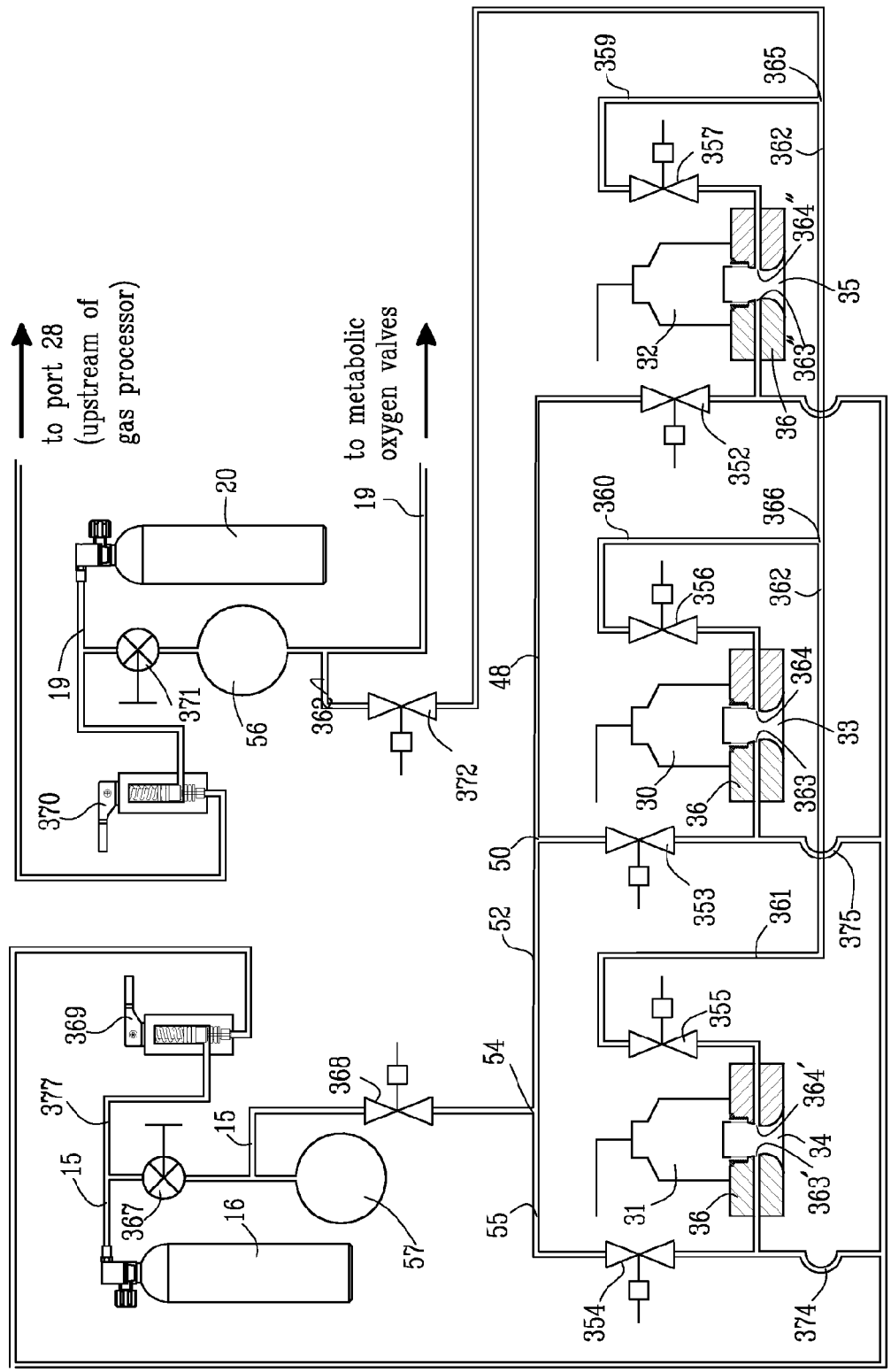
FIG. 28 is the same as FIG. 27 and adds manual bypass valves for diluent 369 and oxygen 370.

Three Oxygen Sensors, all Auto-Calibrated/Auto-Validated, all Auto-Isolated, Gas Source Isolation, Auto Cut-Off Valve, Manual Cut-Off Valve and Manual Bypass Valve FIG. 28 comprises the features of FIG. 27 and adds a manual bypass valve for both diluent 369 and for oxygen 370, also cf. FIG. 17.

All of the arguments presented pertaining to FIG. 17 apply but for a three-sensor system. This represents the second, complete triplex redundant architecture for an oxygen sensing, auto-calibration, and auto-validation control system. It allows for independent failures of each of three oxygen sensors, allows for triplex redundant isolation of those sensors in the event of a failure of the calibration test valves in the open position (leaking) and allows for a completely independent manual path for oxygen validation in the event of a complete failure of the electronics control system.

In the design of FIG. 28 a manual diluent bypass system receives gas upstream of manual cut-off valve 367 such that the possibility exists of injecting diluent gas into the system manually even in the event of the requirement to manually isolate all electronic valves in the system. In such case, manual valve 369 receives low pressure (8-12 bar) diluent from source tank 16 via gas pathway 377. When triggered manually, diluent gas then travels down gas pathway 373 to diverter pathways 374, 375, and 376 that merge with the respective outputs of auto-calibration valves 354, 353, and 352, respectively. From that junction the gas is sent to injection orifices 363, 363' that inject gas into sensing cavities 35, 34, and 33.

The nature of this injection creates a turbulent vortex that both lifts sensor condensate off the sensor while simultaneously exposing the sensor to the diluent validation gas yet not causing damage to the sensing membrane of the oxygen sensor.

Auto-Calibration and Auto-Validation of Sensors Other than Oxygen

We now extend the concepts disclosed above for sensors other than those that measure PO2 (partial pressure of oxygen) or similar. Until this time, for simplicity we have assumed that the diluent gas is air. It need not be. For deep diving operations it is common to substitute helium for all or part of the inert gas component of the diluent. It may similarly be desirable to use such a gas composition in other areas (e.g. spacesuits) where the heat transfer capacity of helium is of desirable use. It is because of the dramatically different thermal conductivity of helium (more than six times that of air) that allow helium content to be sensed with relatively simple sensors whose output is proportional to the partial pressure of helium.

Figure 6:
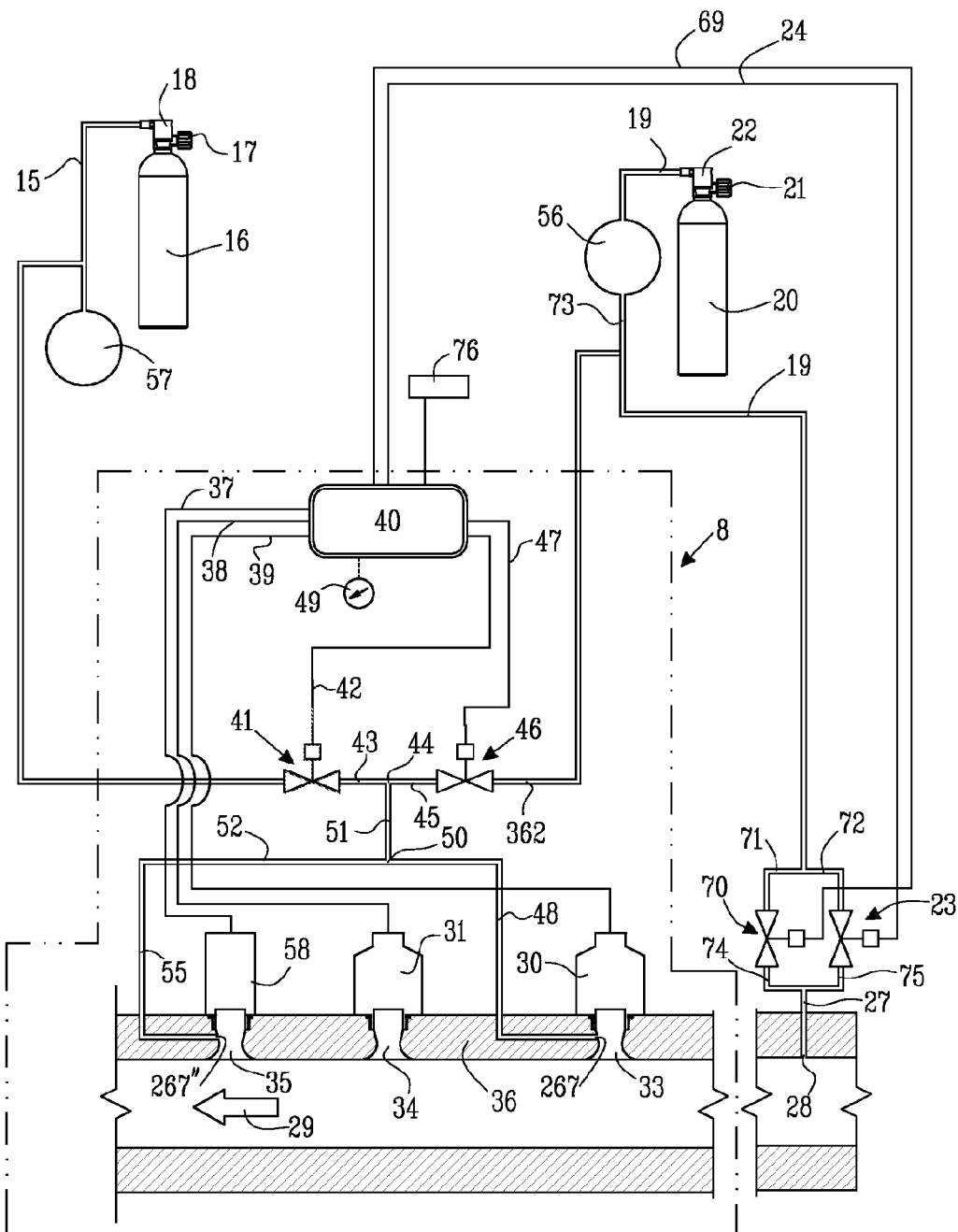
FIG. 6 shows the same as FIG. 3a, but including the addition of helium sensor 58.

In FIG. 6 we show the auto-calibration and auto-validation sensing architecture from FIG. 3a but including the addition of helium sensor 58 arranged in access port 35 and provided with diluent (or oxygen for that matter) via test orifice 267" connected to junction 50 (being previously described) via tubes 52, 55. Because the temperature-related effects being sensed are relative to the concentration of helium, we can use the same auto-calibration gases used for oxygen calibration and/or validation, and thus, via gas pathway 50, 52 and 55, route a portion of the test gases to helium sensor 58. During the course of a mission the helium sensor can be auto-validated by means of a diluent purge from test valve 41. All of the preceding arguments concerning reliability design for the oxygen sensors are applicable mutatis mutandis to helium sensing and for the sake of compactness we show here only the simplest implementation.

Similarly, in any closed cycle life support system one must deal with the presence of carbon dioxide. In almost all practical commercial closed cycle and semi-closed cycle life support systems the problem is resolved simply: an amount of carbon dioxide absorbent sufficiently large to exceed the capacity for generation of carbon dioxide during a mission—as defined by the quantity of oxygen stored in oxygen supply vessel 20—is supplied, and no sensing is necessary. There is, however, a requirement in this case for maintenance discipline in this case such that a checklist is used to assure that the CO2 absorbent is properly packed in its container and properly replaced at the same time as the oxygen supply. Nonetheless, there are certain situations in which it would be of significant utility to know, exactly, the concentration of carbon dioxide in the breathing loop, or, more-specifically, the partial pressure of CO2 in the breathing loop (detection of a non-existent, non-packed, or exhausted canister would be examples of three of these conditions). There are a number of CO2 sensing technologies that may be, with significant difficulty, implemented into a CCR or similar closed cycle life support system. We will not elaborate further on CO2 sensing technology except to state that in order for the data from such CO2 sensors to be valid in a CCR, an in-process calibration and validation system is required.

Figure 7:
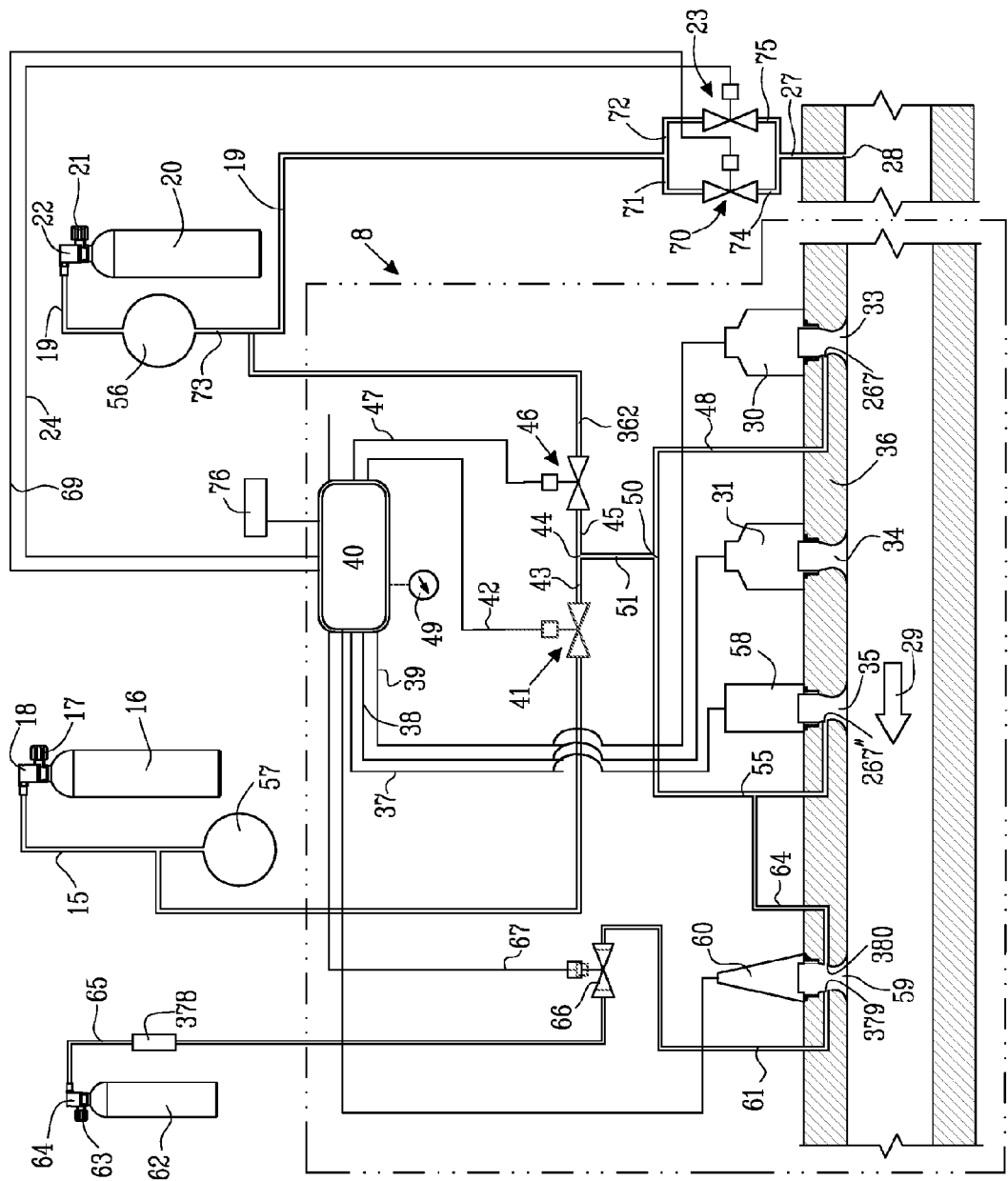
FIG. 7 shows the same as FIG. 6, but including the addition of CO2 sensor 60.

FIG. 7 shows such a system. In FIG. 7, a carbon dioxide sensor 60 is mounted such that its sensing element is able to access or view the breathing loop gas (e.g. in channel 29) via viewing/access port 59. We can use the standard test gases already described (diluent 16, or oxygen 20) to serve as a zero CO2 concentration reference point, and hence we send a portion of that auto-calibration gas to CO2 sensor 60 from junction 50 via gas pathway 64, which gas is then injected into CO2 sensing path 59 at nozzle 380.

At this point an external gas source 62 providing a reference gas containing a known fractional percent of carbon dioxide in a dry, breathable gas mixture is required to provide a second point on the PCO2 (partial pressure of carbon dioxide) calibration curve. The gas is provided via a tube 65 to a CO2 test valve 66 controlled by the control unit 40 and further via a tube 61 to a injection orifice 379.

The concentration of the CO2 calibration gas should be relatively low and approximate that of the maximum allowable concentration for short term breathing. A typical maximum allowable CO2 concentration (e.g. NIOSH safety code for exposure less than 30 minutes) is 2.5% by volume (or, respectively, 0.025 bar at STP surface conditions). Unlike the diluent 16 and oxygen 20 gas supplies, which are designed to enable the full mission duration of the CCR, the CO2 calibration gas source 62 should, for safety reasons (against the risk of the entire cal gas volume accidentally venting into the breathing loop), be of small volume, sufficient for a few dozen small calibration puffs. Even so, our design incorporates a restrictive orifice 378 prior to CO2 test valve 66 (controlled by control unit 40 via electrical cable 67) to further limit the chance of uncontrolled injection of CO2 calibration gas into the system at orifice 379. By proper choice of the restrictive orifice 378 and the concentrations of oxygen and CO2 in the CO2 calibration gas mix it will be possible to prevent complications to the user arising from any potential leak of CO2 calibration gas into the breathing loop 29—mainly because such small concentrations of CO2 will be rapidly absorbed by the CO2 scrubber within a few breathing cycles.

We now have, in FIG. 7, a system that provides a full suite of relevant real-time closed cycle life support gas mixture sensors and provides for both true auto-calibration and real-time auto-validation of each sensor. As described above for helium sensing, all of the preceding arguments concerning reliability design for the oxygen sensors can also be applied to carbon dioxide sensing and for the sake of compactness we show here only the simplest implementation.

The present invention has now been described with reference to exemplifying embodiments. However, the invention is not limited to the embodiments described herein. On the contrary, the full extent of the invention is only determined by the scope of the appended claims.

The invention claimed is:

1. An oxygen sensor arrangement for sensing the oxygen in a breathing loop of a breathing apparatus, which oxygen sensor arrangement comprises:
   at least one primary oxygen sensor arranged to operatively measure the oxygen in the breathing loop, and
   a control arrangement for obtaining measures from said oxygen sensor, wherein:
   said at least one primary oxygen sensor is arranged in a cavity that is in fluid communication with the breathing loop; and
   said cavity is provided with at least one output orifice for a test channel arrangement, which output orifice is arranged at a position adjacent to, or directly adjacent to said at least one primary oxygen sensor, and
   said test channel arrangement is adapted to operatively provide a first gas having a first known fraction of oxygen from a first gas supply to said primary oxygen sensor at a position adjacent to or directly adjacent to said primary oxygen sensor, and
   at least a first test valve arrangement is arranged to operatively open and close the flow of said first gas through said test channel arrangement, and
   said control arrangement is arranged to operatively actuate said first test valve arrangement so as to provide an amount of said first gas to said primary oxygen sensor via said test channel arrangement, and
   said control arrangement is arranged to operatively obtain measures from said primary oxygen sensor.

2. The oxygen sensor arrangement according to claim 1, wherein:
   the test channel arrangement is adapted to provide a second gas having a second known fraction of oxygen from a second gas supply to said primary oxygen sensor at a position adjacent to or directly adjacent to said primary oxygen sensor, and
   at least a second test valve arrangement is arranged to operatively open and close the flow of said second gas through said test channel arrangement, and
   said control arrangement is arranged to operatively actuate said second test valve arrangement so as to provide an amount of said second gas to said primary oxygen sensor via said test channel arrangement.

3. The oxygen sensor arrangement according to claim 2, wherein:
said test channel arrangement comprises:
   a first test channel arrangement for providing said first gas from said first gas supply to said primary oxygen sensor at a first position adjacent to or directly adjacent to said primary oxygen sensor, and
   a second test channel arrangement for providing said second gas from said second gas supply to said primary oxygen sensor at a second position adjacent to or directly adjacent to said primary oxygen sensor.

4. The oxygen sensor arrangement according to claim 1, wherein:
   said control arrangement is arranged to operatively obtain at least one first test measure from said primary oxygen sensor when it is provided with an amount of said first gas.

5. The oxygen sensor arrangement according to claim 2, wherein:
   said control arrangement is arranged to operatively obtain at least one second test measure from said primary oxygen sensor when it is provided with an amount of said second gas.

6. The oxygen sensor arrangement according to claim 5, wherein said control arrangement is arranged to operatively:
   calculate a at least first calibration point using said first test measure and at least using the known fraction of oxygen in the first gas,
   calculate a at least second calibration point using said second test measure and at least using the known fraction of oxygen in the second gas, and generate a calibration curve for said primary oxygen sensor at least based on said first calibration point and said second calibration point.

7. The oxygen sensor arrangement according to claim 5, wherein said control arrangement is arranged to operatively:
obtain a validation point value using said first test measure or said second test measure,
obtain an expected value for the validation point value, at least using the known fraction of oxygen in the first gas or the known fraction of oxygen in the second gas, and
determine if the validation point value deviates from the expected value more than a predetermined amount.

8. The oxygen sensor arrangement according to claim 6, wherein said control arrangement is arranged to operatively:
obtain the expected value for the validation point value by using the calibration curve so as to compensate for possible deviations in said primary oxygen sensor.

9. The oxygen sensor arrangement according to claim 1, wherein:
at least on of said first gas or said second gas is operatively injected at an oblique angle with respect to the surface of the primary oxygen sensor.

10. The oxygen sensor arrangement according to claim 1, further comprising at least one secondary oxygen sensor for measuring the oxygen in the breathing loop, wherein:
said control arrangement is arranged to operatively obtain measures from the secondary oxygen sensor and the primary sensor when no test valve arrangements are actuated to provide any of the first gas or the second gas onto the secondary oxygen sensor or the primary sensor.

11. The oxygen sensor arrangement according to claim 10, wherein:
said control arrangement is arranged to operatively actuate at least one of said first test valve arrangement or said second test valve arrangement if the primary sensor measures deviates from the secondary oxygen sensor measures more than a predetermined amount.

12. The oxygen sensor arrangement according to claim 10, wherein:
said secondary oxygen sensor is arranged at a distance from the gas output of at least one of said first test valve arrangement or said second test valve arrangement, such that a gas leakage from at least one of said first test valve arrangement or said second test valve arrangement will cause the secondary sensor to operatively provide a different measure compared to the measure provided by the primary oxygen sensor.

13. The oxygen sensor arrangement according to claim 2, wherein:
at least one cut-off valve arrangement, operable by the control arrangement, is arranged to operatively cut-off a possible gas leakage from at least one of said first test valve arrangement or said second test valve arrangement to said at least one primary oxygen sensor.

* * * * *